(12) United States Patent
Hattori et al.

(10) Patent No.: US 10,575,803 B2
(45) Date of Patent: Mar. 3, 2020

(54) RADIOGRAPHY SYSTEM AND METHOD FOR OPERATING RADIOGRAPHY SYSTEM

(71) Applicant: FUJIFILM Corporation, Tokyo (JP)

(72) Inventors: Masato Hattori, Ashigarakami-gun (JP); Ryo Imamura, Ashigarakami-gun (JP); Koichi Kitano, Ashigarakami-gun (JP); Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 16 days.

(21) Appl. No.: 16/059,479

(22) Filed: Aug. 9, 2018

(65) Prior Publication Data
US 2019/0046139 A1   Feb. 14, 2019

(30) Foreign Application Priority Data
Aug. 10, 2017   (JP) .................... 2017-156064

(51) Int. Cl.
*A61B 6/00*   (2006.01)

(52) U.S. Cl.
CPC ............ *A61B 6/469* (2013.01); *A61B 6/4283* (2013.01); *A61B 6/4405* (2013.01); *A61B 6/461* (2013.01); *A61B 6/465* (2013.01); *A61B 6/467* (2013.01); *A61B 6/48* (2013.01); *A61B 6/547* (2013.01); *A61B 6/563* (2013.01); *A61B 6/586* (2013.01)

(58) Field of Classification Search
CPC ... A61B 6/4028; A61B 6/4283; A61B 6/4405; A61B 6/464; A61B 6/563; A61B 6/022; A61B 6/08; A61B 6/4233; A61B 6/469; A61B 6/587; A61B 6/588

USPC .......................................................... 378/62
See application file for complete search history.

(56) References Cited

U.S. PATENT DOCUMENTS

| | | | | |
|---|---|---|---|---|
| 5,539,798 A | * | 7/1996 | Asahina ................. | A61B 6/022 348/E5.086 |
| 2002/0012450 A1 | * | 1/2002 | Tsujii ...................... | H04N 5/32 382/103 |
| 2010/0054416 A1 | * | 3/2010 | Tsubota ................... | A61B 6/00 378/98 |
| 2010/0079273 A1 | * | 4/2010 | Tsubota ................ | H04W 48/02 340/539.1 |
| 2010/0243910 A1 | * | 9/2010 | Tsubota ............... | A61B 6/4283 250/393 |
| 2012/0250825 A1 | * | 10/2012 | Yoshida ............... | A61B 6/4233 378/91 |
| 2013/0114793 A1 | | 5/2013 | Ohta et al. | |
| 2013/0121468 A1 | * | 5/2013 | Ohta .................... | A61B 6/4405 378/63 |

(Continued)

FOREIGN PATENT DOCUMENTS

| JP | 6-217973 A | 8/1994 |
|---|---|---|
| JP | 2012-24399 A | 2/2012 |

*Primary Examiner* — Taeho Jo
(74) *Attorney, Agent, or Firm* — Birch, Stewart, Kolasch & Birch, LLP

(57) ABSTRACT

In the radiography system, a camera image of the usage environment in which the electronic cassette is used is captured. An in-image cassette region of the electronic cassette is detected from the camera image. The cassette ID of the electronic cassette is acquired from the in-image cassette region. The acquired cassette ID is collated with the cassette ID of the use cassette set in the console to check whether the use cassette is present.

20 Claims, 35 Drawing Sheets

(56) References Cited

U.S. PATENT DOCUMENTS

| | | | |
|---|---|---|---|
| 2013/0259196 A1* | 10/2013 | Tajima | A61B 6/42 378/62 |
| 2014/0275954 A1* | 9/2014 | Ohta | G16H 40/63 600/407 |
| 2015/0222134 A1* | 8/2015 | Ikegame | H02J 7/0045 320/107 |
| 2015/0279196 A1* | 10/2015 | Tajima | G08B 13/22 340/539.32 |
| 2016/0015340 A1* | 1/2016 | Nenoki | A61B 6/4283 378/98 |
| 2016/0081650 A1* | 3/2016 | Okusu | A61B 6/56 378/62 |
| 2016/0174918 A1* | 6/2016 | Wang | A61B 6/4405 378/63 |
| 2017/0135667 A1* | 5/2017 | Becker | A61B 6/4411 |
| 2017/0219498 A1* | 8/2017 | Chtcheprov | G01N 23/046 |

\* cited by examiner

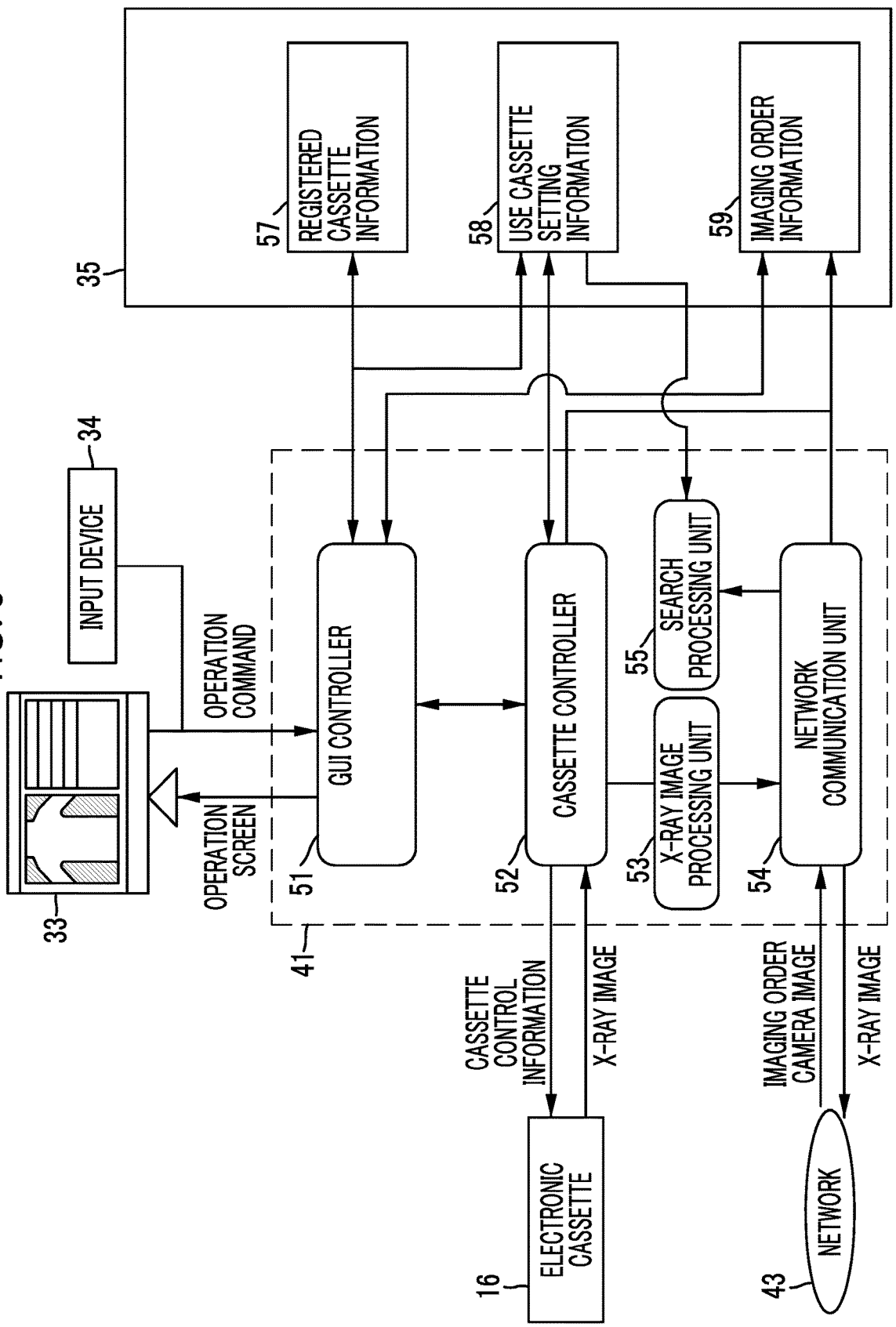

| REGISTERED CASSETTE INFORMATION |||||
|---|---|---|---|---|
| CASSETTE ID | NAME | SIZE | COMMUNICATION ADDRESS | SPECIFICATION INFORMATION |
| DR0001 | CASSETTE A | 14 × 17 TYPE | adr0001 | 📄 |
| DR0002 | CASSETTE B | 10 × 12 TYPE | adr0002 | 📄 |
| DR0003 | CASSETTE C | 14 × 17 TYPE | adr0003 | 📄 |
| DR0004 | CASSETTE D | 17 × 17 TYPE | adr0004 | 📄 |
| DR0005 | CASSETTE E | 14 × 17 TYPE | adr0005 | 📄 |

| USE CASSETTE SETTING INFORMATION |||||
|---|---|---|---|---|
| CASSETTE ID | NAME | SETTING INFORMATION | STATUS | IMAGING ORDER |
| DR0001 | CASSETTE A | UNSET | - | - |
| DR0002 | CASSETTE B | UNSET | - | - |
| DR0003 | CASSETTE C | UNSET | - | - |
| DR0004 | CASSETTE D | UNSET | - | - |
| DR0005 | CASSETTE E | UNSET | - | - |

| ORDER ID | SUBJECT ID | IMAGING MENU | COMPLETION INFORMATION | USE CASSETTE |
|---|---|---|---|---|
| OD0001 | P0400 | CHEST/UPRIGHT POSITION/FRONT | IMAGING COMPLETED | DR0001 |
| OD0002 | P0500 | ABDOMEN/DECUBITUS POSITION/FRONT | UNCOMPLETED | - |
| OD0003 | P0600 | CHEST/UPRIGHT POSITION/FRONT | UNCOMPLETED | - |

USE CASSETTE SELECTION SCREEN

REGISTERED CASSETTE INFORMATION

| CASSETTE ID | NAME | SIZE | COMMUNICATION ADDRESS | SPECIFICATION INFORMATION |
|---|---|---|---|---|
| DR0001 | CASSETTE A | 14 × 17 TYPE | adr0001 | |
| DR0002 | CASSETTE B | 10 × 12 TYPE | adr0002 | |
| DR0003 | CASSETTE C | 14 × 17 TYPE | adr0003 | |
| DR0004 | CASSETTE D | 17 × 17 TYPE | adr0004 | |
| DR0005 | CASSETTE E | 14 × 17 TYPE | adr0005 | |

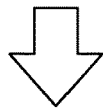

(B)

| | | |
|---|---|---|
| <image placeholder> | IMAGING ORDER "OD0001"<br>IMAGING MENU: CHEST, UPRIGHT POSITION, FRONT | CASSETTE ID "DR0001"  NAME "A" |
| | IMAGING ORDER "OD0002"<br>IMAGING MENU: ABDOMEN, DECUBITUS POSITION, FRONT | CASSETTE ID "DR0003"  NAME "C" |
| | IMAGING ORDER "OD0003"<br>IMAGING MENU: ABDOMEN, DECUBITUS POSITION, FRONT | |

FIG. 12

57 — REGISTERED CASSETTE INFORMATION

| CASSETTE ID | NAME | SIZE | COMMUNICATION ADDRESS | SPECIFICATION INFORMATION |
|---|---|---|---|---|
| DR0003 | CASSETTE C | 14 × 17 TYPE | adr0003 | |

58 — USE CASSETTE SETTING INFORMATION

| CASSETTE ID | NAME | SETTING INFORMATION | STATUS | IMAGING ORDER |
|---|---|---|---|---|
| DR0001 | CASSETTE A | UNSET | - | - |
| DR0002 | CASSETTE B | UNSET | - | - |
| DR0003 | CASSETTE C | SET | READY | OD0002 |
| DR0004 | CASSETTE D | UNSET | - | - |
| DR0005 | CASSETTE E | UNSET | - | - |

59

| ORDER ID | SUBJECT ID | IMAGING MENU | COMPLETION INFORMATION | USE CASSETTE |
|---|---|---|---|---|
| OD0001 | P0400 | CHEST/SEATED POSITION/FRONT | IMAGING COMPLETED | DR0001 |
| OD0002 | P0500 | ABDOMEN/DECUBITUS POSITION/FRONT | UNCOMPLETED | - |

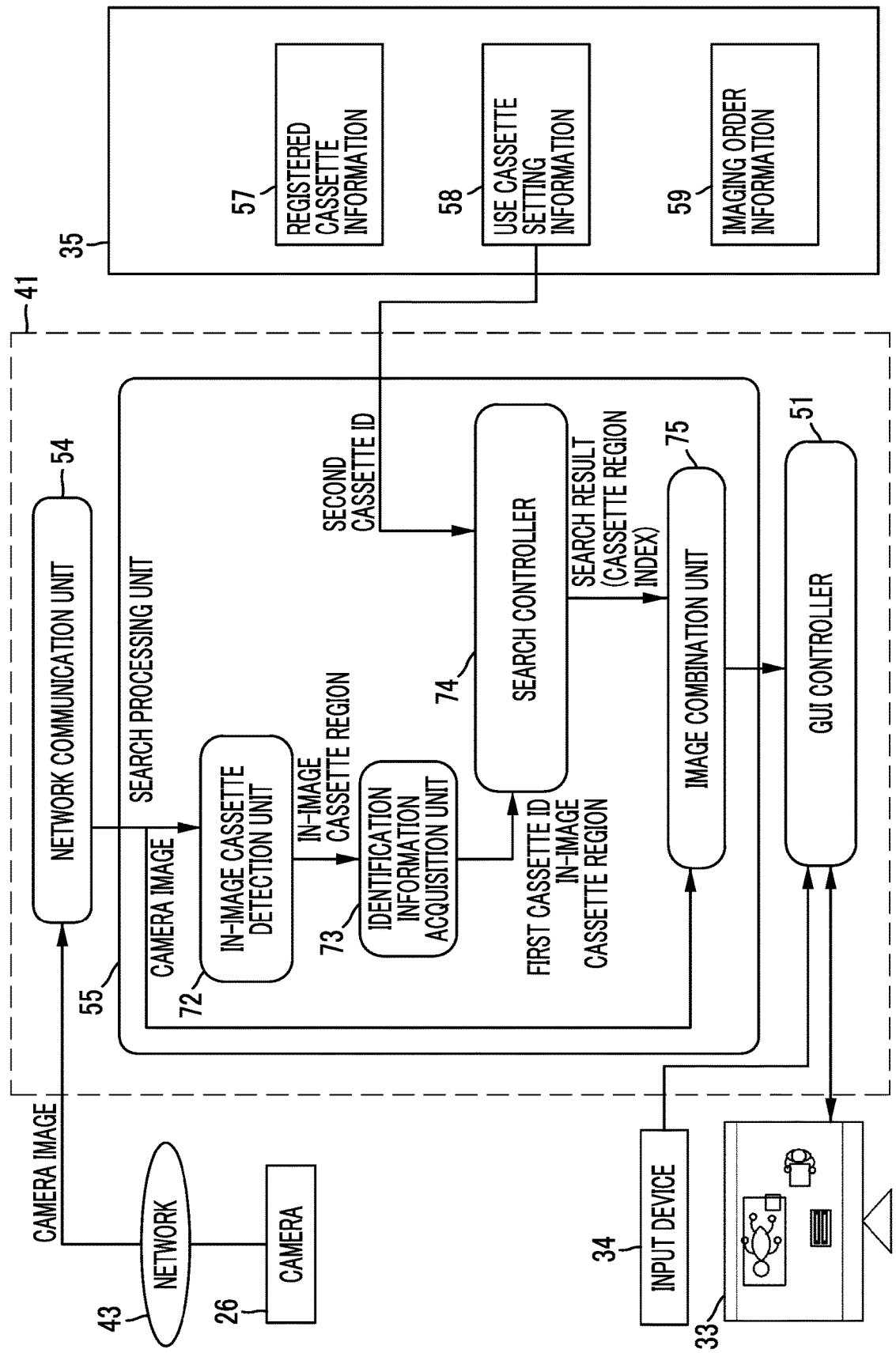

FIG. 36
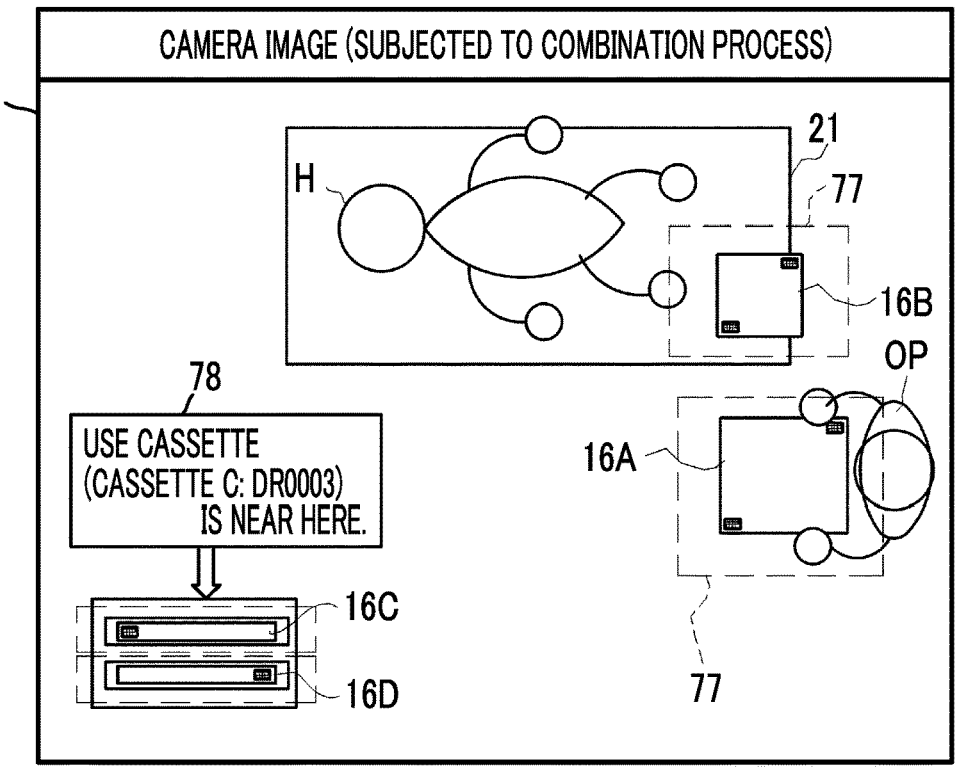
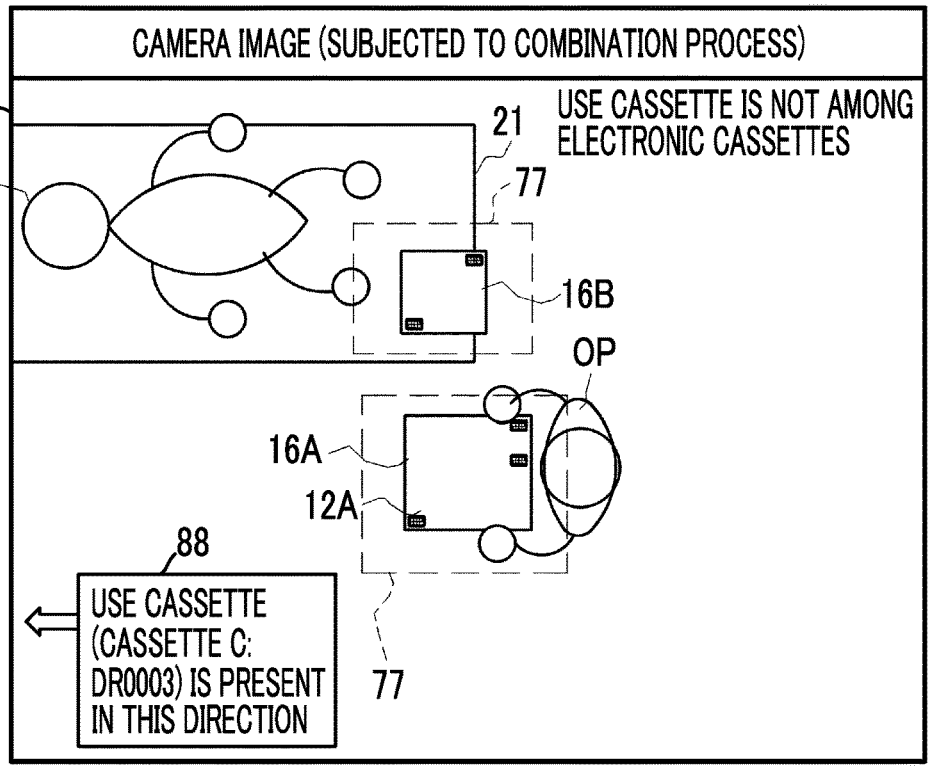

FIG. 38
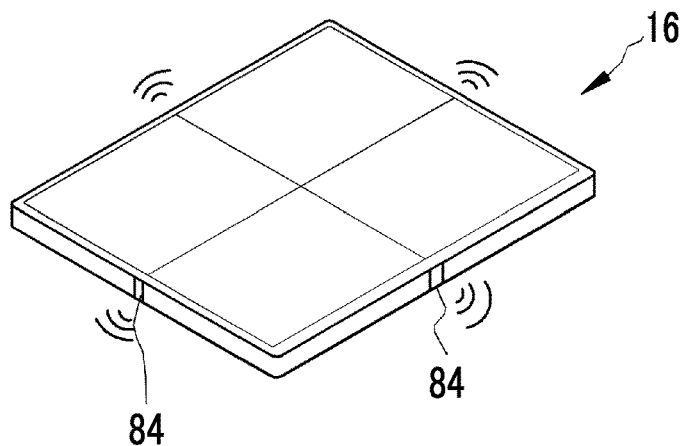
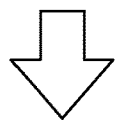
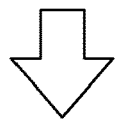
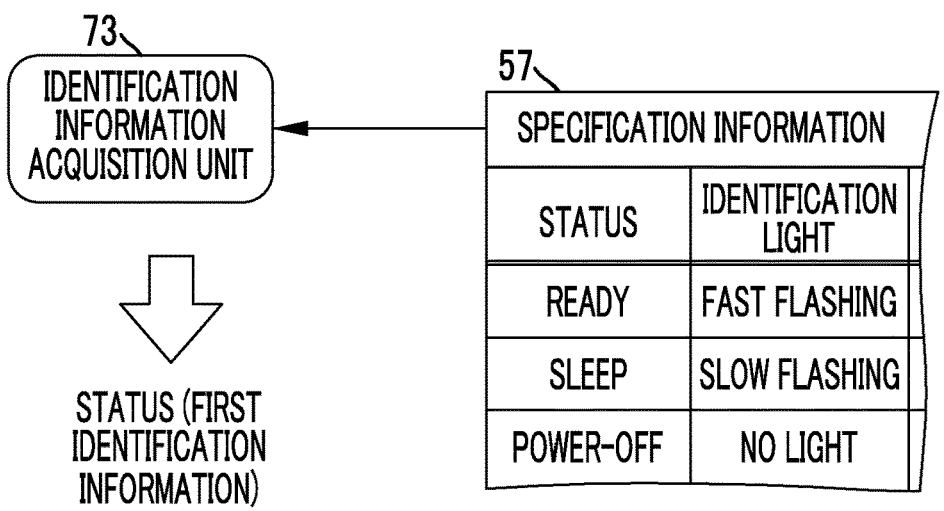

FIG. 39
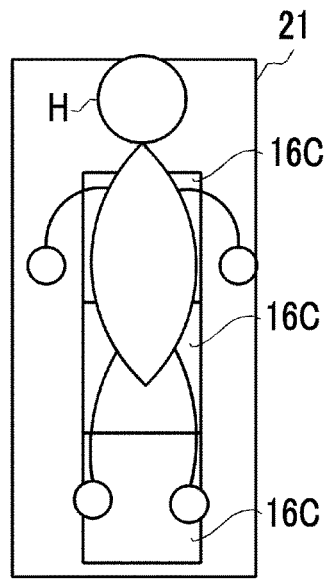
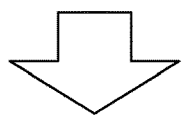
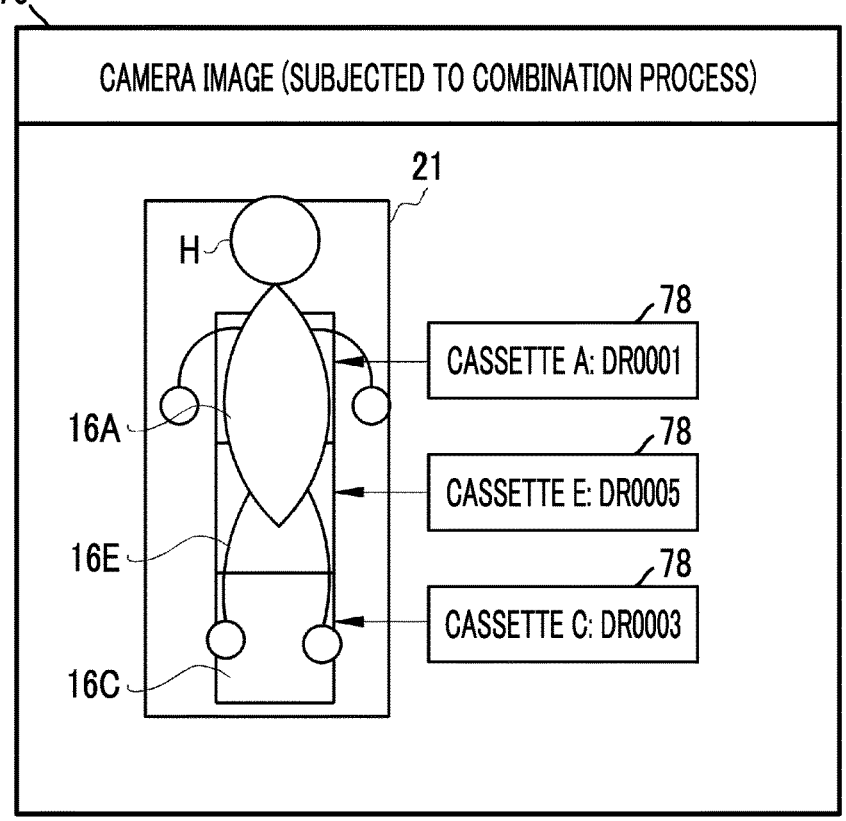

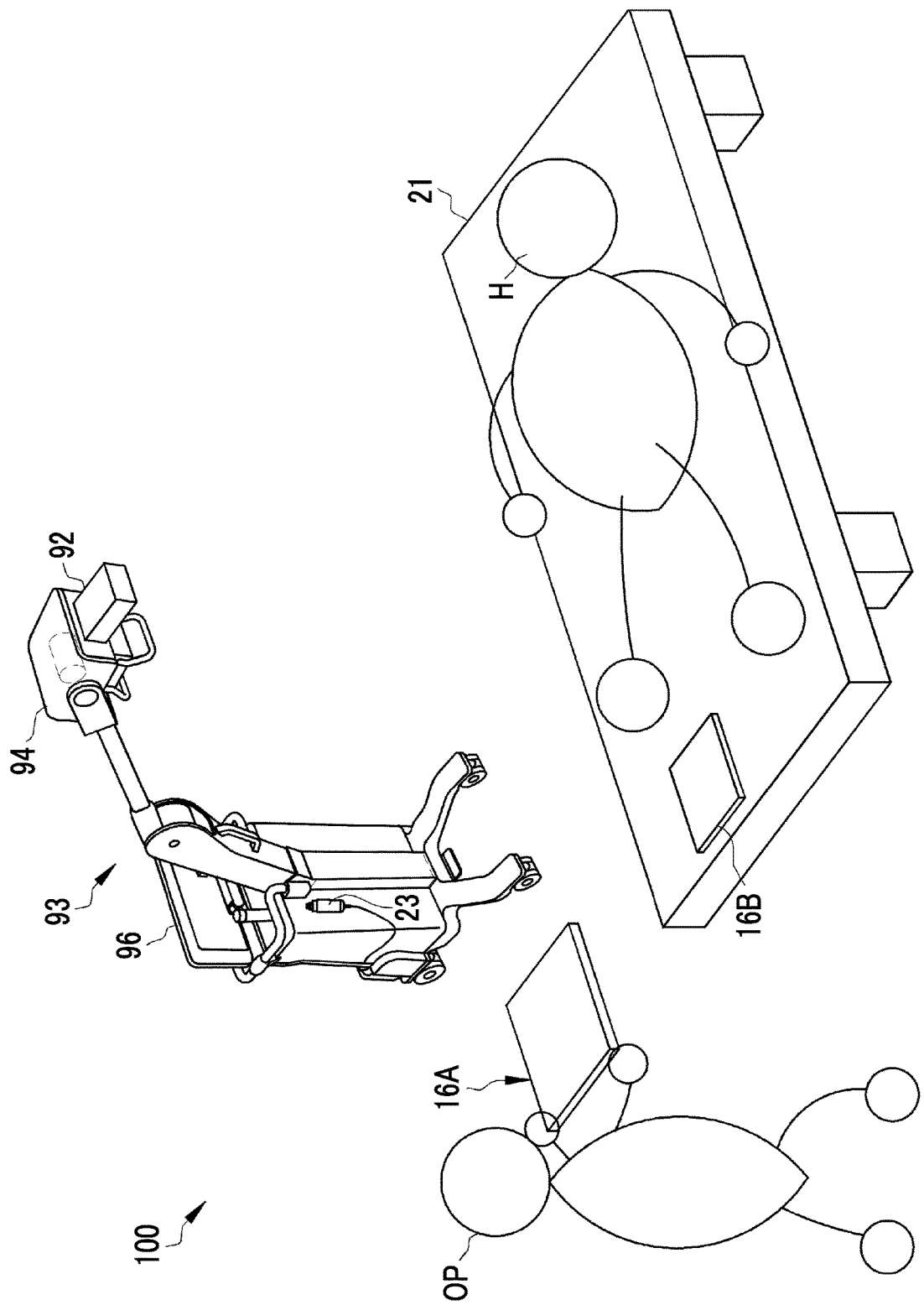

RADIOGRAPHY SYSTEM AND METHOD FOR OPERATING RADIOGRAPHY SYSTEM

CROSS-REFERENCE TO RELATED APPLICATION

This application claims priority under 35 USC 119 from Japanese Patent Application No. 2017-156064, filed 10 Aug. 2017, the disclosure of which is incorporated by reference herein.

BACKGROUND OF THE INVENTION

1. Field of the Invention

The present invention relates to a radiography system that performs radiography using an electronic cassette and a method for operating the radiography system.

2. Description of the Related Art

In a medical field, a diagnosis is made on the basis of a radiographic image detected by a radiographic image detection device. The radiographic image detection device includes a sensor panel. The sensor panel is provided with an imaging region. A plurality of pixels are two-dimensionally arranged in the imaging region. The pixel is sensitive to radiation which has been emitted from a radiation generation apparatus and then transmitted through a subject (patient) and accumulates charge. The radiographic image detection device converts the charge accumulated in the pixel into a digital signal and outputs the digital signal as a radiographic image.

The radiographic image detection devices are classified into a fixed type that is fixed to an imaging stand installed in an imaging room and a portable type in which, for example, a sensor panel is accommodated in a portable housing. The portable radiographic image detection device is referred to as an electronic cassette. The electronic cassettes are classified into a wired type that is supplied with power from a commercial power supply through a cable and a wireless type that is supplied with power from a battery provided in a housing.

The electronic cassette is used in various environments. The electronic cassette is used in the imaging room. In many cases, the electronic cassette is carried out of the imaging room and is then used since it has high mobility. For example, the electronic cassette is used for visit imaging in which an operator visits a hospital room in which a patient who is not able to move to the imaging room is present and takes a radiographic image. In addition, the electronic cassette is used in places other than medical facilities in order to capture a radiographic image of an aged person who gets medical treatment at home or a patient who is in an emergency condition due to an accident or a disaster. Hereinafter, imaging without using an imaging stand is referred to as free imaging.

In a preparation operation before radiography, an operator, such as a radiology technician, relatively positions a radiation generation apparatus, an electronic cassette, and a patient. After positioning is completed, the operator operates the radiation generation apparatus to emit radiation and takes a radiographic image. JP2012-024399A (corresponding to US2013/114793A1) and JP1994-217973 (JP-H06-217973A, corresponding to U.S. Pat. No. 5,539,798A) disclose a technique which appropriately assists positioning using an optical camera that captures an image of a patient or an electronic cassette in the direction in which the radiation generation apparatus is disposed. For example, guide lines for positioning are inserted into a camera image captured by the camera and the camera image is displayed on a display unit. The operator can perform positioning while seeing the guide lines.

SUMMARY OF THE INVENTION

However, in a case in which the electronic cassettes are used, a plurality of electronic cassettes may be present in the usage environment. For example, in many cases, a plurality of electronic cassettes with different sizes or purposes are provided in the imaging room. During visit imaging, in some cases, a treatment cart is provided with a plurality of electronic cassettes and the plurality of electronic cassettes are carried in a hospital room which is the usage environment.

In a case in which the electronic cassette is the wireless type, an operation of pairing the electronic cassette used for imaging and a console needs to be performed before imaging. The console is a control device that controls the electronic cassette or acquires a radiographic image from the electronic cassette. The pairing means an operation of setting, as a use cassette, an electronic cassette used for imaging, that is, an electronic cassette selected as a communication partner of the console during imaging in the console.

In a case in which the pairing is completed, of course, the use cassette and the console are not physically connected to each other by, for example, a cable, but are logically connected to each other. Therefore, in a case in which a plurality of electronic cassettes are present in the usage environment, the operator may not identify use cassette among the plurality of electronic cassettes even after the pairing is completed.

In a case in which the operator falsely recognizes a non-use cassette, which is an electronic cassette other than the paired use cassette, as the use cassette and uses the non-use cassette for imaging, the non-use cassette does not normally operate and it is difficult to obtain a radiographic image of the patient.

For this reason, the technique disclosed in JP2012-024399A and JP1994-217973 (JP-H06-217973A) which easily searches for the use cassette from a plurality of electronic cassettes in the usage environment using the optical camera has been examined. JP2012-024399A and JP1994-217973 (JP-H06-217973A) disclose the technique which assists positioning using the camera, but do not disclose solutions to the above-mentioned problems.

An object of the invention is to provide a radiography system that enables a user to simply find a use cassette selected as an electronic cassette used for imaging in a console from a plurality of electronic cassettes in a usage environment and a method for operating the radiography system.

According to an aspect of the invention, there is provided a radiography system comprising an electronic cassette, a console, a camera image acquisition unit, an in-image cassette detection unit, an identification information acquisition unit, a collation unit, a search controller, and a display controller. The electronic cassette detects a radiographic image based on radiation which has been emitted from a radiation generation apparatus and transmitted through a subject. The console communicates with the electronic cassette to acquire the radiographic image. The camera image acquisition unit acquires a camera image, which indicates a usage environment including a place in which the electronic cassette is used and a periphery of the place, from an optical camera that captures the usage environment. The in-image cassette detection unit detects the electronic cassette included in the camera image on the basis of the camera image and outputs an in-image cassette region of the detected electronic cassette. The identification information acquisition unit acquires identification information of the electronic cassette included in the camera image as first identification information on the basis of the camera image. The collation unit collates the first identification information with second identification information which is identification information of a use cassette set as the electronic cassette used for radiography in the console. The search controller determines the electronic cassette having the first identification information matched with the second identification information as the use cassette on the basis of a collation result of the collation unit, determines whether the use cassette is present in the camera image, generates a cassette region index indicating the in-image cassette region of the use cassette in a case in which the use cassette is determined to be present in the camera image, and outputs the cassette region index as a search result. The display controller performs control such that the cassette region index and the camera image are displayed on a display unit.

The camera image is, for example, a motion picture or a still image.

For example, the camera is provided in the radiation generation apparatus or is provided in a room in a case in which the usage environment is an indoor environment.

For example, the first identification information and the second identification information include a first cassette ID and a second cassette ID, each of which includes a character string uniquely given to each electronic cassette, respectively.

In a case in which an ID marker indicating the first cassette ID is attached to an outer surface of the electronic cassette, for example, the identification information acquisition unit detects the ID marker from the camera image and acquires the first cassette ID and the collation unit collates the first cassette ID with the second cassette ID.

For example, each of the first identification information and the second identification information may include information indicating an operating state of the electronic cassette.

In a case in which a light source that emits identification light which is light indicating the first identification information is provided in the electronic cassette, the identification information acquisition unit may detect the identification light from the camera image and acquire the first identification information.

Preferably, the identification light is identified on the basis of at least one of a color, a lighting pattern, or a lighting time.

The radiography system may further comprise: a direction detection unit that detects a direction in which the electronic cassette is present in the usage environment on the basis of the in-image cassette region; and a request signal transmission unit that transmits an identification information request signal for requesting the first identification information to the electronic cassette. In a case in which the electronic cassette is included in the camera image, the request signal transmission unit may transmit the identification information request signal in the direction detected by the direction detection unit and receive the first identification information as a response from the electronic cassette. The identification information acquisition unit may acquire the first identification information received by the request signal transmission unit.

The identification information acquisition unit may output a warning in a case in which the electronic cassette is included in the camera image, but the first identification information is not capable of being acquired from the electronic cassette.

In a case in which a plurality of the electronic cassettes are included in the camera image, the search controller may output only the cassette region index for the use cassette among all of the electronic cassettes in the camera image.

In a case in which a plurality of the electronic cassettes are included in the camera image, the in-image cassette detection unit may detect the in-image cassette regions of all of the electronic cassettes in the camera image. The search controller may generate the cassette region indices indicating the in-image cassette regions of all of the electronic cassettes. In a case in which the use cassette is present in the camera image, the search controller may output the cassette region indices of the use cassette and the electronic cassettes other than the use cassette in different aspects.

In a case in which the use cassette is absent in the camera image, the search controller may output, as the search result, a message indicating that the use cassette is absent in the camera image.

In a case in which the use cassette is absent in the camera image, the display controller may display only the camera image on the display unit.

In a case in which a plurality of the electronic cassettes are included in the camera image and do not include the use cassette, the search controller may output a selection operation portion for selecting any one of the plurality of electronic cassettes included in the camera image as the use cassette, receive an input of an operation for the selection operation portion through the selection operation portion displayed on the display unit, and set the selected electronic cassette as the use cassette.

In a case in which a field of view of the camera image is changed and the use cassette that has been present in the camera image before the field of view is changed disappears from the camera image after the field of view is changed, the search controller may output a direction index indicating a direction in which the use cassette that has been present in the camera image before the field of view is changed is present and the display controller may display the camera image whose field of view has been changed and the direction index on the display unit.

The radiography system may further comprise an irradiation prohibition signal output unit that outputs an irradiation prohibition signal for prohibiting the start of the emission of the radiation in the radiation generation apparatus in a case in which the use cassette is absent in the camera image.

In long-length imaging in which radiography is performed, with two or more of electronic cassettes arranged in a line, and a plurality of radiographic images detected by the electronic cassettes are combined to generate a radiographic image indicating a long imaging range, in a case in which a plurality of electronic cassettes are included in the camera image and include two or more use cassettes, the search controller may output the cassette region indices indicating the in-image cassette regions of the two or more use cassettes in the camera image.

In a case in which an arrangement order of the plurality of electronic cassettes used for the long-length imaging is set in the console, the search controller may generate an arrangement order screen on which first arrangement order information in which the arrangement order of the plurality of electronic cassettes included in the camera image is represented by the first identification information and second arrangement order information in which an arrangement order of the plurality of electronic cassettes set in the console is represented by the second identification information are displayed in parallel.

According to another aspect of the invention, there is provided a method for operating a radiography system comprising an electronic cassette that detects a radiographic image based on radiation which has been emitted from a radiation generation apparatus and transmitted through a subject and a console that communicates with the electronic cassette to acquire the radiographic image. The method comprises a camera image acquisition step, an in-image cassette detection step, an identification information acquisition step, a collation step, a search control step, and a display control step. In the camera image acquisition step, a camera image which indicates a usage environment including a place in which the electronic cassette is used and a periphery of the place is acquired from an optical camera which captures the usage environment. In the in-image cassette detection step, the electronic cassette included in the camera image is detected on the basis of the camera image and an in-image cassette region of the detected electronic cassette is output. In the identification information acquisition step, identification information of the electronic cassette included in the camera image is acquired as first identification information on the basis of the camera image. In the collation step, the first identification information is collated with second identification information which is identification information of a use cassette set as the electronic cassette used for radiography in the console. In the search control step, the electronic cassette having the first identification information matched with the second identification information is determined as the use cassette on the basis of a collation result in the collation step; it is determined whether the use cassette is present in the camera image; a cassette region index indicating the in-image cassette region of the use cassette is generated in a case in which the use cassette is determined to be present in the camera image; and the cassette region index is output as a search result. In the display control step, control is performed such that the cassette region index and the camera image are displayed on a display unit.

According to the invention, it is determined whether the use cassette that has been selected as the electronic cassette used for imaging in the console is present in the camera image obtained by capturing the usage environment. In a case in which the use cassette is determined to be present in the camera image, the camera image and the cassette region index indicating the in-image cassette region of the use cassette are displayed. Therefore, it is possible to simply find the use cassette selected in the console from a plurality of electronic cassettes in the usage environment.

BRIEF DESCRIPTION OF THE DRAWINGS

FIG. 5 is a functional block diagram illustrating each unit for implementing the basic function of the console.

FIG. 6 is a diagram illustrating registered cassette information.

FIG. 7 is a diagram illustrating use cassette setting information.

FIG. 8 is a diagram illustrating imaging order information.

FIG. 11 is a diagram illustrating a use cassette selection screen: (A) of FIG. 11 is a diagram illustrating the entire use cassette selection screen; and (B) of FIG. 11 is a diagram illustrating a selected imaging order display region.

FIG. 12 is a diagram illustrating the relation between various kinds of information after the use cassette is selected.

FIG. 13 is a functional block diagram illustrating each unit for implementing an electronic cassette search function.

FIG. 36 is a diagram illustrating a camera image according to a sixth embodiment: (A) of FIG. 36 illustrates a camera image before a field of view is changed; and (B) of FIG. 36 illustrates a camera image after the field of view is changed.

FIG. 38 is a diagram illustrating an aspect using status information in a seventh embodiment.

FIG. 39 is a diagram illustrating long-length imaging according to an eighth embodiment: (A) of FIG. 39 illustrates the actual usage of the electronic cassettes; and (B) of FIG. 39 illustrates a camera image.

FIG. 41 is a diagram illustrating an example in which a camera is provided in a treatment cart in a ninth embodiment.

DESCRIPTION OF THE PREFERRED EMBODIMENTS

First Embodiment

Figure 1:
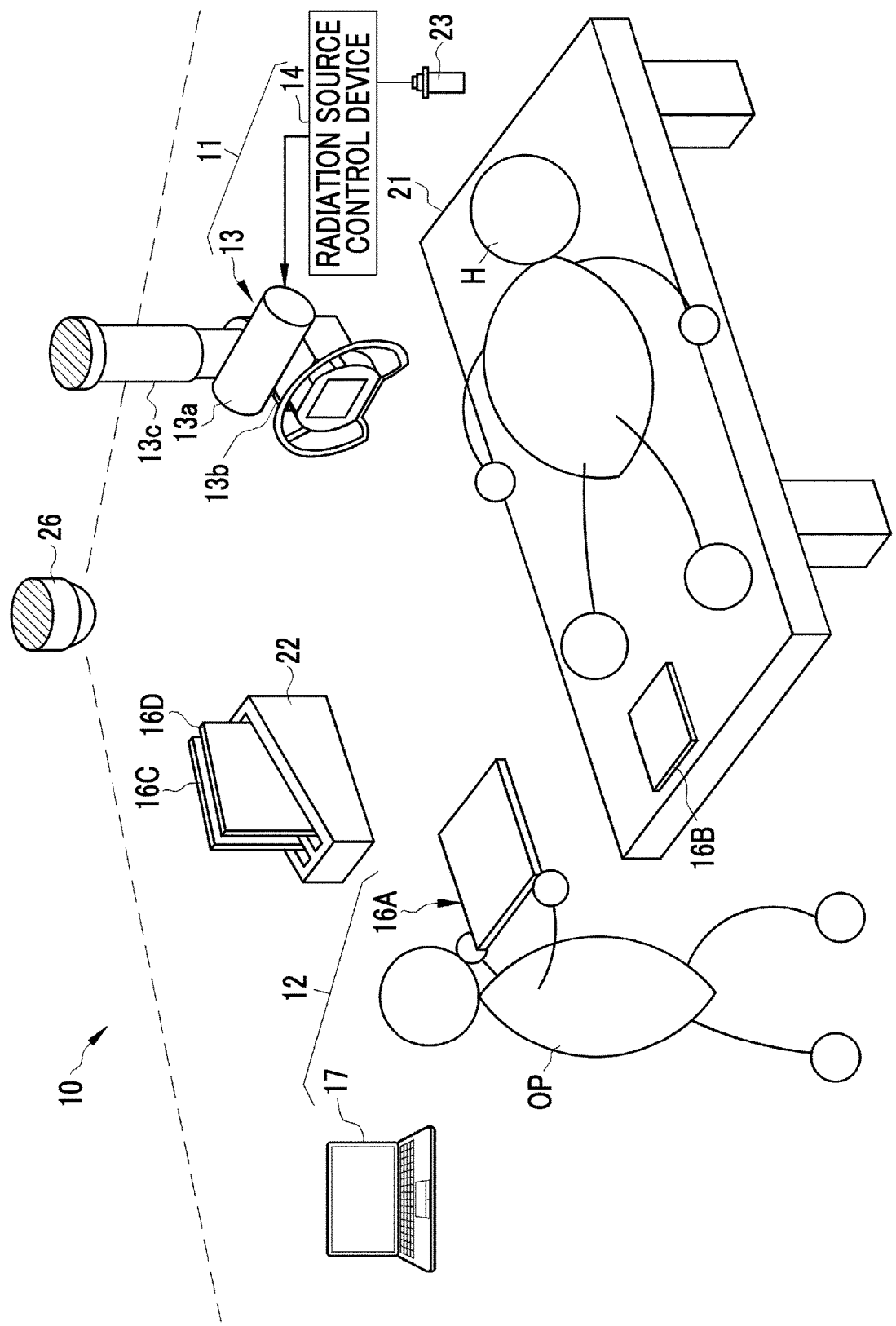
FIG. 1 is a diagram schematically illustrating the configuration of an X-ray imaging system.

In FIG. 1, an X-ray imaging system 10 that uses X-rays as radiation includes an X-ray generation apparatus 11, an X-ray imaging apparatus 12, and a camera 26. The X-ray generation apparatus 11 includes an X-ray source 13 corresponding to a radiation source and a radiation source control device 14 that controls the X-ray source 13. The X-ray imaging apparatus 12 includes an electronic cassette 16 and a console 17.

FIG. 1 illustrates an aspect in which X-ray imaging is performed for a subject H that lies on a bed 21 using the electronic cassette 16 in an imaging room in which the X-ray imaging system 10 is installed. The electronic cassette 16 is placed on, for example, the bed 21 or is held in the arms of the subject H depending on an imaging part and then imaging is performed. The X-ray imaging illustrated in FIG. 1 is free imaging without using an imaging stand.

The imaging room is equipped with an upright imaging stand (not illustrated) or a decubitus imaging stand (not illustrated) on which the electronic cassette 16 is placed in addition to the bed 21. In addition, for the electronic cassette 16, a plurality of electronic cassettes 16 having different sizes or purposes are provided. FIG. 1 illustrates, for example, an electronic cassette 16A carried by an operator OP, such as a radiology technician, that performs an imaging operation, an electronic cassette 16B that is placed on the bed 21, and electronic cassettes 16C and 16D that are accommodated in a cradle 22 with a charging function.

Hereinafter, in a case in which the electronic cassettes 16A to 16D need to be distinguished from each other, the electronic cassettes are denoted by combinations of number "16" and subdivision codes such as alphabets "A" to "D". In a case in which the electronic cassettes 16A to 16D do not need to be distinguished from each other, the electronic cassettes are denoted by only number "16" without a subdivision such as an alphabet.

The camera 26 is an optical camera that captures a usage environment in which the electronic cassette 16 is used. The usage environment includes an imaging place in which the subject H is present and the periphery of the imaging place.

The camera 26 is attached to the ceiling of the imaging room, captures an image of the imaging room from the upper side, and has the field of view in which substantially the entire area of the imaging room is included as an imaging range. In order to widen the field of view, for example, the following camera is used as the camera 26: a camera that can rotate a lens 360° to change the field of view; or a camera including a wide-angle lens such as a fish-eye lens. As such, since the imaging range of the camera 26 includes the entire area of the imaging room, a plurality of electronic cassettes 16A and 16D which are scattered in the imaging room can be included in the field of view.

The camera 26 outputs, for example, a camera image 76 (see FIG. 14) which is an optical image indicating a captured usage environment. The camera image 76 is, for example, a color image and is a motion picture. The camera 26 includes a charge coupled device (CCD) image sensor or a complementary metal-oxide-semiconductor (CMOS) image sensor and outputs the captured camera image 76 as digital data. The camera 26 is connected to a network, such as a local area network (LAN) which is a wired network or a wireless network, and transmits the camera image 76 to the console 17 through the network. The camera image 76 is used in a case in which the console 17 performs a function of searching for the electronic cassette 16 as described below.

The X-ray source 13 includes an X-ray tube 13a that emits X-rays and an irradiation field limiter (collimator) 13b that limits the irradiation field of the X-rays emitted from the X-ray tube 13a. In this example, the X-ray source 13 is a fixed type that is fixed to the ceiling of the imaging room. The position of the X-ray source 13 in the horizontal direction can be moved by an overhead traveling device (not illustrated) and the height of the X-ray source 13 is adjusted by expanding or contracting a support 13c of the X-ray source 13.

The X-ray tube 13a includes a filament that emits thermal electrons and a target that collides with the thermal electrons emitted from the filament and emits X-rays. The irradiation field limiter 13b has, for example, a structure in which four lead plates that shield X-rays are provided on each side of a rectangle and a rectangular irradiation opening which transmits X-rays is provided at the center. The irradiation field limiter 13b moves the positions of the lead plates to change the size of the irradiation opening, thereby limiting the irradiation field.

The radiation source control device 14 includes a high voltage generator that supplies a high voltage to the X-ray source 13 and a controller that controls a tube voltage for determining an energy spectrum of the X-rays emitted from the X-ray source 13, a tube current for determining the amount of radiation emitted per unit time, and an X-ray irradiation time. The high voltage generator increases an input voltage using a transformer to generate a high tube voltage and supplies driving power to the X-ray source 13 through a high-voltage cable. The irradiation conditions, such as the tube voltage, the tube current, and the irradiation time, are manually set by the operator OP through an operation panel of the radiation source control device 14. In addition, the irradiation conditions are set by communication with the X-ray imaging apparatus 12.

An irradiation switch 23 is connected to the radiation source control device 14 through a signal cable. The irradiation switch 23 is operated by the operator OP. The irradiation switch 23 is pressed in two stages. In a case in which the irradiation switch 23 is pressed to the first stage, the radiation source control device 14 starts to warm up the X-ray source 13. In a case in which the irradiation switch 23 is pressed to the second stage, the radiation source control device 14 directs the X-ray source 13 to start to emit X-rays. The radiation source control device 14 includes a timer and operates the timer to measure the X-ray emission time. In a case in which the irradiation time set in the irradiation conditions elapses, the radiation source control device 14 stops the emission of X-rays.

Figure 2:
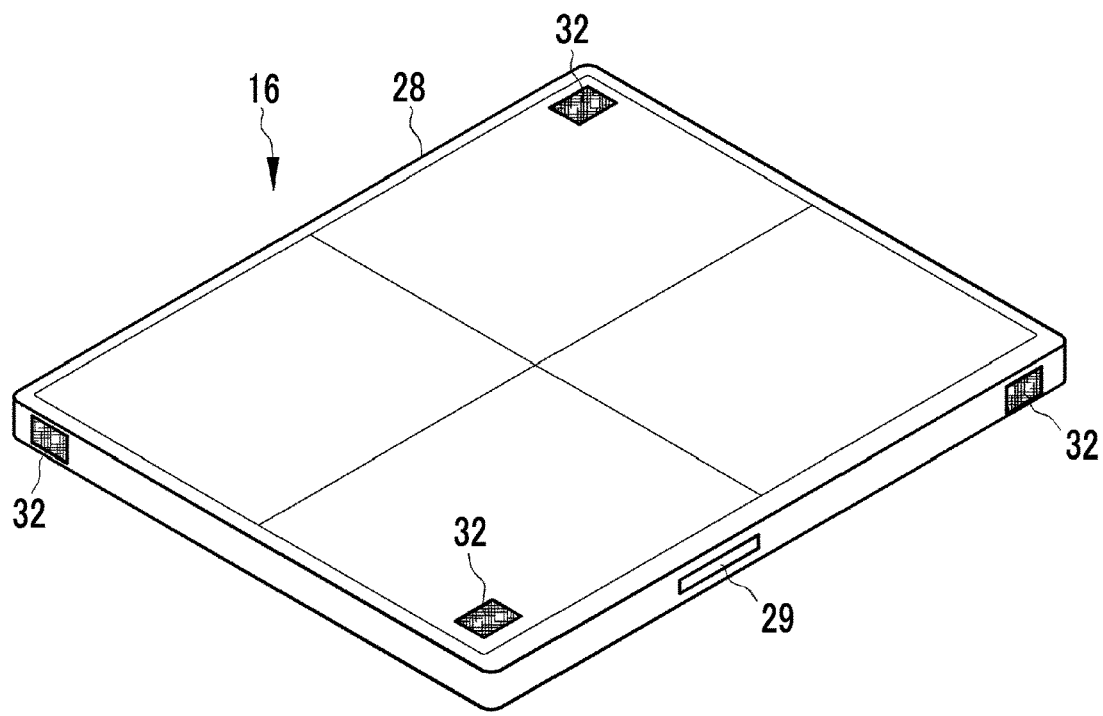
FIG. 2 is a perspective view illustrating a front surface side of an electronic cassette.
Figure 3:
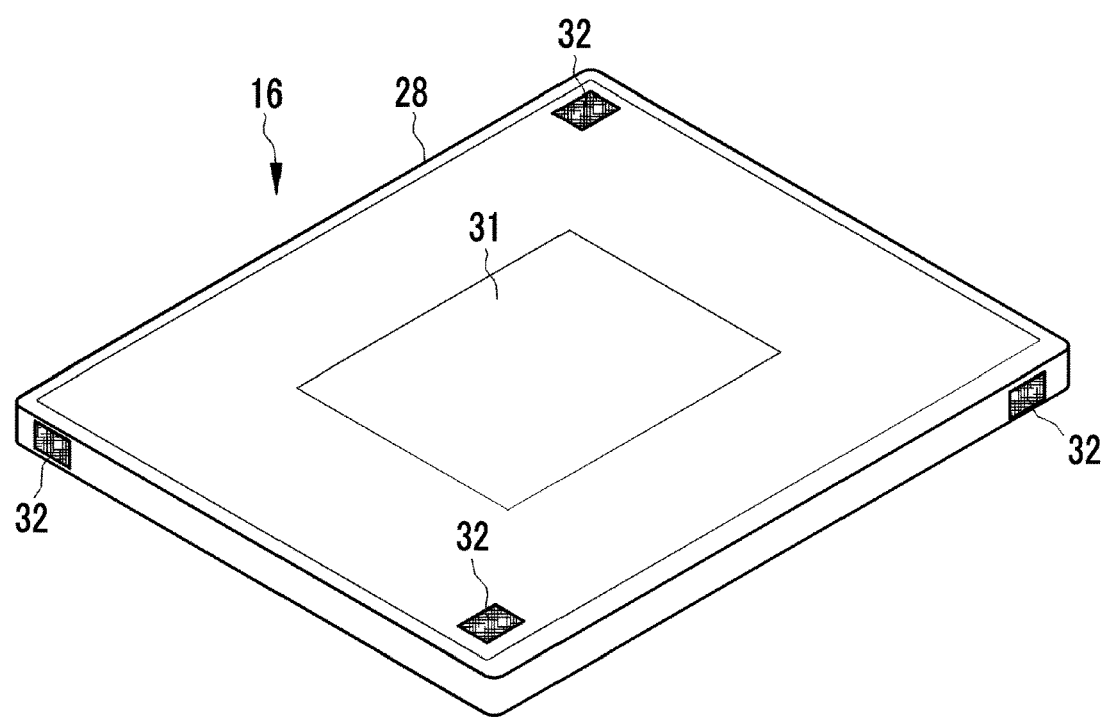
FIG. 3 is a perspective view illustrating a rear surface side of the electronic cassette.

As illustrated in FIGS. 2 and 3, the electronic cassette 16 includes a sensor panel (not illustrated) and a housing 28 that accommodates the sensor panel. The electronic cassette 16 is a portable X-ray image detection device which receives X-rays which have been emitted from the X-ray source 13 and then transmitted through the subject H and detects an X-ray image of the subject H based on the X-rays.

The sensor panel includes, for example, a scintillator and an optical detection substrate. The scintillator is a phosphor that converts X-rays into visible light. The optical detection substrate is a substrate in which a plurality of pixels that convert the visible light emitted from the scintillator into an electric signal and accumulate charge are two-dimensionally arranged. In addition, a direct-conversion-type sensor panel that directly converts X-rays into charge, without using a scintillator, may be used.

The electronic cassette 16 performs an image detection operation of detecting an X-ray image in synchronization with the emission of the X-rays from the X-ray source 13. As a synchronization method, a control signal for controlling an operation time is transmitted between the electronic cassette 16 and the X-ray generation apparatus 11 through the console 17 by communication to control the operation time. Alternatively, in a case in which the electronic cassette 16 has an irradiation start detection function of automatically detecting the start of the emission of X-rays, the irradiation start detection function is used to control the operation time. In a case in which the irradiation start detection function is used, the transmission of the control signal between the electronic cassette 16 and the X-ray generation apparatus 11 by communication is not required.

The housing 28 is, for example, made of stainless steel and a transmission plate that transmits X-rays is provided on a front surface of the housing 28 illustrated in FIG. 2. The housing 28 is a flat plate and has a substantially rectangular shape in a plan view. The electronic cassette 16 is a wireless type that can wirelessly communicate with the console 17. A communication unit 29 that communicates with the console 17 is provided in the housing 28 of the electronic cassette 16. The communication unit 29 includes a wired communication unit using a communication cable and a wireless communication unit that performs communication with radio waves.

As illustrated in FIG. 3, a battery 31 that supplies power to the sensor panel or the communication unit 29 is provided on a rear surface of the electronic cassette 16. The electronic cassette 16 can be driven by a battery in addition to a commercial power supply using a power cable.

Cassette identification data (ID) which is identification information for identifying the electronic cassette 16 is recorded on a memory (not illustrated) provided in the electronic cassette 16. The cassette ID is uniquely allocated to each electronic cassette 16. The cassette ID is, for example, a character string including symbols or numbers. In a case in which the console 17 and the electronic cassette 16 communicate with each other, the cassette ID is added to communication data. In a case in which the console 17 transmits a control signal to the electronic cassette 16, the console 17 adds the cassette ID to the control signal to specify the electronic cassette 16 which is a transmission destination. In addition, in a case in which the console 17 receives an X-ray image from the electronic cassette 16, the console 17 reads the cassette ID from the accessory information of the X-ray image and specifies the electronic cassette 16 which is the transmission source of the X-ray image.

A plurality of ID markers 32 are provided on an outer surface of the housing 28. The cassette ID is recorded on the ID marker 32. The cassette ID is the same as the cassette ID recorded on the memory (not illustrated) of the electronic cassette 16. In the X-ray imaging system 10, the cassette ID recorded on the ID marker 32 is used for the function of searching for the electronic cassette 16 using the camera image 76, which will be described below.

For example, the cassette ID is recorded in the form of a one-dimensional bar code or a two-dimensional bar code on the ID marker 32. A character string of the cassette ID may be recorded without any change. The ID marker 32 is provided on the outer surface of the housing 28 such that it can be recognized in the camera image 76. In this example, two ID markers 32 are provided on a diagonal line in each of the front surface of the housing 28 on which X-rays are incident and the rear surface opposite to the front surface. In addition, one ID marker 32 is provided on each of four side surfaces. Since the ID markers 32 are provided at a plurality of positions of the housing 28, the ID markers 32 are likely to be included in the camera image 76. Therefore, the probability that the ID markers 32 will be detected from the camera image 76 increases.

Here, the outer surface of the housing 28 includes the front and rear surfaces of the housing 28 and the side surfaces connected to both the front surface and the rear surface. At least a portion of the side surface may be curved. In addition, the side surfaces and the front and rear surfaces may be connected to each other, without a chamfer or a seam at the boundaries therebetween. In a case in which the ID marker 32 is provided on the front surface of the housing 28, it is preferable to dispose the ID marker 32 outside an imaging region in order to prevent the ID marker 32 from being included in the X-ray image. The ID marker 32 may be provided in the imaging region. In this case, it is preferable that the ID marker 32 is made of a material that is not included in the X-ray image.

The imaging region of the electronic cassette 16 has various sizes, such as a 14×17 rectangular size, a 17×17 square size, and a 10×12 rectangular size. In FIG. 1, for example, the electronic cassettes 16A and 16C are a 14×17 type, the electronic cassette 16B is a 10×12 type, and the electronic cassette 16D is a 17×17 type. The electronic cassettes 16A to 16D with different sizes are used for the purpose.

Some electronic cassettes 16 are used for free imaging as illustrated in FIG. 1 and some electronic cassettes 16 are placed on an upright imaging stand or a decubitus imaging stand and are then used. In general, a plurality of different electronic cassettes 16 that are used for various purposes are present in the imaging room.

In a case in which the electronic cassette 16 is used for imaging, the electronic cassette 16 needs to communicate with the console 17, unlike a film cassette or an imaging plate (IP) cassette. Therefore, the operator OP selects the electronic cassette 16 to be used for X-ray imaging as a use cassette before performing X-ray imaging. The use cassette is selected by the console 17. As described above, in a case in which the use cassette is selected, the console 17 communicates with the selected use cassette to transmit various kinds of control information to the use cassette or to receive the X-ray image from the use cassette. The operation of the console 17 selecting the use cassette is referred to as, for example, pairing.

In a case in which the electronic cassette 16 is wirelessly connected to the console 17, a communication cable is not required. Therefore, in a case in which a plurality of electronic cassettes 16 are present in the usage environment as illustrated in FIG. 1, it is difficult to check which of the electronic cassettes 16 is the use cassette paired with the console 17 at a glance. The console 17 has a search function of recognizing the ID markers 32 with the camera image 76 to search for the use cassette. The ID markers 32 are used for the search function.

Figure 4:
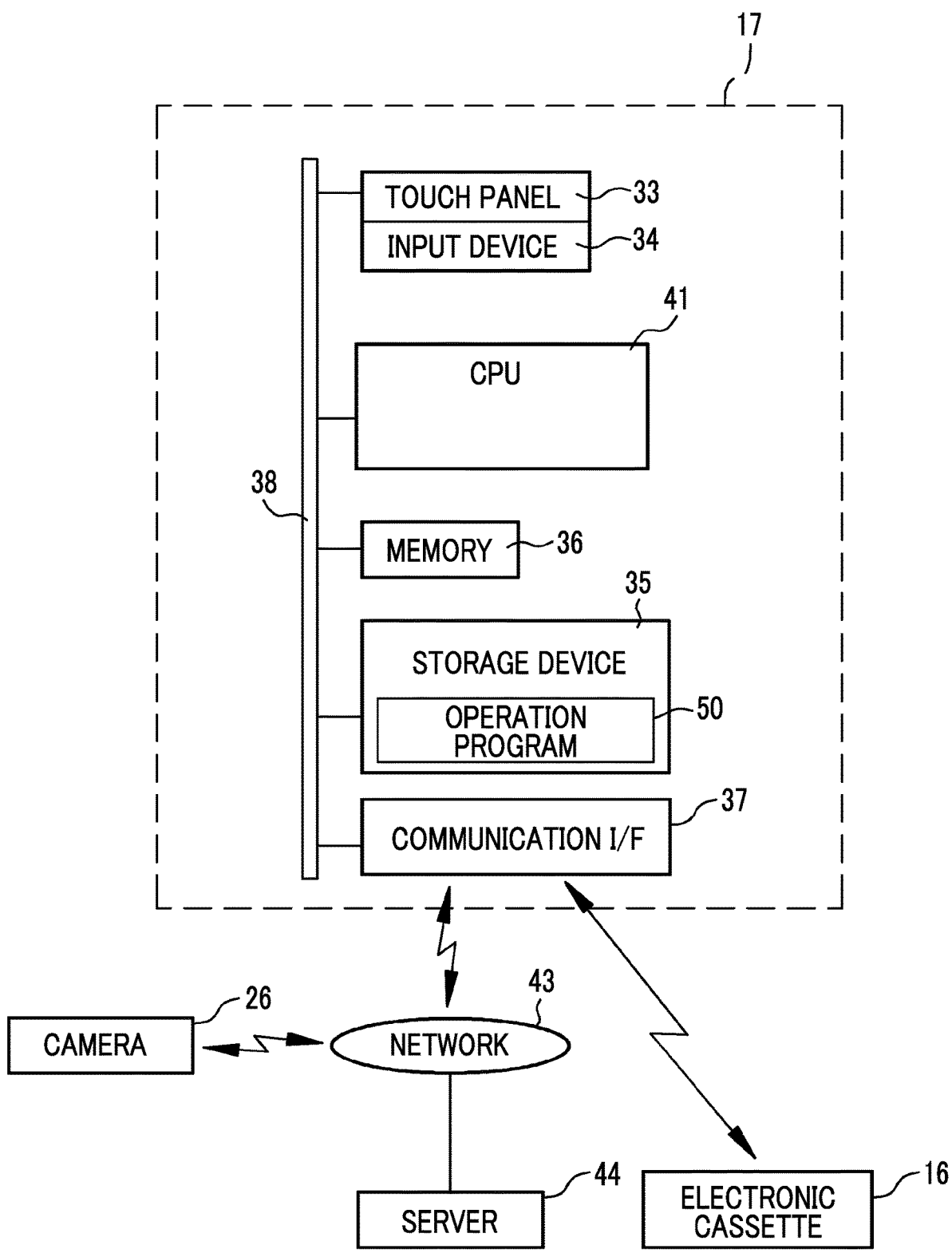
FIG. 4 is a block diagram schematically illustrating the electrical configuration of a console.

In FIG. 4, the console 17 is implemented by installing, for example, an operation program 50 for a console in a notebook personal computer. The console 17 includes a touch panel 33, an input device 34, a storage device 35, a memory 36, a central processing unit (CPU) 41, and a communication interface (I/F) 37. These units are connected to each other through a data bus 38. The touch panel 33 functions as an input device that receives an operation command input by a touch operation and functions as a display unit that displays various kinds of information.

The storage device 35 is, for example, a hard disk drive provided in the console 17. In addition, the storage device 35 may be an external device or a network storage that can be accessed through a network. The storage device 35 stores a control program, such as an operating system, various application programs, and various kinds of data associated with the programs. The application programs include the operation program 50 that causes a notebook personal computer to function as the console 17.

The memory 36 is a work memory that is used by the CPU 41 to perform processes. The CPU 41 loads a program stored in the storage device 35 to the memory 36 and executes a process based on the program to control the overall operation of each unit of the console 17. The communication I/F 37 performs communication with the electronic cassette 16 or a network 43. The network 43 is, for example, a LAN installed in a hospital including the imaging room. The console 17 is connected to various servers 44 and the camera 26 in the hospital through the network 43 so as to communicate therewith. The console 17 receives the camera image 76 from the camera 26 through the network 43 and receives an X-ray imaging order from the server 44.

The basic functions of the console 17 will be described with reference to FIGS. 5 to 12. The basic functions of the console 17 include, for example, a display function of displaying the imaging order or the X-ray image received from the electronic cassette 16 on the touch panel 33 which is a display unit, an image processing function of processing the X-ray image, and a cassette control function of controlling the electronic cassette 16.

As illustrated in FIG. 5, in a case in which the operation program 50 is run, the CPU 41 functions as a graphical user interface (GUI) controller 51, a cassette controller 52, an X-ray image processing unit 53, a network communication unit 54, and a search processing unit 55 in cooperation with the memory 36. The GUI controller 51 is a display controller that performs control for displaying various kinds of information, such as the X-ray image captured by the electronic cassette 16 and an operation screen generated by a GUI, on the touch panel 33. In addition, the GUI controller 51 functions as an input controller that receives operation commands input from the input device 34 or the touch panel 33 in cooperation with the operation screen.

Figure 9:
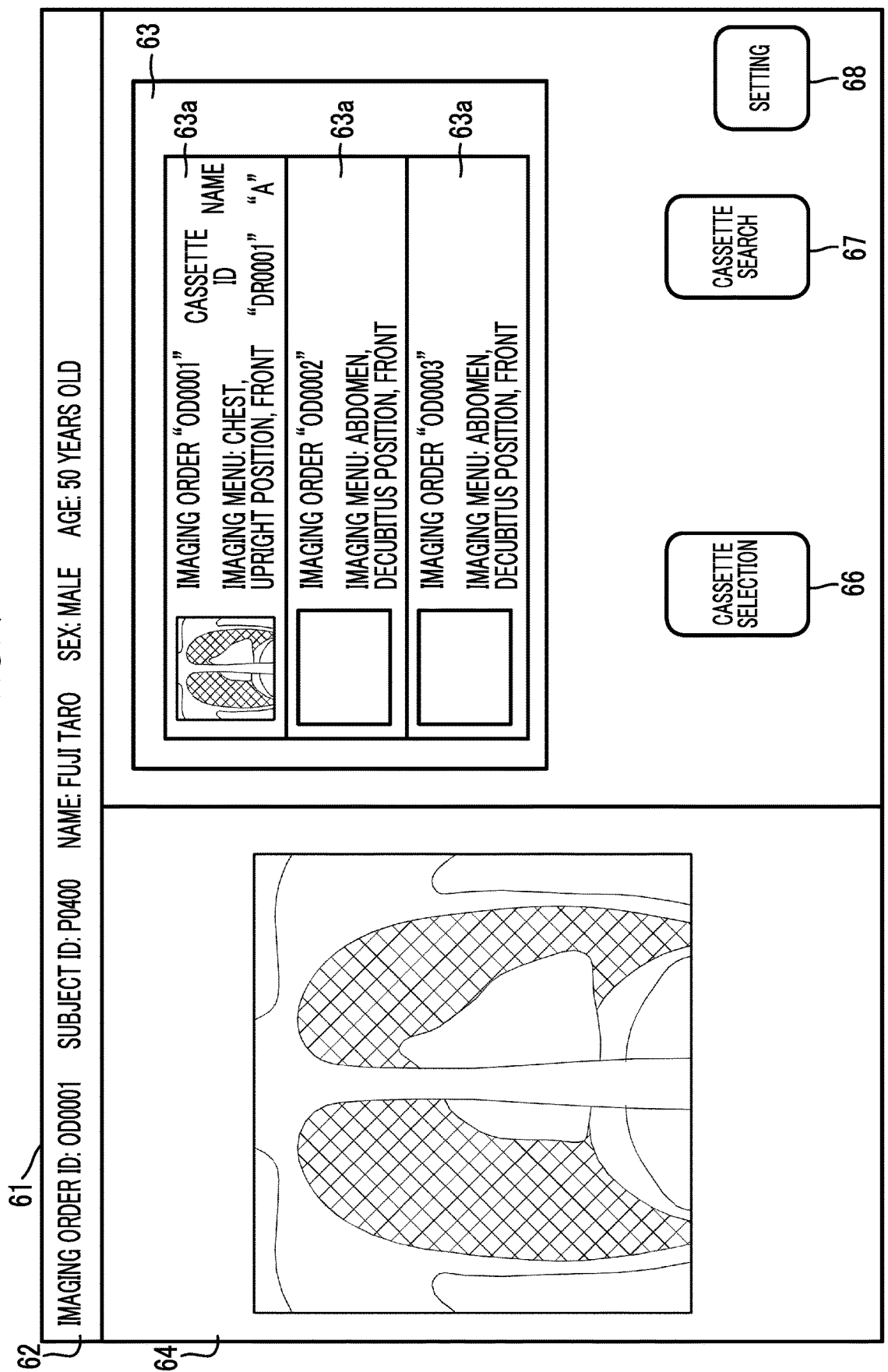
FIG. 9 is a diagram illustrating an imaging order display screen.
Figure 10:
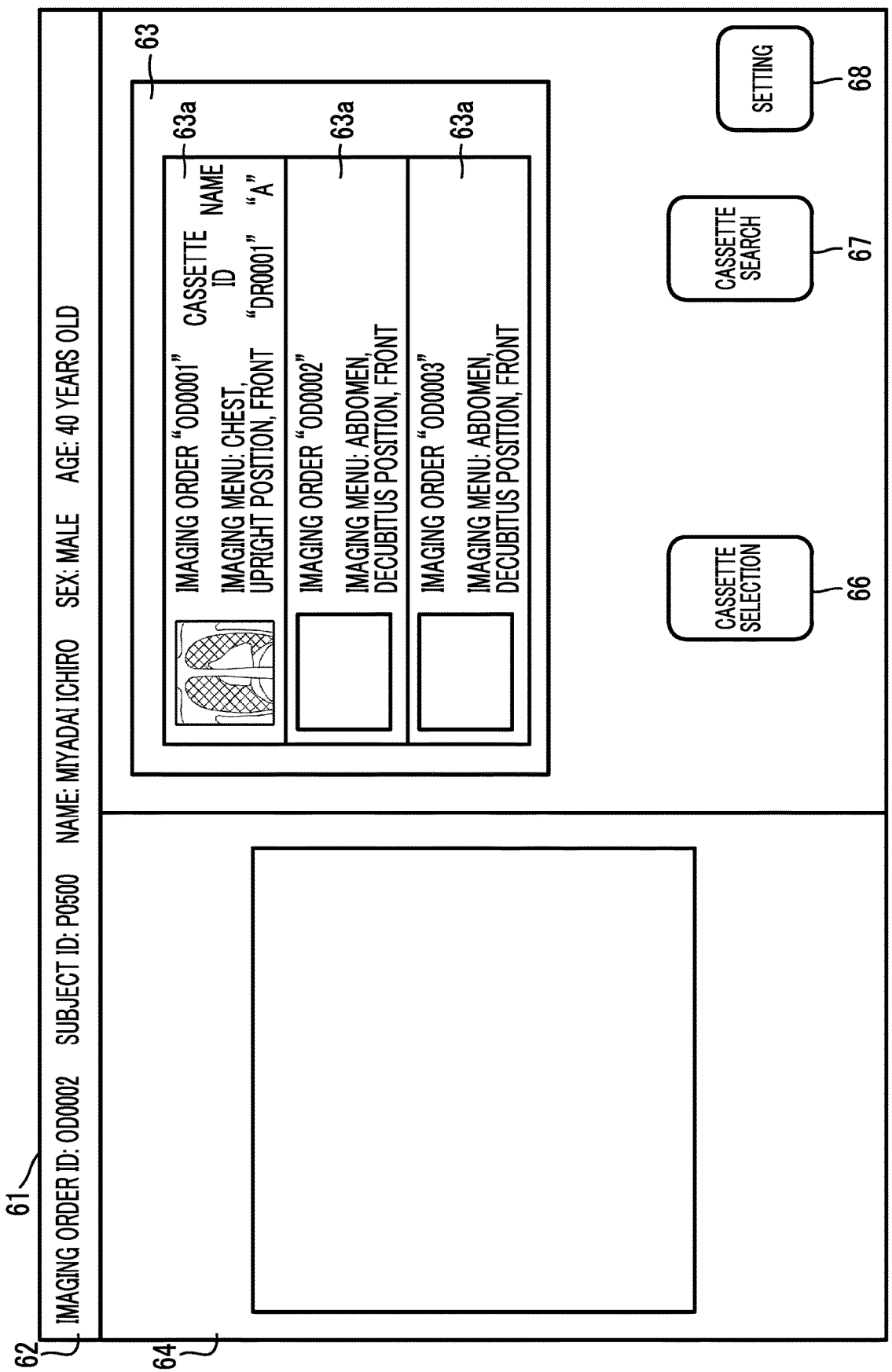
FIG. 10 is a diagram illustrating another example of the imaging order display screen.

The storage device 35 stores the information of the operation screen illustrated in, for example, FIG. 9 or FIG. 10. The GUI controller 51 accesses the storage device 35, reads the information of the operation screen, and generates an operation screen to be output to the touch panel 33.

The cassette controller 52 communicates with the electronic cassette 16 through the communication I/F 37 to control the electronic cassette 16. The cassette controller 52 transmits a command to turn on or off the electronic cassette 16, a command to switch the mode to a power saving mode and an imaging preparation state (ready status), and various kinds of cassette control information, such as the irradiation conditions, received from the GUI controller 51 to the electronic cassette 16.

A plurality of electronic cassettes 16 that can be controlled by the console 17 are registered in the console 17 in advance. The registration information is stored as registered cassette information 57 in the storage device 35. As illustrated in FIG. 6, a cassette ID, a name, a plane size, a communication address, and specification information are recorded in the registered cassette information 57. The specification information includes, for example, the correction information of each electronic cassette 16 used to correct the X-ray image.

The correction information includes, for example, offset data used to correct a dark current and defective pixel data related to the defects of pixels in the sensor panel. In the registered cassette information 57 illustrated in FIG. 6, five electronic cassettes 16 with cassette IDs "DR0001" to "DR0005" are registered. Cassettes A to D corresponding to the cassette IDs "DR0001" to "DR0004" correspond to the electronic cassettes 16A to 16D, respectively. The use cassette used for X-ray imaging is selected from the registered cassettes which are the electronic cassettes 16 registered in the registered cassette information 57.

The information of the electronic cassette 16 which has been selected from the registered cassettes by the operator OP and then set as the use cassette by the console 17 is recorded in the use cassette setting information 58 illustrated in FIG. 7. The use cassette setting information 58 includes a setting information item, a status item, and an imaging order item, in addition to a cassette ID and a name which are the same as those in the registered cassette information 57. The setting information is information indicating whether the electronic cassette has been set as the use cassette. In a case in which the electronic cassette has been set as the use cassette, "set" is written in the setting information item. In a case in which the electronic cassette has not been set as the use cassette, "unset" is written in the setting information item.

Status information indicating the operating state of the electronic cassette 16 which has been set as the use cassette is recorded in the status item. Examples of the status include a ready status in which preparation for imaging has been completed and a sleep status in which the electronic cassette is on standby and is in a power saving mode. In a case in which the use cassette has been set, the cassette controller 52 communicates with the electronic cassette 16 set as the use cassette and monitors the status of the use cassette. Then, the cassette controller 52 records the status information of the use cassette in the use cassette setting information 58. The cassette controller 52 controls the status of the use cassette and updates the status information at any time with a change in the status of the use cassette.

The imaging order item indicates an imaging order corresponding to the X-ray imaging performed using the use cassette. An order ID of the imaging order corresponding to the use cassette is recorded in the imaging order item (see FIG. 12). In a case in which the X-ray imaging using the use cassette has been completed, the information of the imaging order in the use cassette setting information 58 is cleared. FIG. 7 illustrates a state in which no electronic cassettes 16 are set as the use cassette.

FIG. 8 illustrates an example of imaging order information 59. The imaging order is, for example, imaging request information that is issued from a diagnosis and treatment department, such as a surgery department or an internal department in which X-ray imaging is performed, to a radiology department and includes items such as an order ID, a subject ID (patient ID), and an imaging menu. The imaging menu includes an imaging part, such as the chest or the abdomen, an imaging posture, such as an upright position or a decubitus position, and information for designating the imaging procedure of X-ray imaging including an imaging direction, such as the front or the rear.

In addition to the above-mentioned items, a subject information item (not illustrated) indicating the name, sex, age, height, and weight of the subject H is included in the imaging order information 59. In addition, the imaging order information 59 includes items, such as a diagnosis and treatment department to which a person who requests imaging belongs, the ID of the person who requests imaging, a receiving date and time, the purpose of imaging, such as the monitoring of conditions after the surgery or the determination of the effect of treatment remedies, and orders issued from the person who requests imaging to the operator OP.

In addition, the imaging order information 59 includes a completion information item and a use cassette item for each imaging order. The completion information is information about whether X-ray imaging has been completed. In a case in which imaging has been completed, "imaging completed" is recorded in the completion information item. In a case in which imaging has not been completed, "uncompleted" is recorded in the completion information item. The cassette ID of the use cassette used for X-ray imaging is recorded in the use cassette item. In this example, for an imaging order "OD0001", imaging has been completed and the cassette ID "DR0001" of the use cassette is recorded.

The console 17 acquires the imaging order from the server 44 that forms a hospital information system (HIS) or a radiation information system (RIS) and registers the imaging order in the imaging order information 59. In addition, the imaging order may be directly input by the operator OP through the console 17 and then registered, instead of being acquired from the server 44. In a case in which X-ray imaging for each imaging order has been completed, the data of the X-ray images corresponding to each imaging order is recorded in the imaging order information 59 so as to be associated with each imaging order.

Returning to FIG. 5, the cassette controller 52 specifies the cassette ID of the use cassette with reference to the use cassette setting information 58 and communicates with the specified use cassette. The cassette controller 52 receives the data of the X-ray image from the use cassette and transmits the received X-ray image to the X-ray image processing unit 53. As described above, for example, the cassette controller 52 controls or monitors the status of the use cassette.

The X-ray image processing unit 53 performs various types of image processing, such as offset correction, defect correction, sharpness correction, and frequency processing, for the X-ray image. Instead of the console 17, the electronic cassette 16 may perform some of the various types of image processing for the X-ray image, for example, offset correction and defect correction. The X-ray image subjected to the image processing in the X-ray image processing unit 53 is stored in, for example, the storage device 35 of the console 17, is transmitted to an image storage server, such as a picture archiving and communication system (PACS) server, and is then stored in the server.

The network communication unit 54 communicates with the server 44 through the communication I/F 37 and the network 43 and receives the imaging order from the RIS or the HIS or transmits the X-ray image to the image storage server such as a picture archiving and communication system (PACS) server. In addition, the network communication unit 54 functions as a camera image acquisition unit that acquires the camera image 76 from the camera 26. The functions of the search processing unit 55 will be described below.

An imaging order display screen 61 and a use cassette selection operation will be described with reference to FIGS. 9 to 12. The imaging order display screen 61 illustrated in FIGS. 9 and 10 is an operation screen that is output to the touch panel 33 by the GUI controller 51.

The imaging order display screen 61 includes a patient information display region 62 in which patient information including the ID of the imaging order and the name, ID, sex, and age of a patient is displayed, an imaging order display region 63 in which the imaging orders registered in the console 17 are displayed, and an image display region 64 in which a captured X-ray image is displayed. A cassette selection button 66 for selecting the use cassette used for imaging from the registered cassettes is provided below the imaging order display region 63. Reference numeral 67 indicates an operation button for issuing a cassette search command and reference numeral 68 indicates a setting button for various settings.

In a case in which there are a plurality of imaging orders, the plurality of imaging orders are displayed in a list form in the imaging order display region 63. In this example, the imaging order display region 63 includes three imaging orders illustrated in FIG. 9. The imaging orders are displayed in the imaging order display region 63 on the basis of the imaging order information 59 illustrated in FIG. 8. Information for designating the imaging procedure of each imaging order, such as "the chest, an upright position, and the front" is displayed in each imaging order display field 63a of the imaging order display region 63.

In a case in which an operation of clicking a mouse of the input device 34 or a touch operation through the touch panel 33 is performed for one display field 63a, an imaging order corresponding to the display field 63a is designated. The display field 63a of the designated imaging order is highlighted (hatched) so as to be distinguished from the other imaging orders which are not designated. This example shows a state in which the imaging order "OD0001" is designated.

A thumbnail image which is a minified image of the captured image is displayed at the left end of the display field 63a corresponding to the processed (captured) imaging order. No thumbnail images are displayed in the display fields 63a corresponding to the unprocessed imaging orders. This example shows a state in which the imaging order "OD0001" has been processed, a thumbnail image is displayed in the display field 63a corresponding to the processed imaging order, the other two imaging orders have not been processed, and no thumbnail images are displayed in the display fields 63a corresponding to the unprocessed imaging orders.

A captured X-ray image of the imaging order selected in the imaging order display region 63 is displayed in the image display region 64. In this example, an X-ray image corresponding to the imaging order "OD0001" is displayed. Of course, an image selected from a plurality of captured X-ray images may be displayed in the image display region 64.

For example, a selection operation (also referred to as a pairing operation) of selecting the electronic cassette 16 to be used for X-ray imaging corresponding to the unprocessed imaging order is performed as follows. First, as illustrated in FIG. 10, an unprocessed imaging order "OD0002" is selected in the imaging order display region 63. In this state, in a case in which the cassette selection button 66 is operated, as illustrated in (A) and (B) of FIG. 11, a use cassette selection screen 69 is displayed on the touch panel 33. The registered cassette information 57 is displayed on the use cassette selection screen 69.

The operator OP determines which of the electronic cassette 16 is suitable for X-ray imaging corresponding to the imaging order on the basis of the content of the imaging order and selects an electronic cassette 16 to be used for X-ray imaging from the registered cassettes. The selection operation is performed by a touch operation or a mouse click operation. (A) of FIG. 11 illustrates a state in which a cassette C with a cassette ID "DR0003" is selected as represented by hatching. In a case in which the selection operation is performed in this way, the console 17 sets the selected electronic cassette 16 as the use cassette and updates the use cassette setting information 58.

In a case in which the use cassette is set as illustrated in (B) of FIG. 11, the cassette ID ("DR0003") and name "C" of the set use cassette are displayed in the display field 63a of the imaging order display region 63.

In a case in which the use cassette is set as illustrated in FIG. 12, the use cassette is associated between the registered cassette information 57 and the use cassette setting information 58. The order ID ("OD0002") is registered for the set use cassette in the use cassette setting information 58 and is associated between the use cassette setting information 58 and the imaging order information 59.

Here, in order to distinguish the cassette ID of the use cassette set in the console 17 from the cassette ID recorded on the memory of the electronic cassette 16 or the ID marker 32, the cassette ID recorded on the memory of the electronic cassette 16 or the ID markers 32 is referred to as a first cassette ID and the cassette ID set in the console 17 is referred to as a second cassette ID. The second cassette ID corresponds to second identification information and the first cassette ID corresponds to first identification information.

The function of the console 17 searching for the electronic cassette 16 using the camera 26 will be described with reference to FIGS. 13 to 19. In FIG. 13, the network communication unit 54 acquires the camera image 76 captured by the camera 26 through the network 43.

Figure 14:
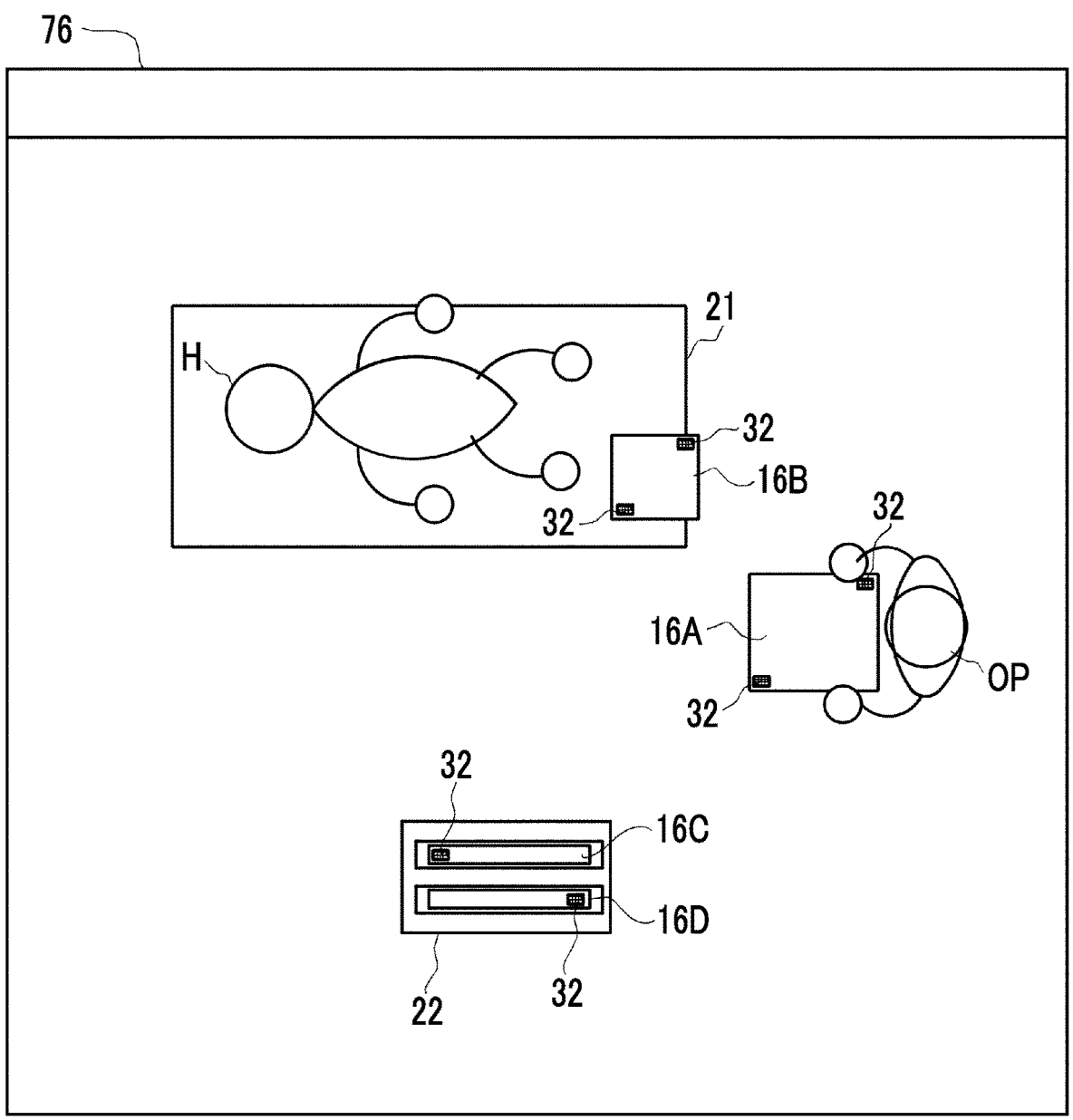
FIG. 14 is a diagram illustrating a camera image.

FIG. 14 illustrates an example of the camera image 76 captured by the camera 26. The camera image 76 includes an aspect of the inside of the imaging room including the bed 21 and the subject H as the usage environment of the electronic cassette 16. As illustrated in FIG. 1, a plurality of electronic cassettes 16A to 16D are provided in the imaging room and the camera image 76 includes the electronic cassettes 16A to 16D. The camera image 76 is displayed on the touch panel 33 which is a display unit of the console 17 under the display control of the GUI controller 51.

In FIG. 13, the search processing unit 55 includes an in-image cassette detection unit 72, an identification information acquisition unit 73, a search controller 74, and an image combination unit 75. The search controller 74 acquires, as the second identification information, the second cassette ID of the use cassette set in the console 17 as the electronic cassette 16 used for X-ray imaging with reference to the use cassette setting information 58.

Figure 15:
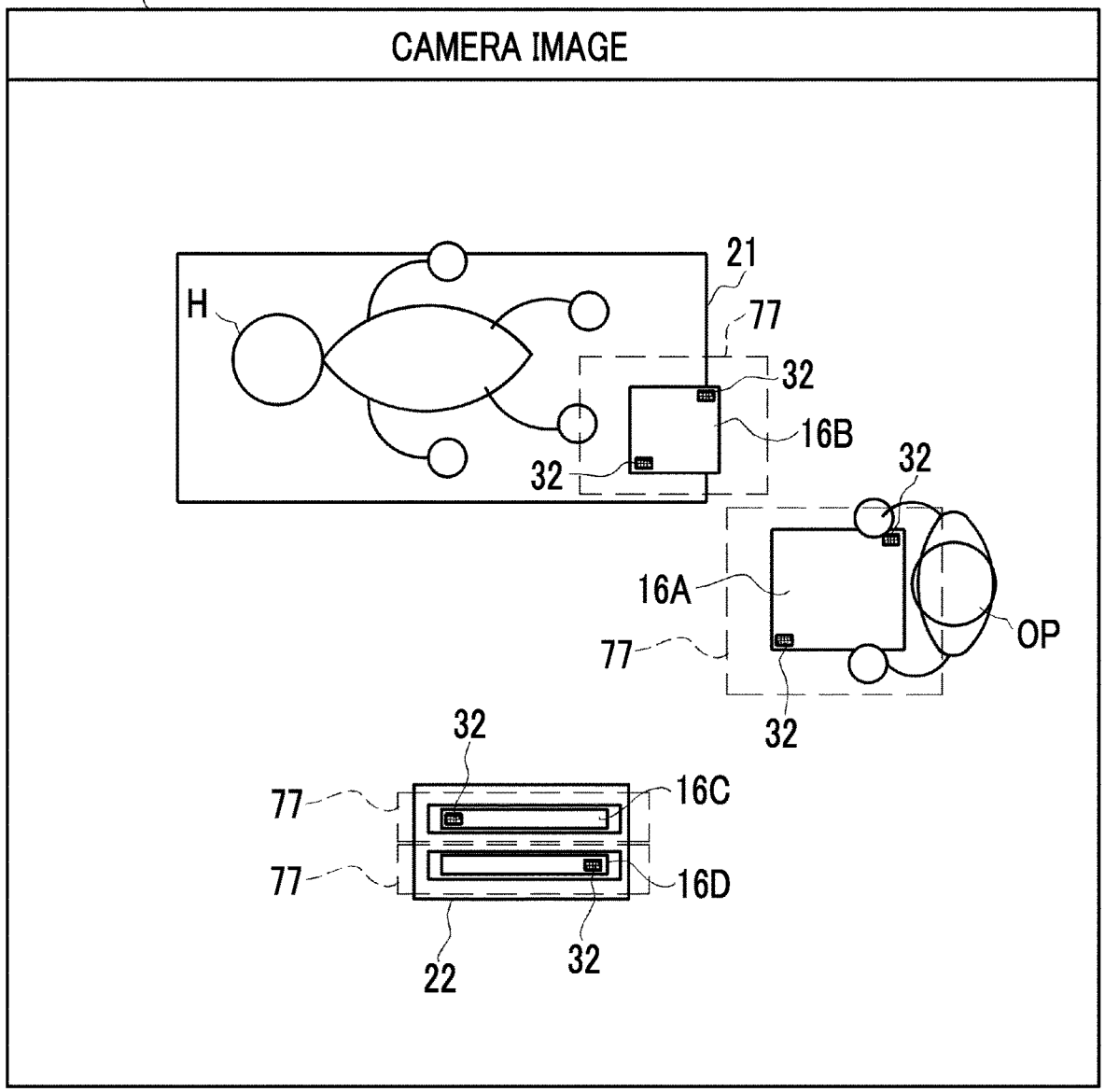
FIG. 15 is a diagram illustrating a camera image after an in-image cassette region is detected.

As illustrated in FIG. 15, the in-image cassette detection unit 72 detects an in-image cassette region 77 of the electronic cassette 16 included in the camera image 76 on the basis of the camera image 76. The in-image cassette detection unit 72 detects the electronic cassette 16 included in the camera image 76 on the basis of the camera image 76, using a known image recognition method such as pattern matching. For example, the in-image cassette detection unit 72 extracts a pattern, such as the contour of the electronic cassette 16 or the bed 21, as a feature amount from the camera image 76 and collates the extracted feature amount with the stored feature information including the contour of the electronic cassette 16. Contour information includes the planar shape of the electronic cassette 16 and the contour of the electronic cassette 16 as viewed from the side or an oblique direction. In a case in which there are features, such as colors, other than the contour of the electronic cassette 16, the collation may be performed using the feature amounts other than the contour.

The in-image cassette detection unit 72 detects a region including the detected position of the electronic cassette 16 and the periphery thereof as the in-image cassette region 77. Specifically, the in-image cassette region 77 is output as coordinate information in the camera image 76. In a case in which the camera image 76 includes a plurality of electronic cassettes 16, the in-image cassette detection unit 72 detects the in-image cassette regions 77 of all of the electronic cassettes 16. The in-image cassette detection unit 72 outputs the detected in-image cassette region 77 as a detection result to the identification information acquisition unit 73.

The identification information acquisition unit 73 detects the ID marker 32 attached to the electronic cassette 16 from the in-image cassette region 77 on the basis of the camera image 76, using a known image recognition method such as pattern matching. Similarly to the detection of the electronic cassette 16, the ID marker 32 is detected by collating the stored feature amount of the ID marker 32 with the feature amount extracted from the camera image 76.

Then, the identification information acquisition unit 73 reads the first cassette ID from the detected ID marker 32. In this way, the identification information acquisition unit 73 acquires the first cassette ID which is the first identification information. The identification information acquisition unit 73 outputs the acquired first cassette ID and the information of the in-image cassette region 77 corresponding to the first cassette ID to the search controller 74.

Figure 16:
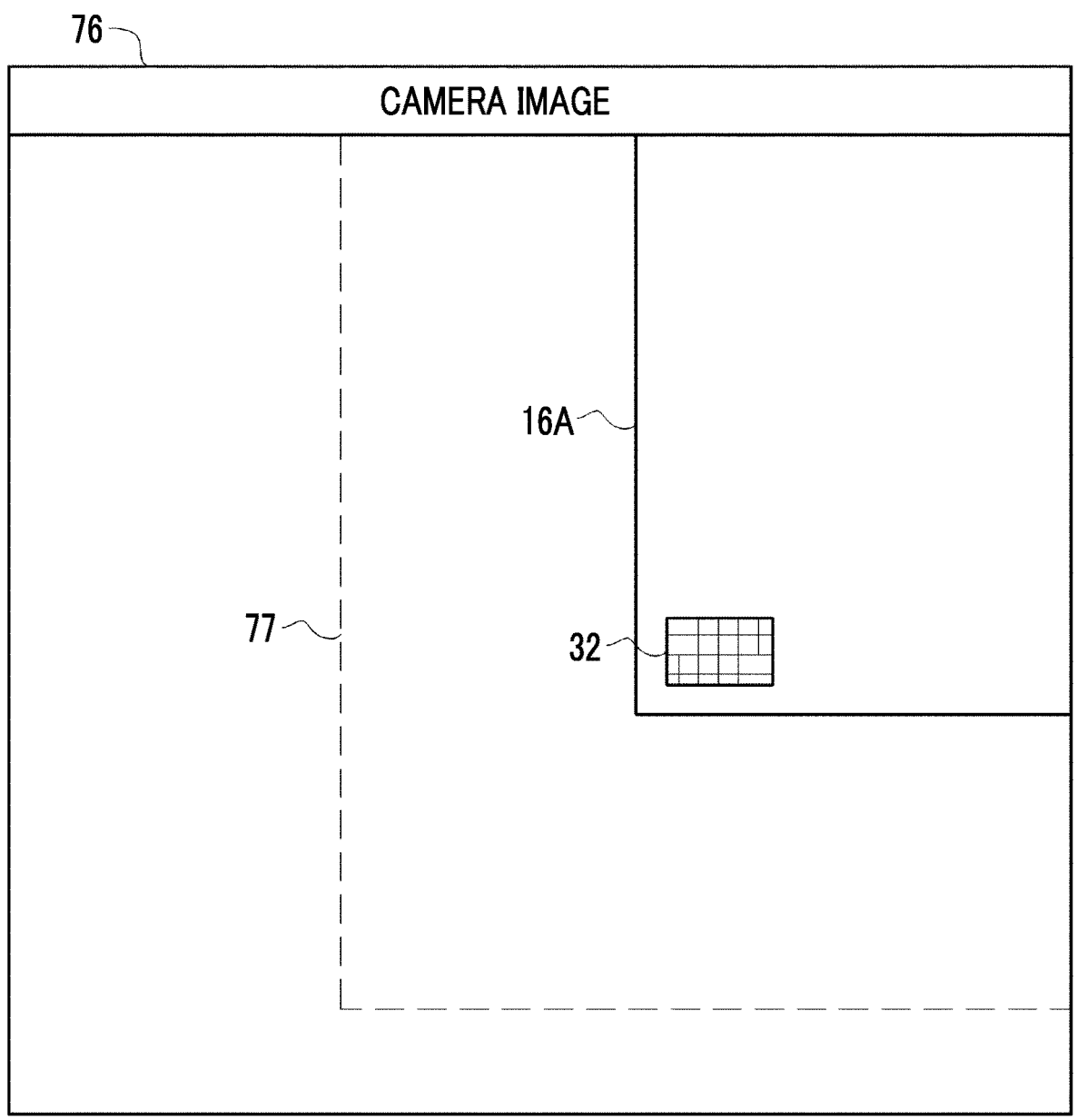
FIG. 16 is an enlarged diagram illustrating the camera image.

In a case in which the first cassette ID is not read from the ID marker 32 at the standard magnification of the camera image 76, the identification information acquisition unit 73 enlarges a portion including the ID marker 32 in the camera image 76 as illustrated in FIG. 16 and then reads the first cassette ID. The camera image 76 may be enlarged by electronic zooming. In a case in which the camera 26 has a zoom function, the search processing unit 55 transmits a zoom command to the camera 26 on the basis of the processing result of the identification information acquisition unit 73 to activate the zoom function.

In a case in which the first cassette ID and the second cassette ID are acquired, the search controller 74 collates the first and second cassette IDs. The search controller 74 corresponds to a collation unit. The collation is performed for all of the electronic cassettes 16 included in the camera image 76. In a case in which there is a first cassette ID matched with the second cassette ID on the basis of the collation result, the search controller 74 determines the electronic cassette 16 with the first cassette ID as the use cassette. In a case in which there are no electronic cassettes 16 with the first cassette ID matched with the second cassette ID, the search controller 74 determines that the use cassette is absent in the camera image 76. The search controller 74 performs the determination to check whether the use cassette is included in the camera image 76. As such, the search controller 74 searches for the use cassette in the usage environment through the process using the camera image 76.

Figure 17:
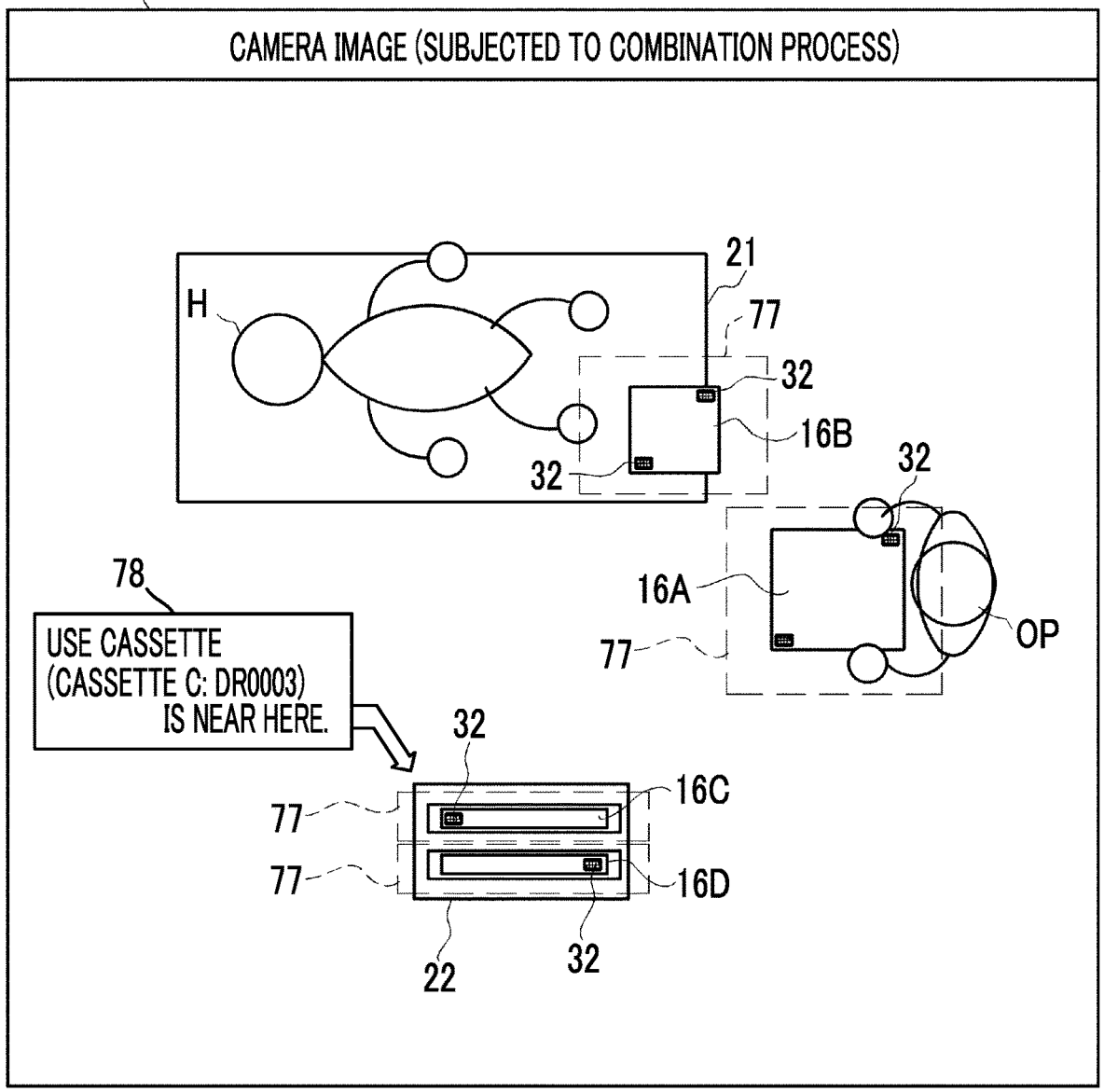
FIG. 17 is a diagram illustrating a camera image into which a cassette region index has been inserted.

As illustrated in FIG. 17, the search controller 74 searches for the use cassette that is included in the camera image 76 and outputs the search result. In a case in which there is a use cassette in the camera image 76, the search controller 74 generates a cassette region index 78 indicating the in-image cassette region 77 of the use cassette in the camera image 76 as the search result and outputs the cassette region index 78 to the image combination unit 75. The cassette region index 78 includes, for example, image data forming the index and coordinate information indicating the insertion position of the camera image 76. In a case in which the use cassette is absent in the camera image 76, the search controller 74 outputs the search result indicating that the use cassette is absent to the image combination unit 75.

The image combination unit 75 performs an image combination process for the camera image 76 on the basis of the search result output from the search controller 74. In a case in which there is a use cassette, the cassette region index 78 is input from the search controller 74. Therefore, the image combination unit 75 performs a combination process of inserting the cassette region index 78 into the in-image cassette region 77 of the use cassette in the camera image 76. In contrast, in a case in which the use cassette is absent, the search result indicating that the use cassette is absent is input to the image combination unit 75. In this case, the image combination unit 75 performs a combination process of inserting a message indicating that the use cassette is absent into the camera image 76.

FIG. 17 illustrates a case in which the electronic cassette 16C having a cassette ID "DR0003" and a name "cassette C" is set as the use cassette as illustrated in FIG. 12. Therefore, in the camera image 76 illustrated in FIG. 17, the cassette region index 78 is inserted at the position of the in-image cassette region 77 of the electronic cassette 16C set as the use cassette. The cassette region index 78 includes, for example, an arrow indicating the in-image cassette region 77 and a message "The use cassette (cassette C: DR0003) is near here.".

The camera 26 outputs the camera image 76 which is a motion picture in real time. The search processing unit 55 repeats a search process including the detection of the in-image cassette region 77 and the first cassette ID and a process of combining the cassette region index 78 and the camera image 76 at a predetermined interval on the basis of the output camera image 76.

In this way, the combined camera image 76 is frequently updated. In a case in which the position of the electronic cassette 16 is changed in the usage environment, the position of the cassette region index 78 in the camera image 76 is also changed.

Figure 18:
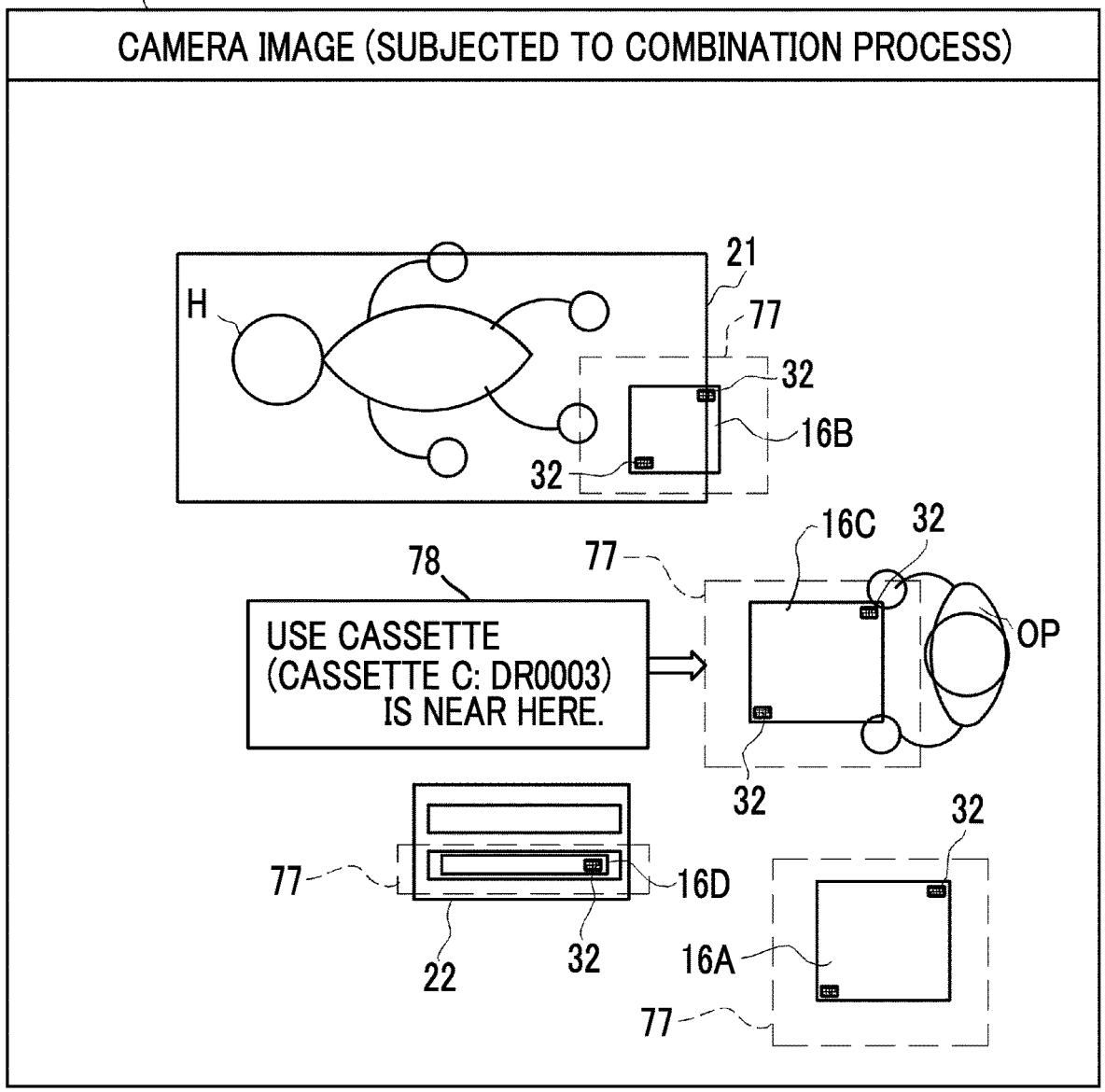
FIG. 18 is a diagram illustrating a camera image changed over time.

For example, in a case in which the operator OP puts the electronic cassette 16A held in the arms of the operator OP as illustrated in FIG. 17 aside, extracts the electronic cassette 16C from the cradle 22, and holds the electronic cassette 16C as illustrated in FIG. 18, the positions of the in-image cassette regions 77 of the electronic cassettes 16A and 16C in the camera image 76 are changed. In a case in which the position of the electronic cassette 16C which is the use cassette is changed, the position of the cassette region index 78 in the camera image 76 is also changed.

Figure 19:
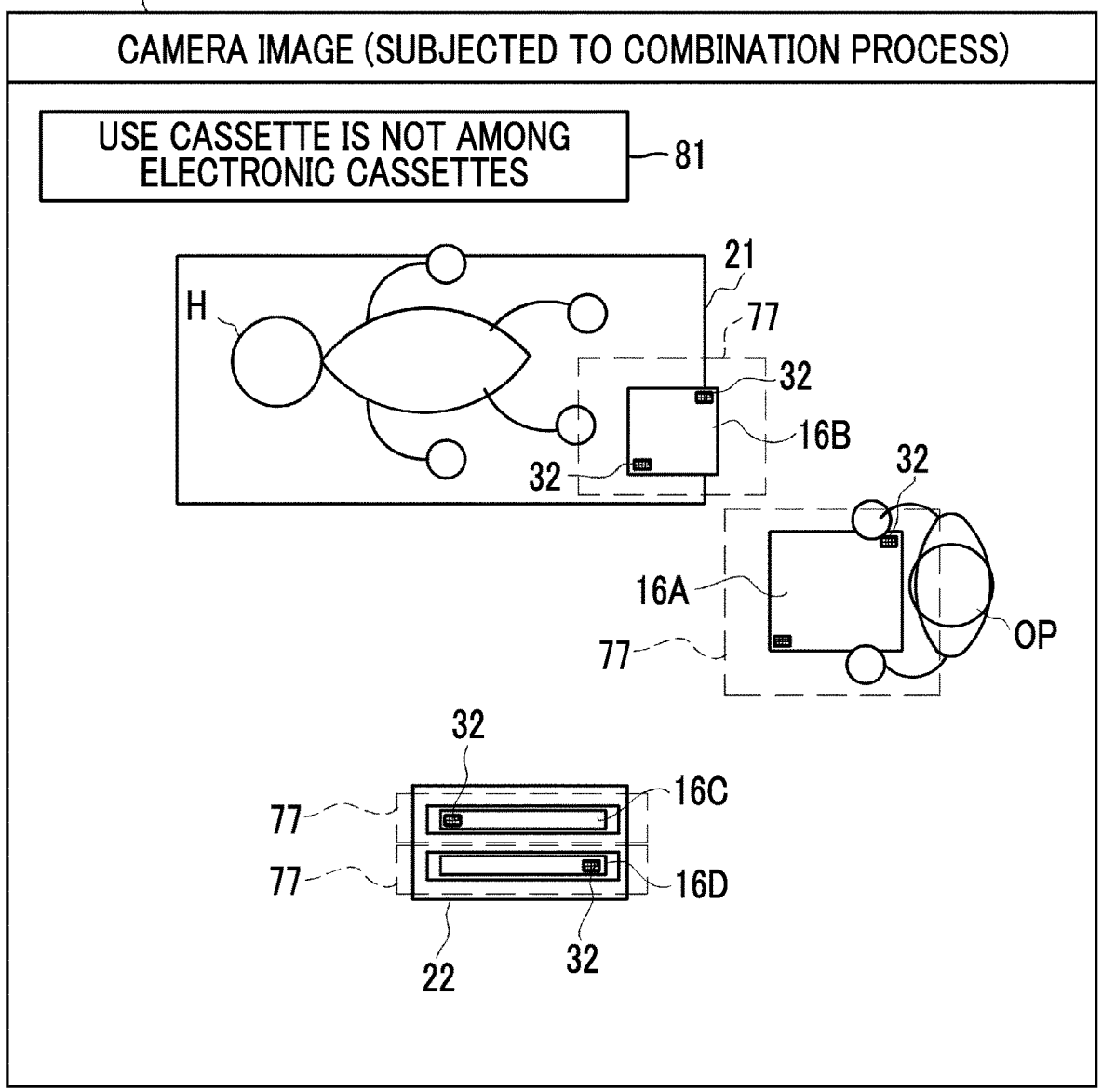
FIG. 19 is a diagram illustrating a camera image in a case in which the use cassette is absent.

In a case in which the search controller 74 determines that the use cassette is absent in the camera image 76 as illustrated in FIG. 19, the camera image 76 into which a message 81 "The use cassette is not among the electronic cassettes" indicating that the use cassette is absent is inserted as the search result is displayed.

The operation of the above-mentioned configuration will be described with reference to the flowcharts illustrated in FIGS. 20 to 23. In a case in which the operator OP performs X-ray imaging using the electronic cassette 16, the operator OP selects the use cassette to be used for X-ray imaging from a plurality of electronic cassettes 16. The use cassette is selected through the console 17.

The operator OP selects the electronic cassette 16 to be used for X-ray imaging from the registered cassettes on the use cassette selection screen 69 illustrated in (A) of FIG. 11 on the basis of the content of the imaging order. In a case in which the selection operation is received, the console 17 sets the electronic cassette 16 selected by the operator OP as the use cassette. In a case in which, for example, the electronic cassette 16C is selected as illustrated in (B) of FIG. 11 and FIG. 12, the selected electronic cassette 16C is set as the use cassette.

The operator OP relatively positions the electronic cassette 16, the X-ray source 13, and the subject H. At that time, in some cases, the operator OP wants to check whether the electronic cassette 16 to be used for X-ray imaging has been set as the use cassette in the console 17. In particular, in a case in which the electronic cassette 16 and the console 17 are wirelessly connected to each other, the connection between the electronic cassette 16 and the console 17 is not a physical connection through a cable, but is only a logical connection on data. Therefore, in a method for visually checking a physical cable, it is difficult to check whether the electronic cassette has been set as the use cassette.

In this case, the operator OP uses a use cassette search function of the console 17. In a case in which the search function is used, the operator OP operates the cassette search button 67 on the imaging order display screen 61 illustrated in FIG. 9.

Figure 20:
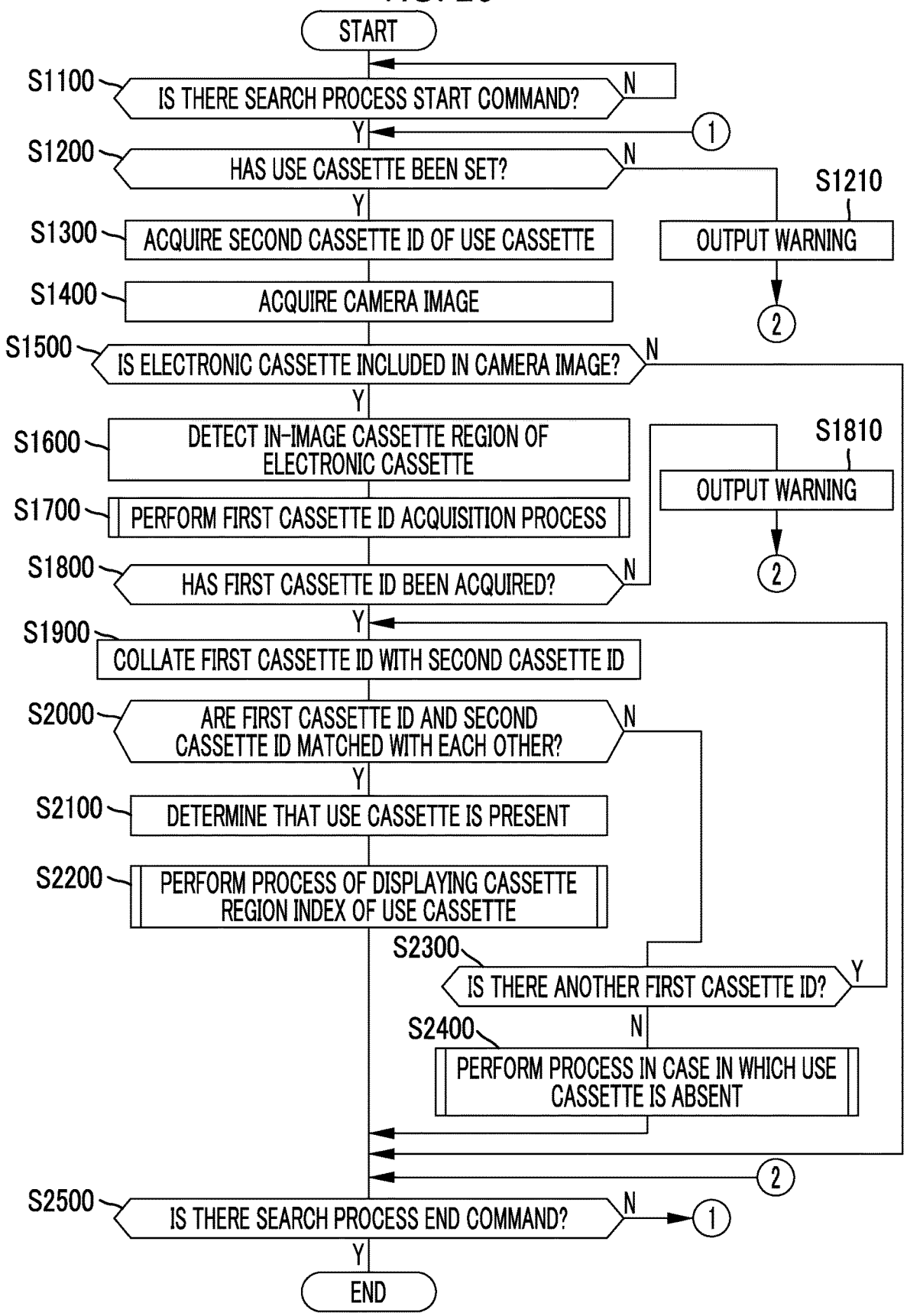
FIG. 20 is a flowchart illustrating the procedure of a search process.

As illustrated in FIG. 20, the console 17 waits for the input of a search process start command during operation (Step S1100). In a case in which the cassette search button 67 is operated, the console 17 determines that the search process start command has been issued (Y in S1100). The search processing unit 55 determines whether the use cassette has been set with reference to the use cassette setting information 58 (S1200). In a case in which the use cassette has been set in the use cassette setting information 58 (Y in S1200), the search controller 74 acquires the second cassette ID of the use cassette with reference to the use cassette setting information 58 (S1300).

In a case in which the use cassette has not been set in S1200 (N in S1200), a warning indicating that the use cassette has not been set is output (S1210). Then, the process proceeds to S2500. In a case in which a search process end command is issued (Y in S2500), the search process ends. In a case in which there are no end commands, the process returns to S1200.

The network communication unit 54 acquires the camera image 76 which is a motion picture that is output from the camera 26 in real time (S1400). As illustrated in FIG. 14, the camera image 76 includes the usage environment in which the electronic cassette 16 is used. The acquired camera image 76 is input to the in-image cassette detection unit 72 of the search processing unit 55.

The in-image cassette detection unit 72 performs an image recognition process on the basis of the camera image 76 to check whether the electronic cassette 16 is included in the camera image 76 (S1500). In a case in which the electronic cassette 16 is included in the camera image 76 (Y in S1500), the in-image cassette detection unit 72 detects the in-image cassette region 77 of the electronic cassette 16 as illustrated in FIG. 15 (S1600). In a case in which a plurality of electronic cassettes 16 are included in the camera image 76, the in-image cassette detection unit 72 detects the in-image cassette regions 77 of all of the electronic cassettes 16. The in-image cassette detection unit 72 outputs the detected in-image cassette region 77 to the identification information acquisition unit 73.

In a case in which the in-image cassette region 77 is input from the in-image cassette detection unit 72, the identification information acquisition unit 73 performs a first cassette ID acquisition process (S1700).

Figure 21:
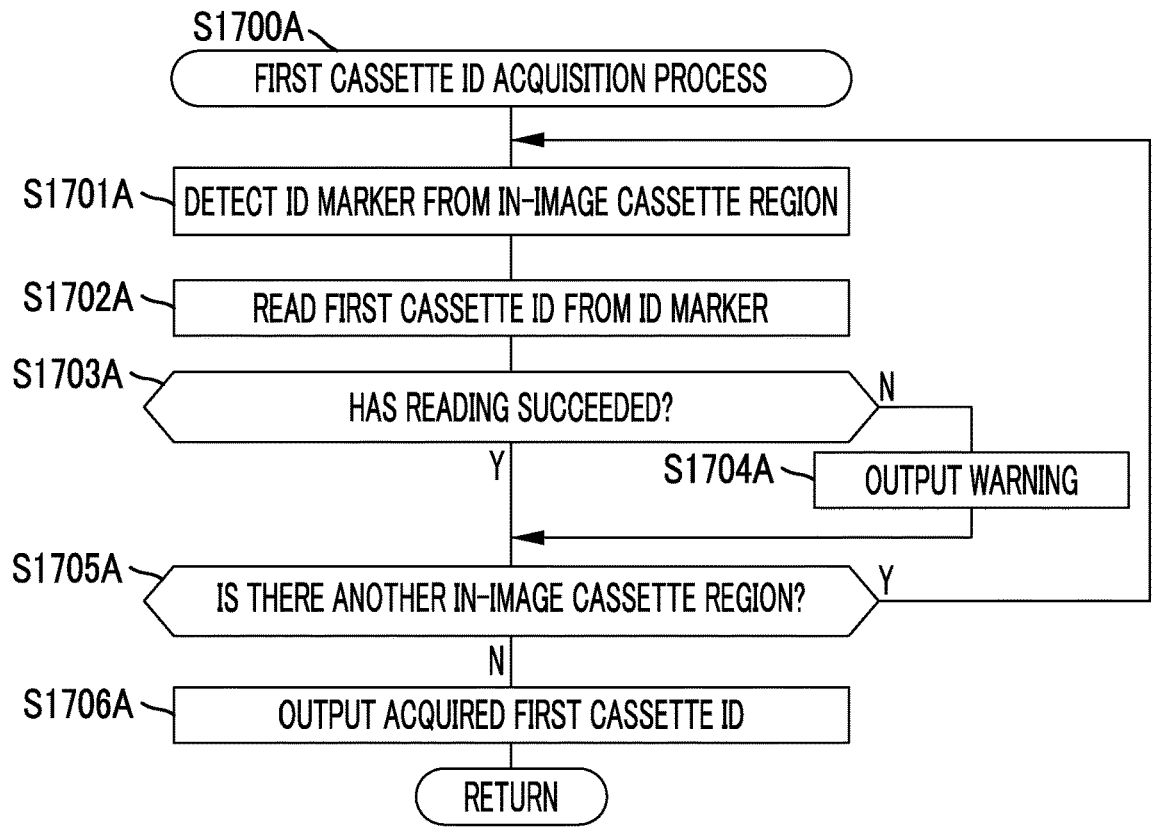
FIG. 21 is a flowchart illustrating the procedure of a first cassette ID acquisition process.

For example, the first cassette ID acquisition process is performed according to the procedure illustrated in the flowchart of S1700A illustrated in FIG. 21. In the first cassette ID acquisition process in S1700A, first, the identification information acquisition unit 73 detects the ID marker 32 from the in-image cassette region 77 in S1701A. Then, in S1702A, the identification information acquisition unit 73 reads the first cassette ID from the ID marker 32.

In a case in which the reading has succeeded in S1703A (Y in S1703A), the identification information acquisition unit 73 checks whether there is another in-image cassette region 77 (S1705A). On the other hand, in a case in which the reading has failed in S1703A (N in S1703A), the identification information acquisition unit 73 issues a warning indicating that the ID marker 32 is not readable (S1704A). For example, the warning is performed by displaying a warning message on the touch panel 33 or by outputting a warning sound from a speaker.

In a case in which there is another in-image cassette region 77 (Y in S1705), the process from S1701A to S1704A is performed. Then, in a case in which the process of reading the first cassette IDs from all of the in-image cassette regions 77 has been completed, the identification information acquisition unit 73 outputs the information of the acquired first cassette ID and the acquired in-image cassette region 77 to the search controller 74 (S1706A). Then, the identification information acquisition unit 73 returns to the flow illustrated in FIG. 20 and proceeds to S1800.

Returning to FIG. 20, in a case in which the first cassette ID has been acquired (Y in S1800), the search controller 74 collates the first cassette ID with the second cassette ID (S1900). On the other hand, in a case in which no first cassette IDs have been acquired (N in S1800), a warning indicating that no first cassette IDs have been acquired is issued (S1810) and the process proceeds to S2500. In a case in which a search process end command is issued (Y in S2500), the search process ends. In a case in which the end command is not issued, the process returns to S1200.

In a case in which the collation result shows that the first cassette ID and the second cassette ID are matched with each other (Y in S2000), the search controller 74 determines that the electronic cassette 16 with the first cassette ID is the use cassette and that the use cassette is included in the camera image 76 (S2100).

On the other hand, in a case in which the collation result shows that the first cassette ID and the second cassette ID are not matched with each other (N in S2000), the search controller 74 checks whether there is another first cassette ID (S2300). In a case in which there is another first cassette ID (Y in S2300), the process returns to S1900. In a case in which there is no another first cassette ID (N in S2300), the process proceeds to S2400.

Figure 22:
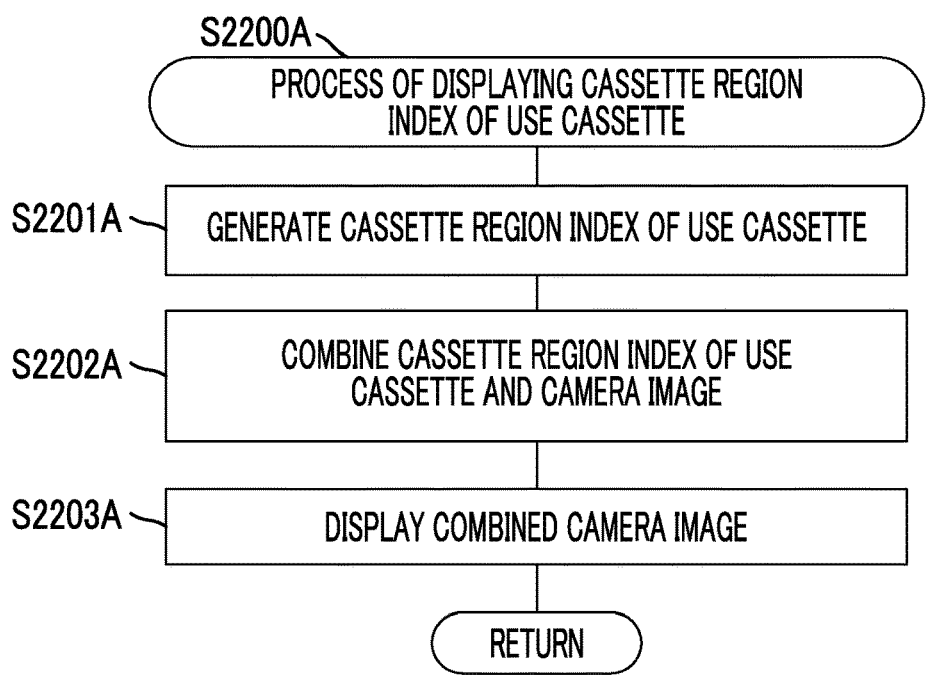
FIG. 22 is a flowchart illustrating the procedure of a cassette region index display process.

In a case in which it is determined that there is a use cassette (S2100), the search controller 74 performs a cassette region index display process for the use cassette (S2200). For the cassette region index display process, for example, a cassette region index display process in S2200A illustrated in FIG. 22 is performed. The search controller 74 generates the cassette region index 78 corresponding to the in-image cassette region 77 of the use cassette (S2201A) and outputs the generated cassette region index 78 to the image combination unit 75. Then, the image combination unit 75 combines the camera image 76 and the cassette region index 78 of the use cassette (S2202A). Then, the camera image 76 subjected to the combination process illustrated in FIG. 17 is output to the GUI controller 51 and is displayed on the touch panel 33 which is a display unit (S2203A).

In contrast, as described above, in a case in which the first cassette ID matched with the second cassette ID is absent (N in S2300), the process proceeds to S2400 which is performed in a case in which the use cassette is absent.

Figure 23:
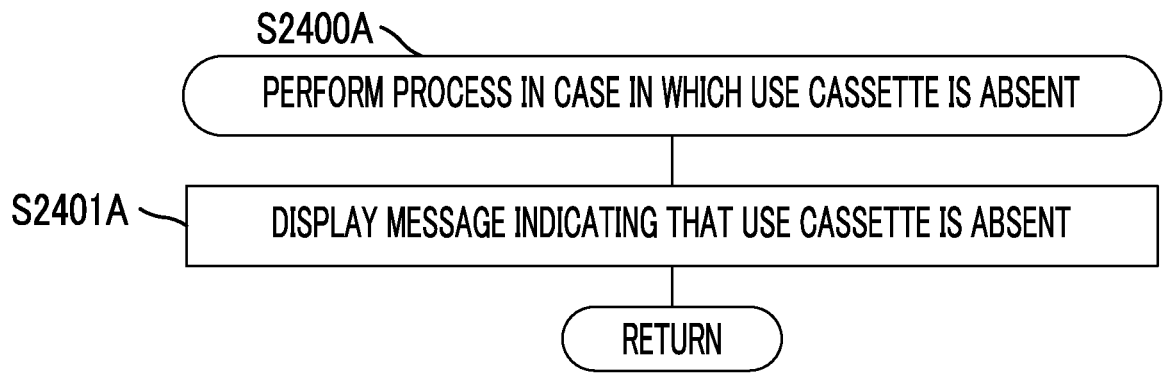
FIG. 23 is a flowchart illustrating the procedure of a process in a case in which the use cassette is absent.

For the process in a case in which the use cassette is absent, for example, the search controller 74 outputs a message indicating that the use cassette is absent as the search result to the image combination unit 75 as illustrated in S2400A of FIG. 23. As illustrated in FIG. 19, the image combination unit 75 inserts the message indicating that the use cassette is absent into the camera image 76. The camera image 76 subjected to the combination process is displayed on the touch panel 33 through the GUI controller 51 (S2401A).

In FIG. 20, the search processing unit 55 repeats the process from S1200 to S2400 until a search process end command is issued (N in S2500).

As such, in the X-ray imaging system 10, the console 17 has a function of searching for the electronic cassette 16 set as the use cassette on the basis of the camera image 76 obtained by capturing the usage environment. In a case in which the use cassette is included in the camera image 76, the cassette region index 78 indicating the position of the use cassette is inserted into the camera image 76 as illustrated in FIG. 17. Therefore, the operator OP can easily find the use cassette set by the console from a plurality of electronic cassettes 16 in the usage environment.

After the use cassette is checked, X-ray imaging is performed using the use cassette. The operator OP positions the X-ray source 13, the use cassette, and the subject H and then operates the irradiation switch 23. Then, the X-ray generation apparatus 11 irradiates the subject H with X-rays and the use cassette acquires an X-ray image of the subject H. The use cassette transmits the acquired X-ray image to the console 17.

In a case in which the use cassette is checked by the function of searching for the electronic cassette 16, it is possible to prevent a non-use cassette, which is the electronic cassette 16 other than the paired use cassette, from being falsely recognized as the use cassette in X-ray imaging.

In a case in which the console 17 and the electronic cassette 16 are wirelessly connected to each other as in this example, it is difficult to check the connection state between the console 17 and the electronic cassette 16 since a visible cable is not used. Therefore, the invention that can visualize a logical connection state between the console 17 and the electronic cassette 16 set as the use cassette in the console 17 is very effective.

In addition, for example, a seal on which the cassette ID is recorded may be attached to the housing 28 of the electronic cassette 16 and the cassette ID read from the seal may be collated with the cassette ID set in the console 17. In this case, it is possible to check the electronic cassette 16 set as the use cassette. However, in a case in which there are a plurality of electronic cassettes 16, it is necessary to perform the check operation for each electronic cassette 16, which requires a lot of time and effort. According to the invention, it is possible to reduce the time and effort required for the check operation.

Even in the configuration in which the electronic cassette 16 and the console 17 are connected to each other by a cable, the invention is effective in the following case. For example, in some cases, one console 17 is connected to a plurality of electronic cassettes 16 by a bifurcated cable or a hub. In this case, similarly to the wireless connection, it is difficult to check at a glance which of the plurality of electronic cassettes 16 connected by the cable is set as the use cassette in the console 17.

In this example, the aspect in which the cassette region index 78 is inserted into the camera image 76 and is then displayed has been described as the display aspect of the cassette region index 78. However, the cassette region index 78 may not be necessarily inserted into the camera image 76. For example, the cassette region index 78 may be displayed outside the frame of the camera image 76 as long as it can indicate the region of each electronic cassette 16 in the camera image 76.

In this example, in a case in which the use cassette is absent in the camera image 76, the message 81 indicating that the use cassette is absent is inserted into the camera image 76 and is then displayed as illustrated in FIG. 19. However, the message 81 is not necessarily displayed. In a case in which the use cassette is absent in the camera image 76, the camera image 76 in which the message 81 is not inserted may be displayed. That is, as illustrated in FIG. 14, only the camera image 76 may be displayed.

In the flow according to this example illustrated in FIG. 20, the second cassette ID acquisition process in S1300 is performed before the first cassette ID acquisition process in S1700. However, the second cassette ID acquisition process may be performed after the first cassette ID acquisition process. The second cassette ID acquisition process may be performed at any time as long as it is performed until the collation process in S1900.

The example in which the camera 26 is provided on the ceiling of the imaging room has been described. However, for example, the camera 26 may be provided on the wall of the imaging room. In addition, a stand including a support that extends in the vertical direction and an arm whose angle can be adjusted may be provided and the camera 26 may be attached to the leading end of the arm, instead of being provided on the ceiling or the wall. Even in a case in which the camera 26 is provided on the ceiling or the wall, the camera 26 may be attached to the ceiling or the wall through, for example, an arm that can adjust the imaging direction. That is, in a case in which the usage environment of the electronic cassette 16 is a room, the camera 26 may be provided at any position in the room as long as it can view the usage environment.

In this embodiment, a motion picture is given as an example of the camera image 76 output from the camera 26. However, the camera image may be a still image. In the case of the still image, the still images may be captured at a predetermined interval and then sequentially output. In this case, it is possible to check an aspect of a change in the usage environment over time.

In each of the subsequent embodiments including the following second embodiment, the description is focused on a difference from the first embodiment. In addition, the same components as those in the first embodiment are denoted by the same reference numerals and the description thereof will not be repeated.

Second Embodiment

Figure 24:
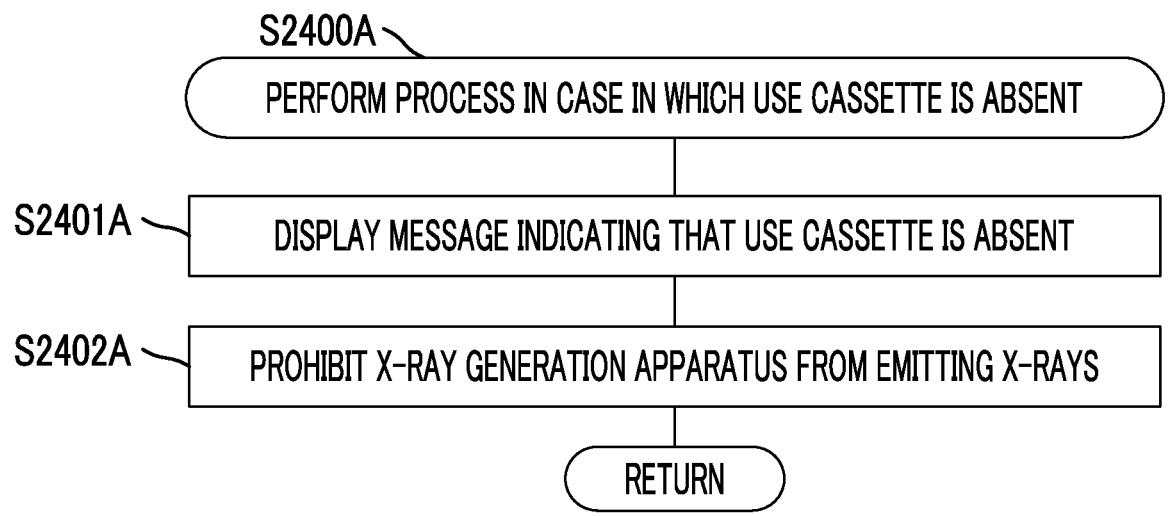
FIG. 24 is a flowchart illustrating a second embodiment.
Figure 25:
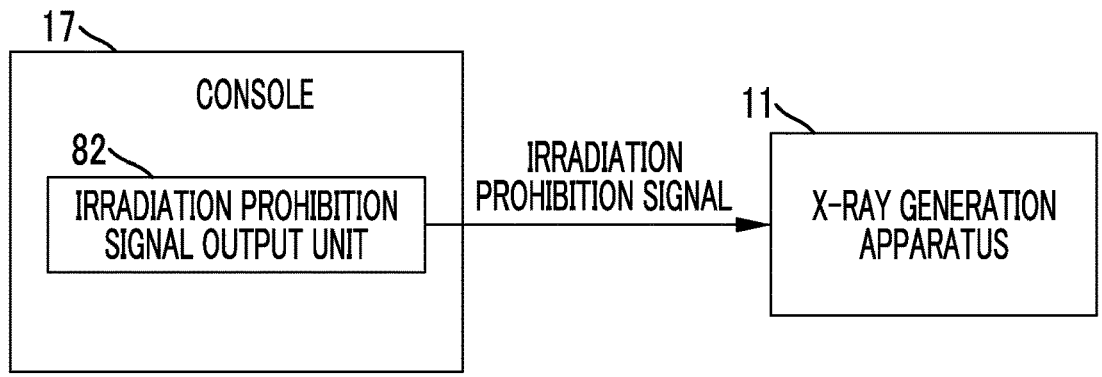
FIG. 25 is a diagram illustrating an irradiation prohibition signal output unit according to a second embodiment.

As in a second embodiment illustrated in FIGS. 24 and 25, in a case in which the use cassette is absent in the camera image 76, the emission of X-rays may be prohibited. For the process in a case in which the use cassette is absent in S2400 of FIG. 20, in the example illustrated in FIG. 23, only the process (S2401A) of displaying the message 81 indicating that the use cassette is absent is performed. In the second embodiment, as illustrated in FIG. 24, in addition to S2401A, a process of prohibiting the irradiation operation of the X-ray generation apparatus 11 is performed (S2402A).

In this case, as illustrated in FIG. 25, the console 17 is provided with an irradiation prohibition signal output unit 82. In a case in which the operation program 50 is executed, the CPU 41 functions as the irradiation prohibition signal output unit 82. The console 17 and the X-ray generation apparatus 11 are connected such that they communicate with each other in a wired manner or wirelessly. In a case in which the determination result indicating that the use cassette is absent in the camera image 76 is received from the search processing unit 55, the irradiation prohibition signal output unit 82 transmits an irradiation prohibition signal to the X-ray generation apparatus 11. Then, the X-ray generation apparatus 11 prohibits irradiation. As such, in a case in which the use cassette is absent in the usage environment, the emission of X-rays is prohibited. Therefore, it is possible to reliably prevent an imaging failure in which an X-ray image is not acquired even in a case in which X-rays are emitted.

Third Embodiment

In a third embodiment illustrated in FIGS. 26 to 29, the identification information acquisition unit 73 detects identification light emitted from an indicator 84 that is provided in the electronic cassette 16 and acquires the first cassette ID from the camera image 76. In the first embodiment, for the first cassette ID acquisition process in S1700 of FIG. 20, the first cassette ID is acquired from the ID marker 32 as illustrated in S1700A of FIG. 21. Instead of acquiring the first cassette ID from the ID marker 32 as in the first embodiment, the identification information acquisition unit 73 may acquire the first cassette ID from the identification light emitted from the indicator 84 as in the third embodiment.

Figure 26:
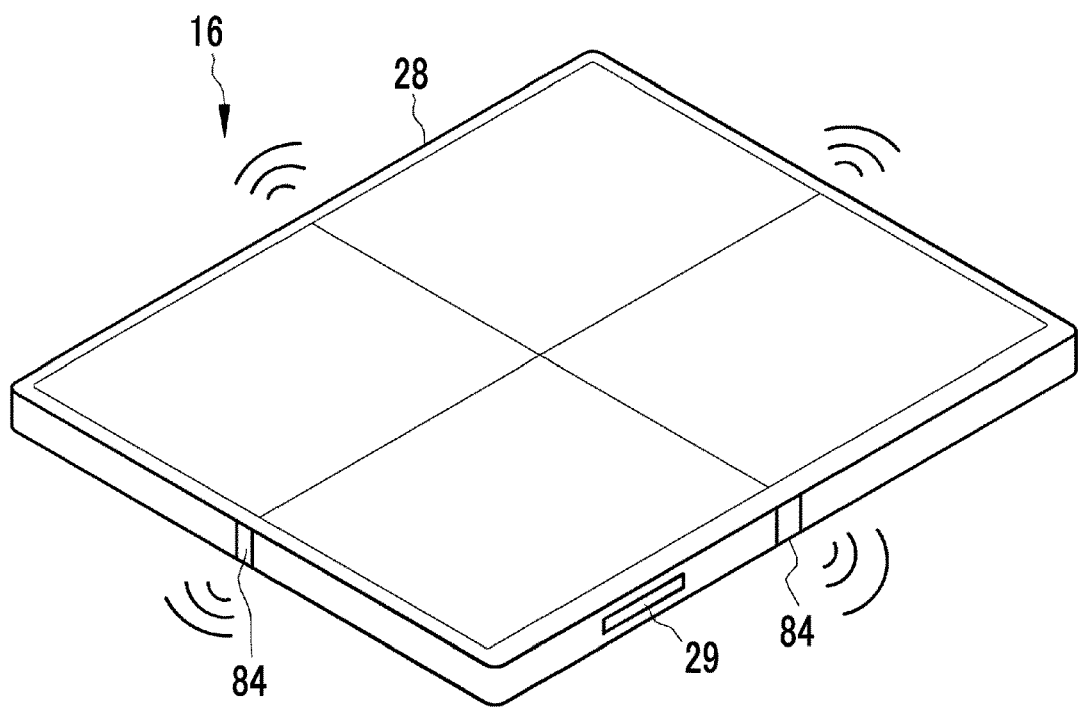
FIG. 26 is a perspective view illustrating a front surface side of an electronic cassette according to a third embodiment.
Figure 27:
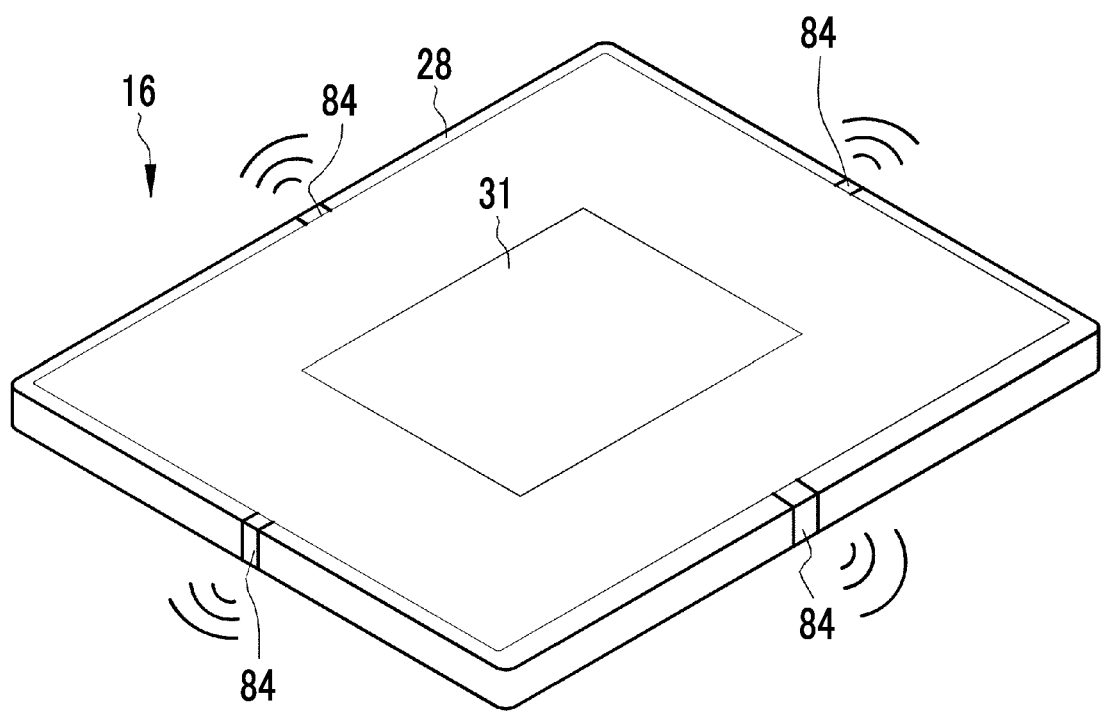
FIG. 27 is a perspective view illustrating a rear surface side of the electronic cassette according to the third embodiment.

As illustrated in FIGS. 26 and 27, in the third embodiment, for example, the indicator 84 is provided at the center of each of four side surfaces of the housing 28 of the electronic cassette 16. The indicator 84 is a light source such as a light emitting diode (LED). The indicator 84 can emit identification light of a plurality of colors such as red, blue, and green.

Figure 28:
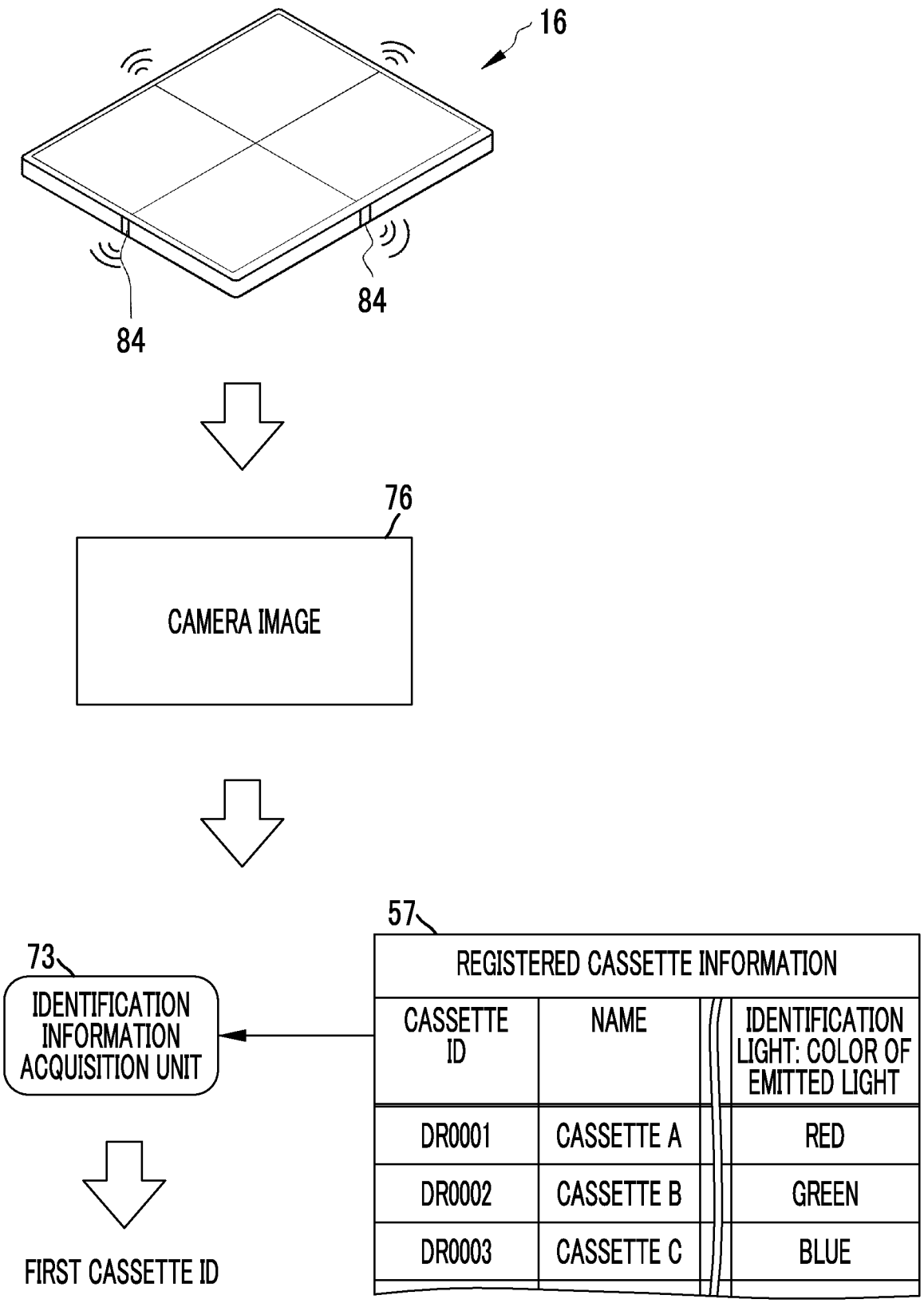
FIG. 28 is a diagram illustrating the outline of a process according to the third embodiment.

In the third embodiment, as illustrated in FIG. 28, in the registered cassette information 57 of the console 17, the color of the identification light is allocated to each registered electronic cassette 16. In this example, "red" is allocated to an electronic cassette 16A with a cassette ID "DR0001", "green" is allocated to an electronic cassette 16B with a cassette ID "DR0002", and "blue" is allocated to an electronic cassette 16C with a cassette ID "DR0003". The identification information acquisition unit 73 reads the cassette ID from the identification light with reference to the registered cassette information 57.

Figure 29:
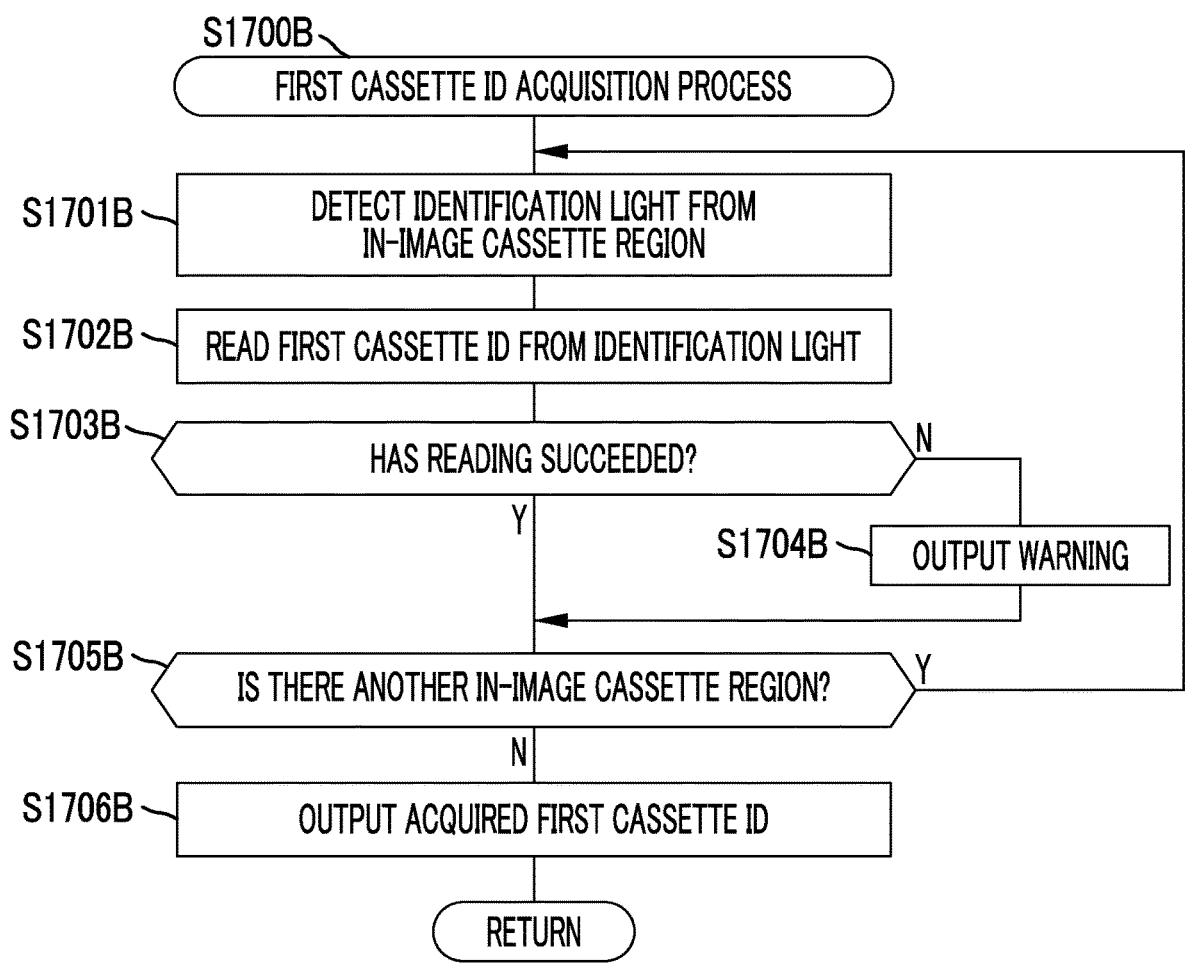
FIG. 29 is a flowchart illustrating the procedure of a first cassette ID acquisition process according to the third embodiment.

In the third embodiment, the identification information acquisition unit 73 performs the first cassette ID acquisition process in S1700B of FIG. 29 as the first cassette ID acquisition process in S1700 of FIG. 20, instead of the process in S1700A of FIG. 21 in the first embodiment. The identification information acquisition unit 73 detects the identification light emitted from the indicator 84 from the in-image cassette region 77 detected by the in-image cassette detection unit 72 (S1701B). Then, the identification information acquisition unit 73 identifies the color of the identification light and reads the first cassette ID with reference to the correspondence relationship between the identification light and the cassette ID of the registered cassette information 57 (S1702B). In a case in which the reading of the first cassette ID has failed (N in S1703B), the identification information acquisition unit 73 outputs a warning (S1704B). The subsequent process in S1705B and S1706B is the same as the process in S1705A and S1706A described in FIG. 21.

In this example, the identification light is identified on the basis of the color and the cassette ID is read. However, the identification light may be identified on the basis of a lighting pattern or a lighting time, instead of the color. The lighting pattern is identified by, for example, a flashing cycle. The lighting time is, for example, the time until the indicator 84 is turned on after a lighting command is transmitted from the console 17 to the electronic cassette 16. The lighting pattern or the lighting time is recorded for each cassette ID in the registered cassette information 57 in advance. In this case, the identification information acquisition unit 73 reads the first cassette ID with reference to the registered cassette information 57 using the method illustrated in FIGS. 28 and 29.

According to the third embodiment, it is possible to acquire the cassette ID, without providing the ID marker 32 in the housing 28.

Fourth Embodiment

In a fourth embodiment illustrated in FIGS. 30 and 31, an identification information request signal (hereinafter, simply referred to as a request signal) that requests the first cassette ID is transmitted to the electronic cassette 16 and the first cassette ID is acquired as a response from the electronic cassette 16.

In the fourth embodiment, a request signal transmission unit 86 that transmits the request signal is provided in the vicinity of the camera 26 (for example, on the outer surface of the camera 26). The request signal transmission unit 86 transmits the request signal to each electronic cassette 16 in the usage environment and receives response signals from the electronic cassettes 16 that have received the request signal. In addition, the request signal transmission unit 86 is connected to the network 43, similarly to the camera 26, and can communicate with the console 17.

The request signal is, for example, light, electromagnetic waves, or sound waves with directionality. The request signal transmission unit 86 has a direction control function of transmitting the request signal in a direction in which each electronic cassette 16 is present. The direction control function is implemented by, for example, a method which provides a rotation mechanism for rotating a transmitter that transmits the request signal in the request signal transmission unit 86 or a method which provides a plurality of transmitters in different directions in the request signal transmission unit 86. In this case, the electronic cassette 16 is provided with a transmitting and receiving unit that receives the request signal and transmits a response signal according to the form of the request signal such as light, electromagnetic waves, or sound waves.

The request signal that has been transmitted to a specific electronic cassette 16 by the direction control function of the request signal transmission unit 86 is not received by other electronic cassettes 16. Therefore, a response signal to the request signal can be determined to be a response signal transmitted from the electronic cassette 16 that is present in the transmission direction of the request signal.

Figure 30:
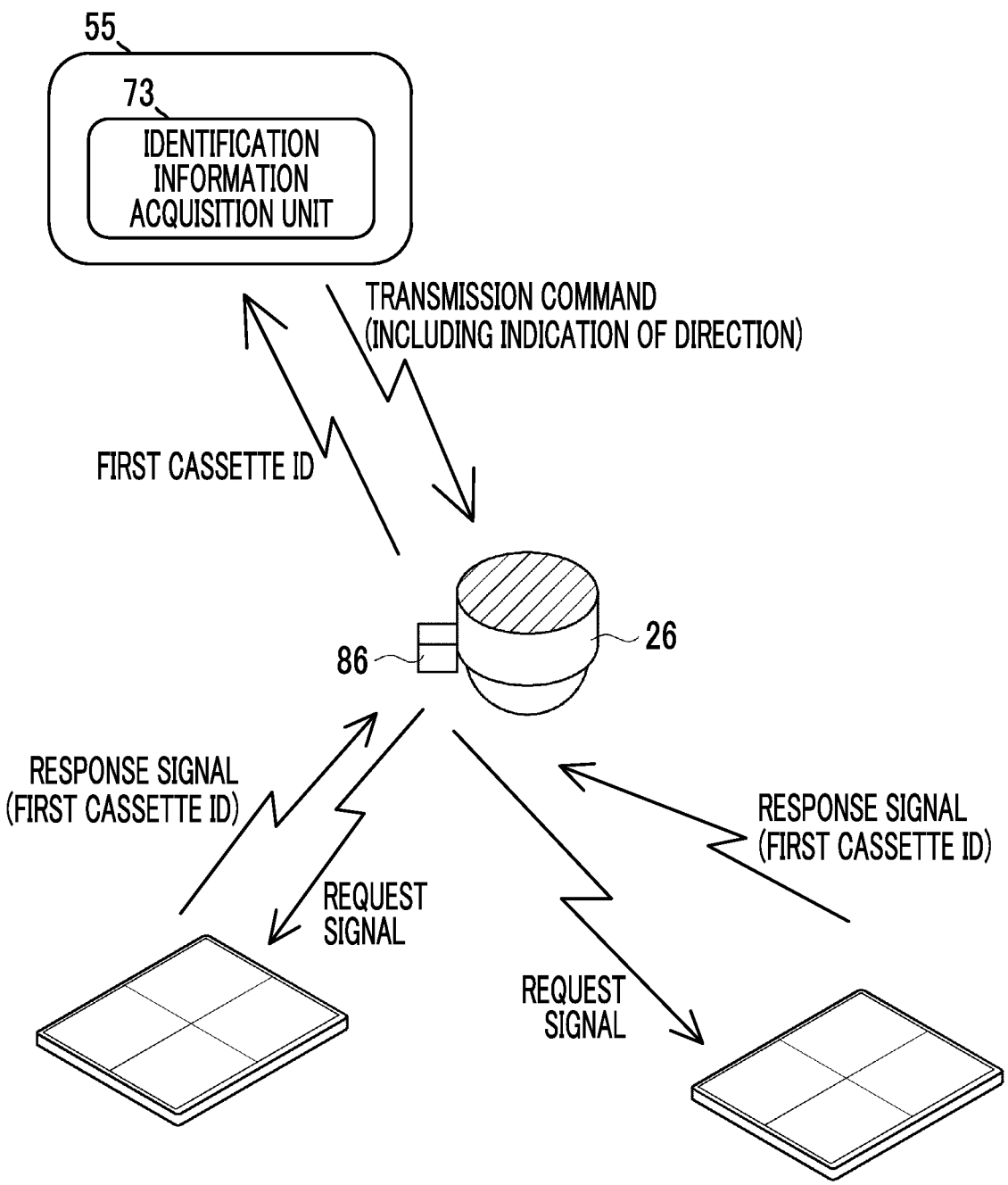
FIG. 30 is a diagram illustrating the outline of a process according to a fourth embodiment.

For example, in a case in which the request signal transmission unit 86 transmits the request signal to the electronic cassette 16C in FIG. 30, the request signal is not received by the electronic cassette 16A and is received by only the electronic cassette 16C. Therefore, only the electronic cassette 16C transmits a response signal to the request signal. The response signal can be determined to be a response signal transmitted from the electronic cassette 16C. The response signal includes the cassette ID of the electronic cassette 16C.

The identification information acquisition unit 73 functions as a direction detection unit that detects the direction in which the electronic cassette 16 is present in the usage environment on the basis of the in-image cassette region 77 input from the in-image cassette detection unit 72. Since the request signal transmission unit 86 is provided in the vicinity of the camera 26, the direction of the electronic cassette 16 detected by the identification information acquisition unit 73 on the basis of the camera image 76 is substantially matched with the actual direction in which the electronic cassette 16 is present in the usage environment.

The search processing unit 55 transmits a transmission command including the indication of the direction detected by the identification information acquisition unit 73 to the request signal transmission unit 86 through the network 43. The request signal transmission unit 86 transmits the request signal in the indicated direction, that is, the direction detected by the identification information acquisition unit 73 (direction detection unit) in response to the received transmission command and receives a response signal. The request signal transmission unit 86 transmits the response signal to the console 17 through the network 43.

Figure 31:
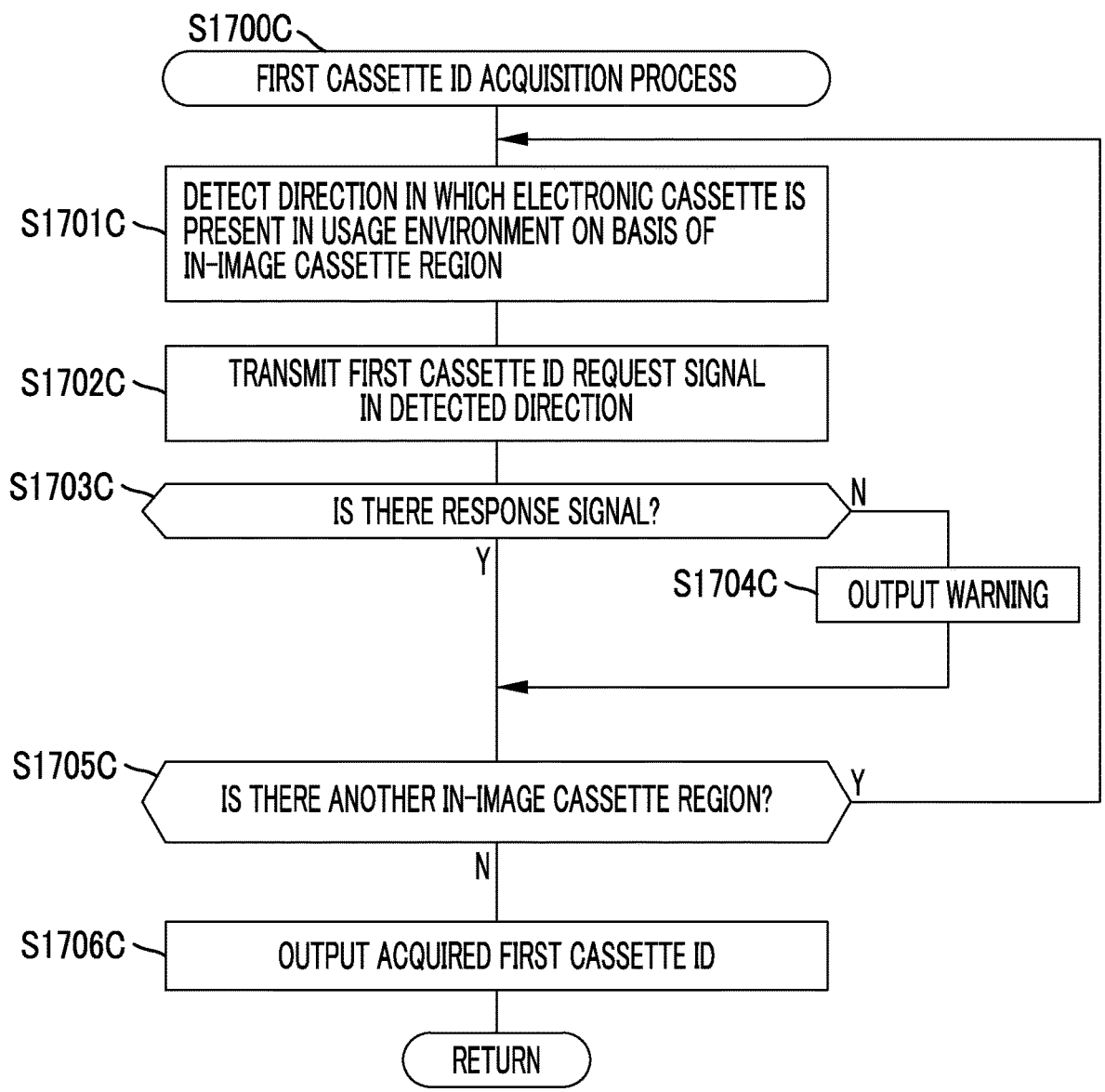
FIG. 31 is a flowchart illustrating the procedure of a first cassette ID acquisition process according to the fourth embodiment.

In the fourth embodiment, for the first cassette ID acquisition process in S1700 illustrated in FIG. 20, a first cassette ID acquisition process in S1700C illustrated in FIG. 31 is performed. The identification information acquisition unit 73 detects the direction in which the electronic cassette 16 is present in the usage environment on the basis of the in-image cassette region 77 detected by the in-image cassette detection unit 72 (S1701C).

The request signal transmission unit 86 transmits a first cassette ID request signal in the detected direction (S1702C). In a case in which the request signal transmission unit 86 receives a response signal (Y in S1703C), a response signal including the first cassette ID is transmitted to the console 17. Then, the identification information acquisition unit 73 acquires the first cassette ID. In a case in which the request signal transmission unit 86 does not receive a response signal (N in S1703C), a warning indicating that a response signal (first cassette ID) is not capable of being received is issued (S1704C). The subsequent process in S1705C and S1706C is the same as that in S1705A and S1706A described in FIG. 21.

Fifth Embodiment

Figure 32:
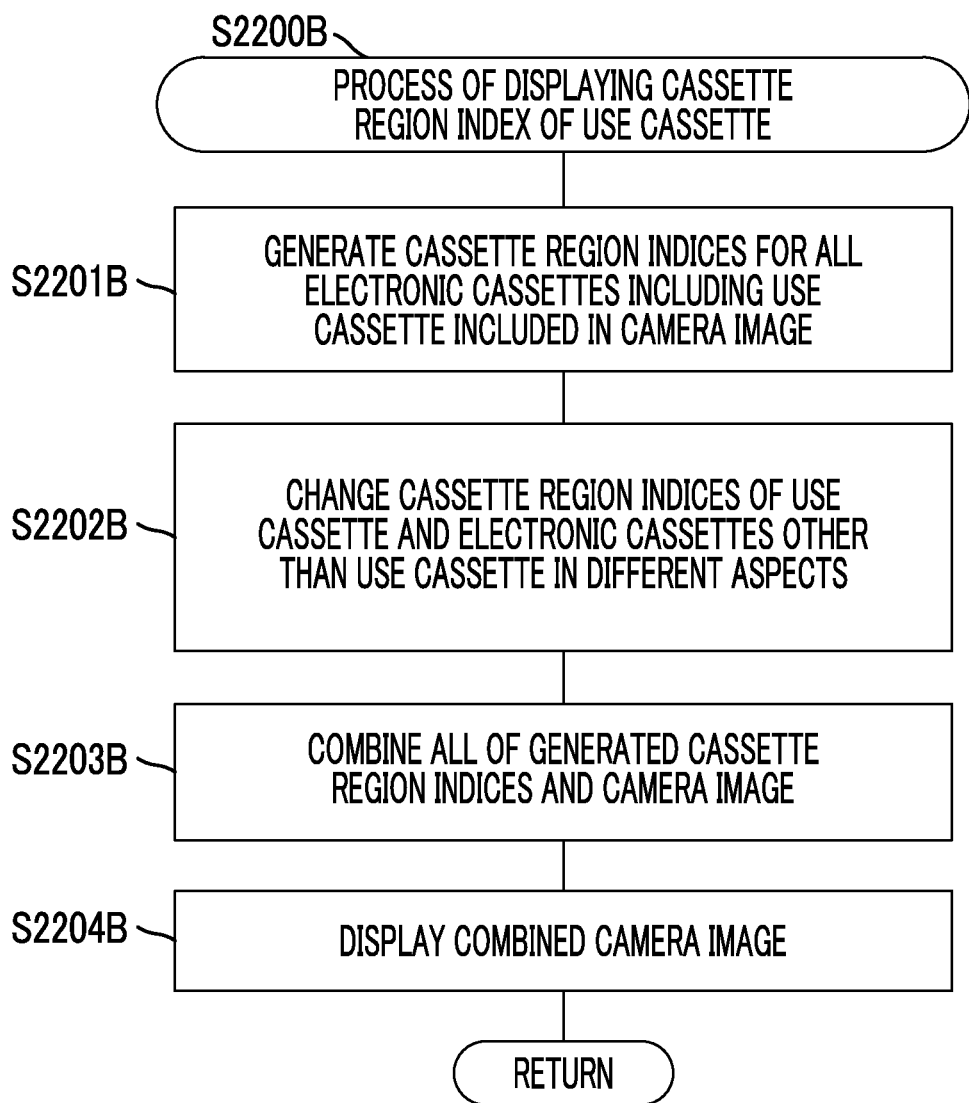
FIG. 32 is a flowchart illustrating the procedure of a cassette region index display process according to a fifth embodiment.
Figure 33:
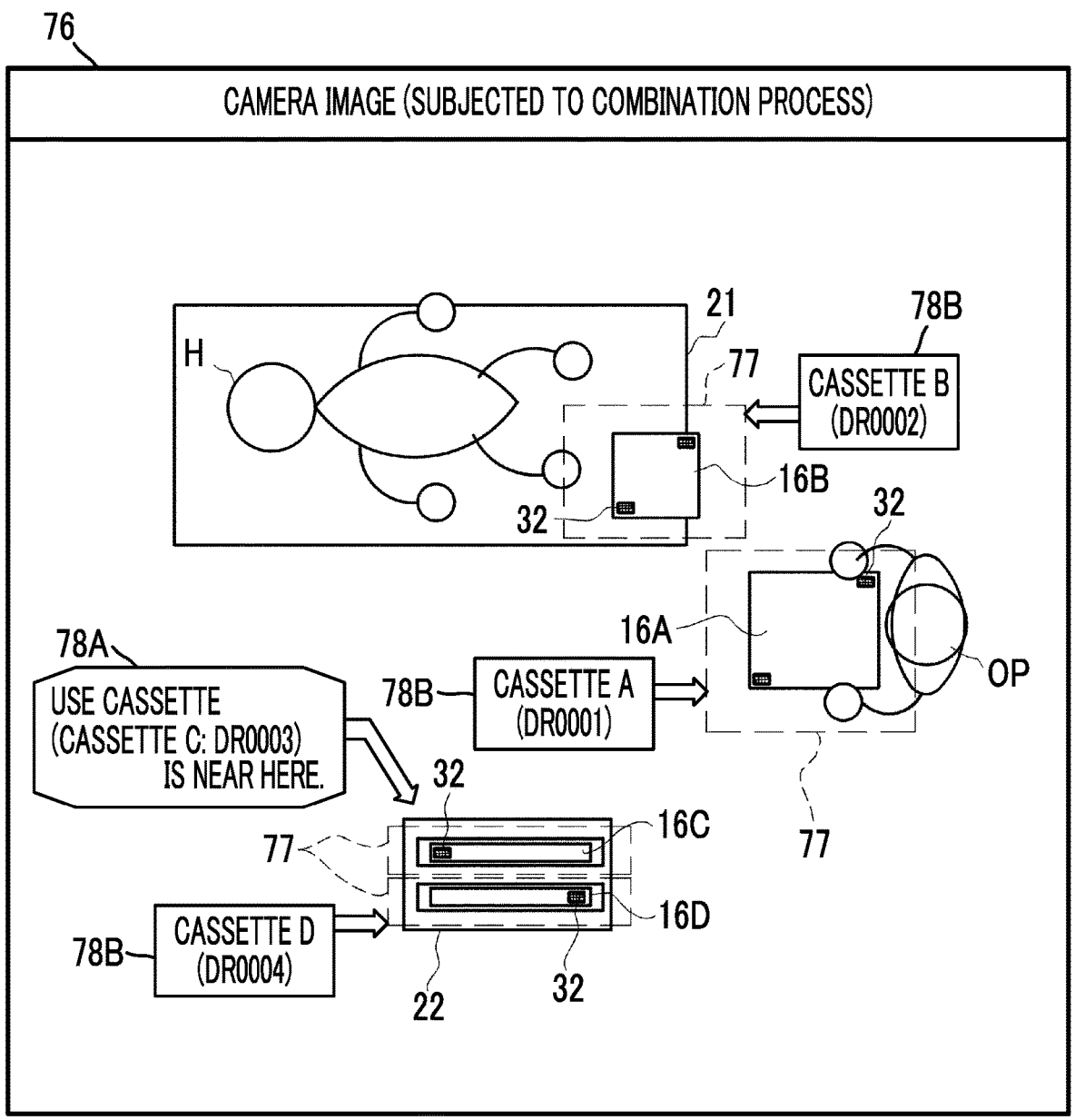
FIG. 33 is a diagram illustrating a camera image according to the fifth embodiment.

In a fifth embodiment illustrated in FIGS. 32 and 33, for the cassette region index display process in S2200 illustrated in FIG. 20, the cassette region indices 78 for all of the electronic cassettes 16 included in the camera image 76 are displayed. In the first embodiment, as illustrated in FIG. 17, the cassette region index 78 for only the use cassette is displayed. However, as in the fifth embodiment, the cassette region indices 78 for all of the electronic cassettes 16 may be displayed.

In the fifth embodiment, for the process in S2200 illustrated in FIG. 20, a cassette region index display process in S2200B illustrated in FIG. 32 is performed. As described above, in a case in which a plurality of electronic cassettes 16 are included in the camera image 76, the in-image cassette detection unit 72 detects the in-image cassette regions 77 of all of the electronic cassettes 16 included in the camera image 76. Then, the identification information acquisition unit 73 acquires the first cassette IDs from all of the in-image cassette regions 77 and outputs the information of the first cassette IDs and the in-image cassette regions 77 to the search controller 74.

The search controller 74 generates the cassette region indices 78 for all of the electronic cassettes 16 including the use cassette in the camera image 76, on the basis of the first cassette IDs and the in-image cassette regions 77 (S2201B).

The search controller 74 stores the collation results between the second cassette ID and a plurality of first cassettes ID and determines whether each of a plurality of in-image cassette regions 77 is the in-image cassette region 77 of the use cassette or the in-image cassette region 77 of the electronic cassette other than the use cassette. Then, the search controller 74 changes the cassette region index 78 of the use cassette and the cassette region indices 78 of the other electronic cassettes 16 to different aspects (S2202B).

The image combination unit 75 combines all of the generated cassette region indices 78 and the camera image 76. The combined camera image 76 is displayed on the touch panel 33 which is a display unit through the GUI controller 51 (S2204B).

Specifically, the combined camera image 76 is as illustrated in FIG. 33. A cassette region index 78A for the use cassette (electronic cassette 16C) is inserted into the in-image cassette region 77 of the use cassette in the camera image 76 and cassette region indices 78B for the electronic cassettes other than the use cassette are inserted into the in-image cassette regions 77 of the electronic cassettes 16A, 16B, and 16D other than the use cassette.

For example, the cassette region index 78A and the cassette region index 78B are different in shape and the content of a message. Each message includes the name and cassette ID of the electronic cassette 16. The cassette region index 78A includes a message indicating the use cassette. As the aspect in which the cassette region indices 78A and 78B are distinguished from each other, various aspects in which colors are changed and one of the indicators is blinked unlike this embodiment are considered. Any aspect may be used as long as it can distinguish the cassette region indices 78A and 78B.

As such, since the cassette region indices 78 for all of the electronic cassettes 16 included in the camera image 76 are displayed, it is possible to check all of the electronic cassettes 16 in the usage environment at a glance. This display aspect is conveniently used in, for example, a case in which the cassette IDs of all of the electronic cassettes 16 in the usage environment are checked or a case in which a desired electronic cassette 16 is not found.

Figure 34:
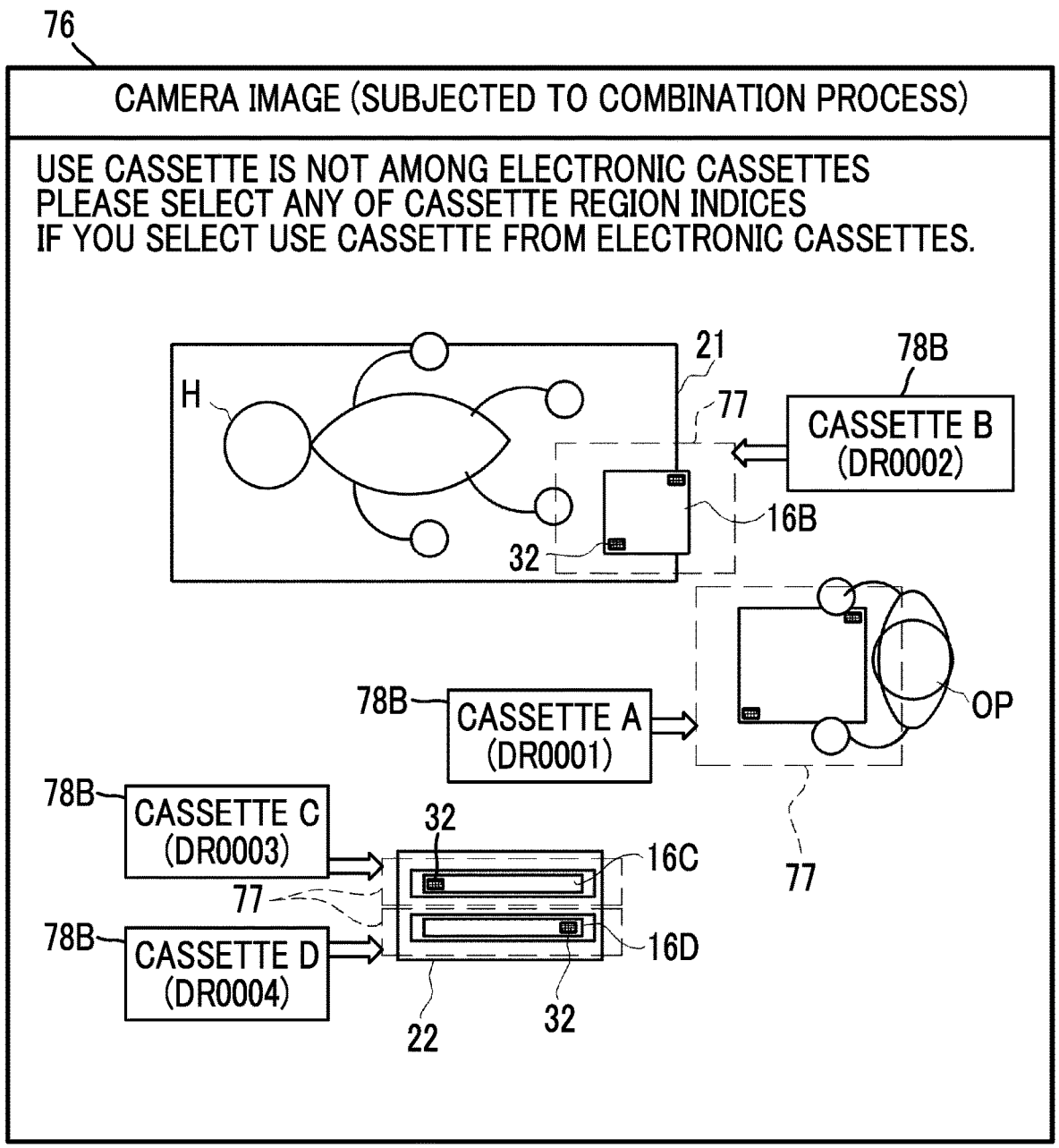
FIG. 34 is a diagram illustrating the outline of an electronic cassette selection operation receiving function according to the fifth embodiment.
Figure 35:
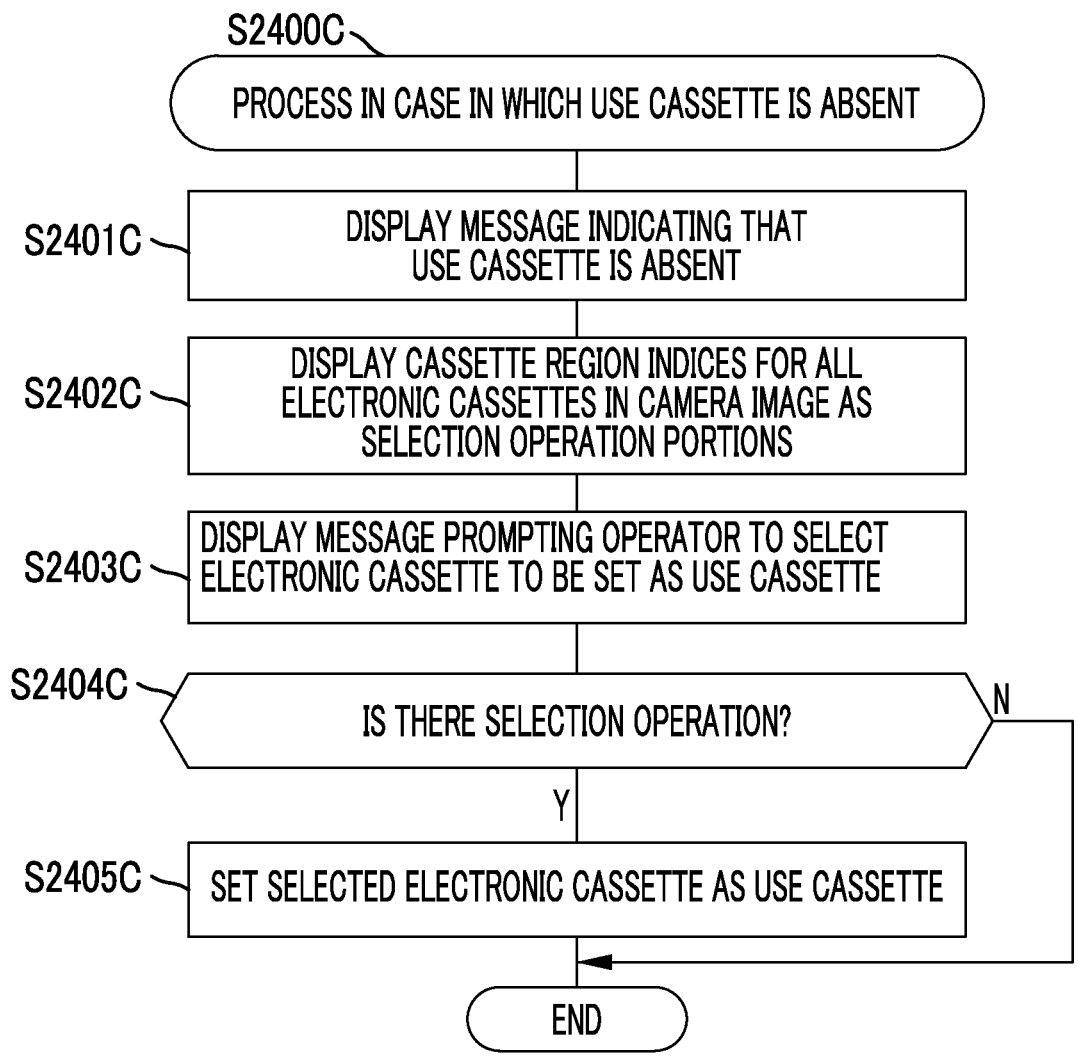
FIG. 35 is a flowchart illustrating the procedure of a process with a selection operation receiving function according to the fifth embodiment.

In the fifth embodiment, the following process may be performed in a case in which a plurality of electronic cassettes 16 are included in the camera image 76 and the use cassette is not among the plurality of electronic cassettes 16 as illustrated in FIGS. 34 and 35. That is, a process is performed which receives a selection operation of selecting any one of the electronic cassettes 16 as the use cassette through the camera image 76.

In this case, the search controller 74 generates the cassette region indices 78B for the in-image cassette regions 77 of all of the electronic cassettes 16 in the camera image 76 and outputs the cassette region indices 78B. The image combination unit 75 inserts all of the generated cassette region indices 78B into the camera image 76 as illustrated in FIG. 34. In the fifth embodiment, each of the cassette region indices 78B functions as a selection operation portion for the selection operation of selecting any one of the plurality of electronic cassettes 16 in the camera image 76 as the use cassette. The search controller 74 receives the input of an operation for the cassette region indices 78B displayed on the touch panel 33 through the GUI controller 51.

In the fifth embodiment, as the process in S2400 illustrated in FIG. 20, a process in S2400C illustrated in FIG. 35 is performed. The image combination unit 75 inserts a message indicating that the use cassette is absent into the camera image 76 and the camera image 76 having the message inserted thereinto is displayed on the touch panel 33 through the GUI controller 51 (S2401C).

The search controller 74 generates the cassette region indices 78B for all of the electronic cassettes 16 in the camera image 76 so as to function as the selection operation portions and outputs the cassette region indices 78B to the image combination unit 75. The image combination unit 75 inserts the generated cassette region indices 78B into the camera image 76 and displays the cassette region indices 78B as the selection operation portions (S2402C). In addition, the image combination unit 75 inserts a message prompting the operator to select the electronic cassette 16 to be set as the use cassette, for example, a message "Please select any of the cassette region indices if you select the use cassette from the electronic cassettes" into the camera image 76 and displays the camera image 76 (S2403C).

The operator OP sees the camera image 76 displayed on the touch panel 33 and touches the cassette region index 78B corresponding to the electronic cassette 16 selected as the use cassette. The search controller 74 receives the touch operation through the GUI controller 51. In a case in which the electronic cassette has been selected by the touch operation (Y in S2404C), the search controller 74 accesses the use cassette setting information 58 and sets the selected electronic cassette 16 as the use cassette (S2405C).

As such, in a case in which the use cassette can be set through the cassette region index 78 displayed on the camera image 76, for example, the operation is simpler than that in a case in which the use cassette selection screen 69 illustrated in (A) of FIG. 11 is displayed and the use cassette is set. In addition, since the cassette region indices 78 are displayed in the camera image 76, the operator OP can select the use cassette while checking the outward shape of the electronic cassettes 16 corresponding to each cassette region index 78. Therefore, a selection error, such as the selection of a wrong size, does not occur.

Sixth Embodiment

Figure 37:
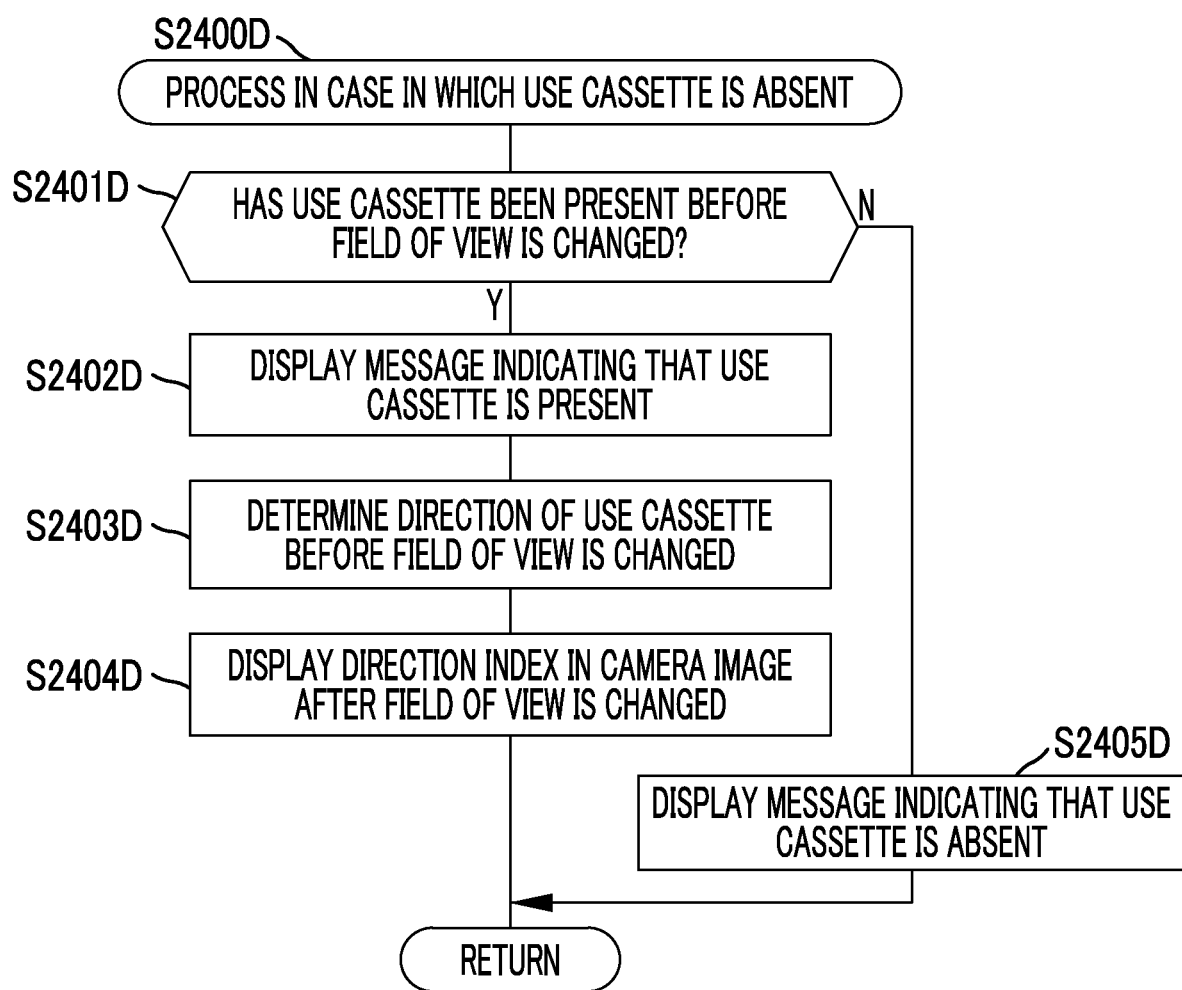
FIG. 37 is a flowchart illustrating the procedure of a process in a case in which the use cassette is absent in the sixth embodiment.

A sixth embodiment illustrated in FIGS. 36 and 37 relates to an example of a process in a case in which, after the field of view of the camera image 76 is changed, the use cassette included in the camera image 76 disappears from the camera image 76.

(A) of FIG. 36 illustrates an aspect of the usage environment before the field of view of the camera image 76 is changed and (B) of FIG. 36 illustrates an aspect of the usage environment after the field of view of the camera image 76 is changed. As illustrated in (A) of FIG. 36, the electronic cassette 16C set as the use cassette is included in the camera image 76 before the field of view is changed. Therefore, the cassette region index 78 for the in-image cassette region 77 of the electronic cassette 16C is displayed. In this state, for example, in a case in which the camera 26 faces the right and the field of view of the camera image 76 is moved to the right, the electronic cassette 16C disappears from the camera image 76 after the field of view is changed as illustrated in (B) of FIG. 36.

In this case, a direction index 88 indicating the direction in which the use cassette is present in the camera image 76 before the field of view is changed is displayed in the camera image 76. The direction in which the use cassette (in this example, the electronic cassette 16C) has been present in the camera image 76 illustrated in (A) of FIG. 36 before the field of view is changed in this example is the lower left side of the camera image 76. Then, in a case in which the field of view of the camera image 76 is moved to the right, the use cassette (in this example, the electronic cassette 16C) disappears from the camera image 76. Therefore, in the camera image 76 illustrated in (B) of FIG. 36 after the field of view is changed is used, the direction in which the use cassette is present is the left direction on the lower left side of the camera image 76 after the field of view is changed. The direction index 88 indicating the direction is displayed in the camera image 76. For example, an index with an arrow shape indicating the direction and a message "The use cassette is in this direction" are displayed in the direction index 88.

In addition, a message "The use cassette is absent in this camera image" indicating that the use cassette is absent in the camera image 76 is displayed in the camera image 76 illustrated in (B) of FIG. 36 after the field of view is changed.

In the sixth embodiment, S2400D illustrated in FIG. 37 is performed as the process in S2400 illustrated in FIG. 20. In a case in which the use cassette is determined to be present in the camera image 76, the search controller 74 stores the determination result and the in-image cassette region 77 of the use cassette in the camera image 76.

Then, in a case in which it is determined that the use cassette is absent in the camera image 76 due to a change in the field of view of the camera image 76, the search controller 74 performs the process in S2400D. The search controller 74 determines whether the use cassette has been present before the field of view is changed on the basis of the previous determination result (S2401D). Then, in a case in which the use cassette has not been present before the field of view is changed (N on S2401D), the image combination unit 75 displays a message indicating that the use cassette is absent (S2405D). Then, the process returns to the flow of FIG. 20.

On the other hand, in a case in which the use cassette has been present before the field of view is changed (Y on S2401D), the image combination unit 75 displays a message indicating that the use cassette is present in the camera image 76 (S2402D). In addition, the search controller 74 determines the direction in which the use cassette has been present before the field of view is changed on the basis of the previous determination result and the stored information of the in-image cassette region 77 of the use cassette (S2403D). Then, as illustrated in (B) of FIG. 36, the image combination unit 75 displays the direction index 88 corresponding to the determined direction in the camera image 76 after the field of view is changed (S2404D).

Seventh Embodiment

A seventh embodiment illustrated in FIG. 38 relates an example in which status information indicating an operating state is used as the first identification information and the second identification information of the electronic cassette 16, instead of the cassette ID. The first identification information and the second identification information are used to specify one electronic cassette 16 among a plurality of electronic cassettes 16. The status information can be used as the first identification information and the second identification information for specifying the use cassette as long as it can indicate that the status of the use cassette is different from the status of the other electronic cassettes 16 among a plurality of electronic cassettes 16 in the usage environment.

In FIG. 38, in the electronic cassette 16 according to the seventh embodiment, the housing 28 includes the indicators 84 as in the third embodiment illustrated in FIGS. 26 and 27. In the seventh embodiment, the indicator 84 can emit identification light indicating the status, such as a ready status, a sleep status, or a power-off status. The status identified by the identification light corresponds to the first identification information.

As illustrated in FIG. 38, the following lighting patterns of the identification light for each status are recorded in specification information of the registered cassette information 57: "fast flashing" indicates the "ready" status; "slow flashing" indicates the "sleep" status; and "no light" indicates the "power-off" status.

As illustrated in FIGS. 7 and 12, the status of the set use cassette is recorded in the use cassette setting information 58. The status recorded in the use cassette setting information 58 corresponds to the second identification information. As described above, in this example, the cassette controller 52 (see FIG. 5) of the console 17 changes the status of the electronic cassette 16 set as the use cassette from the power-off status or the sleep status to the ready status. The cassette controller 52 does not control the electronic cassettes 16 other than the use cassette. Therefore, the electronic cassettes 16 other than the use cassette are in the power-off status or the sleep status. Under this assumption, only the electronic cassette 16 that is in the ready status in the usage environment becomes the use cassette.

The identification information acquisition unit 73 recognizes the lighting pattern of the identification light of the indicator 84 on the basis of the camera image 76 and acquires the status information (corresponding to the first identification information) of the electronic cassette 16. The search controller 74 collates the first identification information with the status information (corresponding to the second identification information) of the use cassette acquired from the use cassette setting information 58 and determines whether the use cassette is included in the camera image 76.

As described above, only the electronic cassette 16 that is in the "ready" status in the usage environment is the use cassette and only the electronic cassette 16 that is in the "ready" status in the use cassette setting information 58 is the use cassette. Therefore, in a case in which there is an electronic cassette 16 that is in the "ready" status among the electronic cassettes 16 included in the camera image 76, the search controller 74 determines the electronic cassette 16 as the use cassette.

As such, the status information other than the cassette ID can be used as the first identification information and the second identification information. Therefore, according to the seventh embodiment, it is possible to achieve the function of searching for the electronic cassette 16, without providing the ID marker 32 on the housing 28. In addition, even in a case in which the indicator 84 does not have a function of emitting identification light indicating the cassette ID, it is possible to achieve the search function of the invention.

In this example, the status is identified by the lighting pattern of the identification light. However, similarly to the identification of the cassette ID, the status may be identified by the color of the identification light or the lighting time.

Eighth Embodiment

Figure 40:
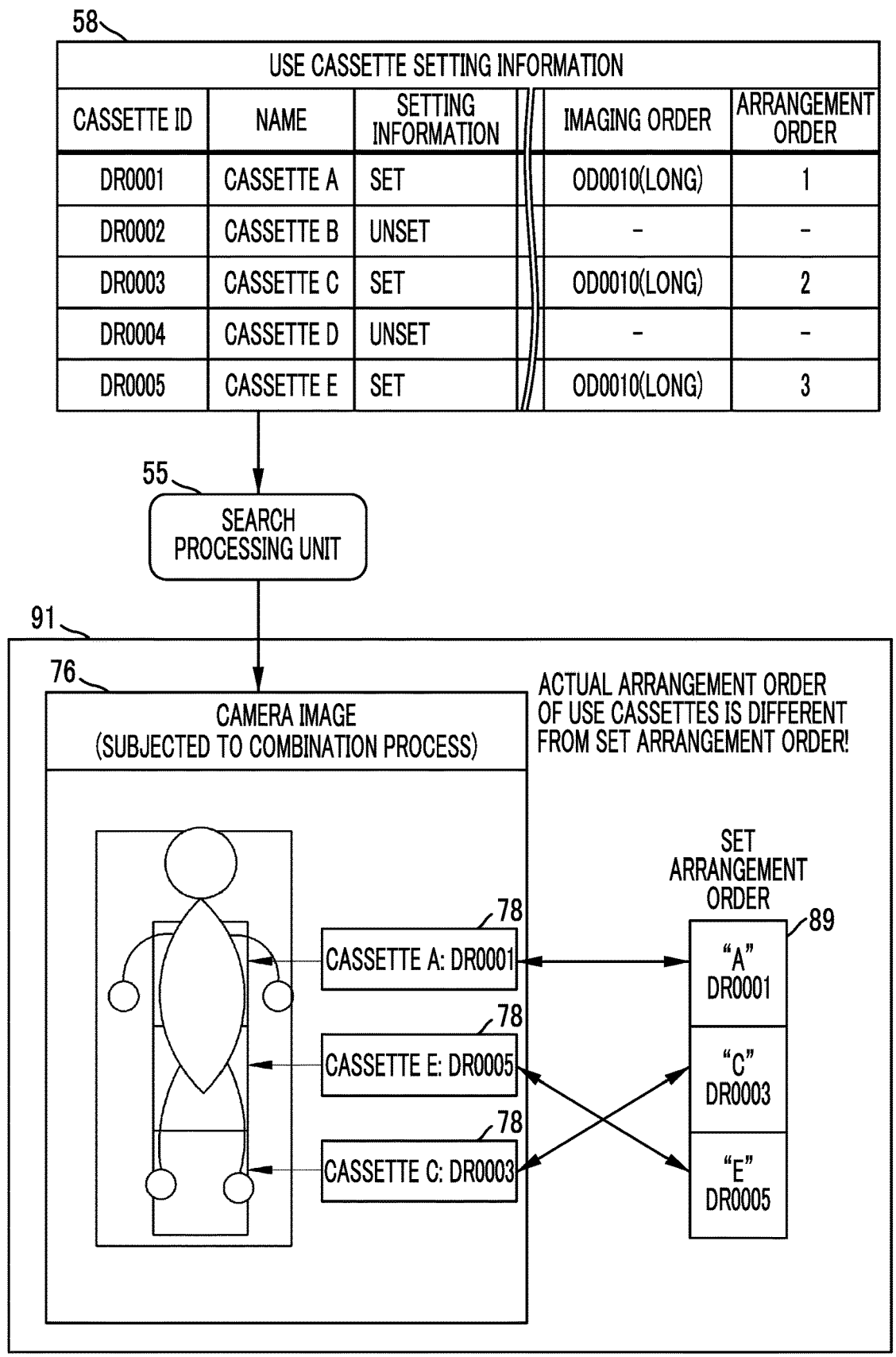
FIG. 40 is a diagram illustrating an electronic cassette arrangement order screen in long-length imaging.

In an eighth embodiment illustrated in FIGS. 39 and 40, the function of searching for the electronic cassette 16 is applied to achieve an arrangement order display function of displaying the arrangement order of a plurality of electronic cassettes 16 in a case in which long-length imaging is performed using the plurality of electronic cassettes 16.

As illustrated in FIG. 39, in the long-length imaging, for example, two or more electronic cassettes 16 are arranged in order to capture an image of a long range such as the whole lower limb of the subject H. The plurality of electronic cassettes 16 are irradiated with X-rays sequentially or at the same time. Then, a plurality of X-ray images detected by each electronic cassette 16 are combined to generate one X-ray image indicating a long imaging range such as the whole lower limb of the subject H.

In the long-length imaging, in a case in which three electronic cassettes 16A, 16C, and 16E are used as illustrated in (A) of FIG. 39, the electronic cassettes 16A, 16C, and 16E are arranged in a line on the bed 21 on which the subject H lies. The electronic cassettes 16A, 16C, and 16E are arranged on the bed 21 in the order of the electronic cassettes 16A, 16E, and 16C from the head of the subject H.

In a case in which the long-length imaging is performed, a plurality of (in this example, three) electronic cassettes 16 used in the long-length imaging are set as the use cassettes in the use cassette setting information 58 as illustrated in FIG. 40. In the case of the long-length imaging, in the use cassette setting information 58, an arrangement order item is added in addition to the imaging order item and the arrangement order of the three electronic cassettes 16 set as the use cassettes are designated in the arrangement order item. In the example illustrated in FIG. 40, an electronic cassette 16A with a name "cassette A" and a cassette ID "DR0001" is designated first, an electronic cassette 16C with a name "cassette C" and a cassette ID "DR0003" is designated second, and an electronic cassette 16E with a name "cassette E" and a cassette ID "DR0005" is designated third.

In a case in which the aspect illustrated in (A) of FIG. 39 is captured by the camera 26, of course, the three electronic cassette 16A, 16C, and 16E are included in the camera image 76 as illustrated in (B) of FIG. 39. The three electronic cassettes 16A, 16C, and 16E are set as the use cassettes in the use cassette setting information 58 illustrated in FIG. 40. In the search processing unit 55, the in-image cassette detection unit 72 detects the in-image cassette regions 77 of the electronic cassettes 16A, 16C, and 16E in the camera image 76 on the basis of the camera image 76. The identification information acquisition unit 73 acquires the first cassette IDs of the electronic cassettes 16A, 16C, and 16E in the detected in-image cassette regions 77 on the basis of the camera image 76.

The search controller 74 generates the cassette region indices 78 at the positions corresponding to the in-image cassette regions 77 of the electronic cassettes 16A, 16C, and 16E and outputs the cassette region indices 78 to the image combination unit 75. The cassette region indices 78 include the names and the first cassette IDs, which are the first identification information items, of the electronic cassettes 16A, 16C, and 16E. The arrangement order of the cassette region indices 78 reflects the actual arrangement order of the electronic cassettes 16A, 16C, and 16E in the usage environment. In the example illustrated in FIG. 39, the electronic cassette 16A (cassette A: DR0001), the electronic cassette 16E (cassette E: DR0005), and the electronic cassette 16C (cassette C: DR0003) are arranged in this order from the head of the subject H.

The arrangement order of the cassette region indices 78 corresponds to first arrangement order information in which the arrangement order of the electronic cassettes 16A, 16C, and 16E is represented by the first identification information (first cassette ID). The image combination unit 75 combines the camera image 76 and the cassette region indices 78. In this way, the first arrangement order information is displayed in the camera image 76.

In addition, the search controller 74 reads the arrangement order from the use cassette setting information 58 and outputs the arrangement order as arrangement order information 89 indicated by the second cassette ID to the image combination unit 75. The image combination unit 75 generates an arrangement order screen 91 on which the cassette region indices 78 corresponding to the first arrangement order information and the arrangement order information 89 corresponding to the second arrangement order information are displayed in parallel as illustrated in FIG. 40. The arrangement order screen 91 is displayed on the touch panel 33.

While the electronic cassettes 16A, 16C, and 16E are actually arranged in the order of "A", "E", and "C", the electronic cassettes 16A, 16C, and 16E are arranged in the order of "A", "C", and "E" in the arrangement order information 89 which is the set arrangement order. Therefore, the operator OP can see the arrangement order screen 91 to check that the actual arrangement order of the electronic cassettes 16A, 16C, and 16E is wrong.

Ninth Embodiment

A ninth embodiment illustrated in FIG. 41 relates to an example in which the camera 92 is not provided on the ceiling of the imaging room, but is provided in a treatment cart 93. The treatment cart 93 has, for example, the functions of an X-ray generation apparatus including an X-ray source 94 and the functions of a console on a carriage that can travel. The treatment cart 93 is provided with a touch panel 96 as a display unit of the console. An X-ray imaging system 100 includes the treatment cart 93 and the electronic cassette 16.

A camera 92 has the same functions as the camera 26 and is provided on a housing of the X-ray source 94. The camera 92 outputs the camera image 76 similarly to the camera 26 and the camera image 76 is displayed on the touch panel 96. As such, in a case in which the camera 92 is provided in the treatment cart 93, it is also possible to capture the usage environment in which the electronic cassette 16 is used. Therefore, the use of the X-ray imaging system 100 makes it possible to achieve the same electronic cassette search function as that in each of the above-described embodiments.

In X-ray imaging in a hospital room in which the treatment cart 93 is used, in some cases, a plurality of electronic cassettes 16 are carried in the hospital room. In this case, similarly to the case of the imaging room illustrated in FIG. 1, it is difficult to identify the use cassette among the electronic cassettes 16. Therefore, the invention is also effective in the ninth embodiment in which the camera 92 is provided in the treatment cart 93.

In each of the above-described embodiments, the example in which the console 17 has the use cassette search function has been described. However, the search function may be provided in an apparatus other than the console 17 or may be provided in a dedicated apparatus.

The camera image 76 according to each of the above-described embodiments may be used to check the external injuries of a patient, in addition to being used for the use cassette search function.

In each of the above-described embodiments, for example, the hardware structures of the processing units performing various processes, such as the GUI controller 51, the search processing unit 55, the in-image cassette detection unit 72, the identification information acquisition unit 73, the search controller 74, and the image combination unit 75, are the following various processors.

Various processors include, for example, a CPU, a programmable logic device (PLD), and a dedicated electric circuit. The CPU is a general-purpose processor that executes software (program) to function as various processing units as it is known. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

One processing unit may be one of the various processors or a combination of two or more processors of the same type or different types (for example, a combination of a plurality of FPGAs and a combination of a CPU and an FPGA). In addition, a plurality of processing units may be formed by one processor. As an example in which a plurality of processing units are formed by one processor, first, one processor is formed by a combination of one or more CPUs and software and the processor functions as the plurality of processing units. Second, a processor which is typified by a system-on-chip (SoC) and in which the overall function of a system including a plurality of processing units is implemented by one IC chip is used. As such, the hardware structure of various processing units is formed by one or more of the various processors.

In addition, specifically, the hardware structure of the various processors is an electric circuit (circuitry) which is a combination of circuit elements such as semiconductor elements.

An invention described in the following Supplementary Note 1 can be understood from the above description.

Supplementary Note 1

A radiography system includes: an electronic cassette that detects a radiographic image based on radiation which has been emitted from a radiation generation apparatus and transmitted through a subject; a console that communicates with the electronic cassette to acquire the radiographic image; a camera image acquisition processor that acquires a camera image, which indicates a usage environment including a place in which the electronic cassette is used and a periphery of the place, from an optical camera that captures the usage environment; an in-image cassette detection processor that detects the electronic cassette included in the camera image on the basis of the camera image and outputs an in-image cassette region of the detected electronic cassette; an identification information acquisition processor that acquires identification information of the electronic cassette included in the camera image as first identification information on the basis of the camera image; a collation processor that collates the first identification information with second identification information which is identification information of a use cassette set as the electronic cassette used for radiography in the console; a search control processor that determines the electronic cassette having the first identification information matched with the second identification information as the use cassette on the basis of a collation result of the collation processor, determines whether the use cassette is present in the camera image, generates a cassette region index indicating the in-image cassette region of the use cassette in a case in which the use cassette is determined to be present in the camera image, and outputs the cassette region index as a search result; and a display control processor that performs control such that the cassette region index and the camera image are displayed on a display unit.

Inventions described in the following Supplementary Notes 2 and 3 can be understood from the above description.

Supplementary Note 2

There is provided an operation program that causes a computer to execute a process performed by a radiography system including an electronic cassette that detects a radiographic image based on radiation which has been emitted from a radiation generation apparatus and transmitted through a subject and a console that communicates with the electronic cassette to acquire the radiographic image. The process includes: a camera image acquisition step of acquiring a camera image, which indicates a usage environment including a place in which the electronic cassette is used and a periphery of the place, from an optical camera which captures the usage environment; an in-image cassette detection step of detecting the electronic cassette included in the camera image on the basis of the camera image and outputting an in-image cassette region of the detected electronic cassette; an identification information acquisition step of acquiring identification information of the electronic cassette included in the camera image as first identification information on the basis of the camera image; a collation step of collating the first identification information with second identification information which is identification information of a use cassette set as the electronic cassette used for radiography in the console; a search control step of determining the electronic cassette having the first identification information matched with the second identification information as the use cassette on the basis of a collation result in the collation step, determining whether the use cassette is present in the camera image, generating a cassette region index indicating the in-image cassette region of the use cassette in a case in which the use cassette is determined to be present in the camera image, and outputting the cassette region index as a search result; and a display control step of performing control such that the cassette region index and the camera image are displayed on a display unit.

Supplementary Note 3

There is provided a search apparatus that is used in a radiography system including an electronic cassette that detects a radiographic image based on radiation which has been emitted from a radiation generation apparatus and transmitted through a subject and a console that communicates with the electronic cassette to acquire the radiographic image, searches for the electronic cassette, and includes: a camera image acquisition unit that acquires a camera image, which indicates a usage environment including a place in which the electronic cassette is used and a periphery of the place, from an optical camera that captures the usage environment; an in-image cassette detection unit that detects the electronic cassette included in the camera image on the basis of the camera image and outputs an in-image cassette region of the detected electronic cassette; an identification information acquisition unit that acquires identification information of the electronic cassette included in the camera image as first identification information on the basis of the camera image; a collation unit that collates the first identification information with second identification information which is identification information of a use cassette set as the electronic cassette used for radiography in the console; a search controller that determines the electronic cassette having the first identification information matched with the second identification information as the use cassette on the basis of a collation result of the collation unit, determines whether the use cassette is present in the camera image, generates a cassette region index indicating the in-image cassette region of the use cassette in a case in which the use cassette is determined to be present in the camera image, and outputs the cassette region index as a search result; and a display controller that performs control such that the cassette region index and the camera image are displayed on a display unit.

The invention is not limited to the X-rays and can also be applied to a case in which other types of radiation including γ-rays are used.

The invention is not limited to each of the above-described embodiments and can adopt various configurations without departing from the scope and spirit of the invention. In addition, the invention can be applied to a program and a storage medium storing the program.

EXPLANATION OF REFERENCES 10, 100: X-ray imaging system
11: X-ray generation apparatus
12: X-ray imaging apparatus
13, 94: X-ray source
13a: X-ray tube
13b: irradiation field limiter
13c: support
14: radiation source control device
16, 16A, 16B, 16C, 16D, 16E: electronic cassette
17: console
21: bed
22: cradle
23: irradiation switch
26, 92: camera
28: housing
29: communication unit
31: battery
32: marker
33, 96: touch panel
34: input device
35: storage device
36: memory
38: data bus
41: CPU
43: network
44: server
50: operation program
51: GUI controller
52: cassette controller
53: X-ray image processing unit
54: network communication unit
55: search processing unit
57: registered cassette information
58: use cassette setting information
59: imaging order information
61: imaging order display screen
62: patient information display region
63: imaging order display region
63a: display field
64: image display region
66: cassette selection button
67: cassette search button
68: setting button
69: use cassette selection screen
72: in-image cassette detection unit
73: identification information acquisition unit
74: search controller
75: image combination unit
76: camera image
77: in-image cassette region
78, 78A, 78B: cassette region index
81: message
82: irradiation prohibition signal output unit
84: indicator
86: request signal transmission unit
88: direction index
89: arrangement order information
91: arrangement order screen
93: treatment cart
H: subject
OP: operator

What is claimed is:

1. A radiography system comprising:
an electronic cassette that detects a radiographic image based on radiation which has been emitted from a radiation generation apparatus and transmitted through a subject;
a console that communicates with the electronic cassette to acquire the radiographic image;
a camera image acquisition unit that acquires a camera image, which indicates a usage environment including a place in which the electronic cassette is used and a periphery of the place, from an optical camera that captures the usage environment;
an in-image cassette detection unit that detects the electronic cassette included in the camera image on the basis of the camera image and outputs an in-image cassette region of the detected electronic cassette;
an identification information acquisition unit that acquires identification information of the electronic cassette included in the camera image as first identification information on the basis of the camera image;
a collation unit that collates the first identification information with second identification information which is identification information of a use cassette set as the electronic cassette used for radiography in the console;

a search controller that determines the electronic cassette having the first identification information matched with the second identification information as the use cassette on the basis of a collation result of the collation unit, determines whether the use cassette is present in the camera image, generates a cassette region index indicating the in-image cassette region of the use cassette in a case in which the use cassette is determined to be present in the camera image, and outputs the cassette region index as a search result; and a display controller that performs control such that the cassette region index and the camera image are displayed on a display unit.

2. The radiography system according to claim 1, wherein the camera image is a motion picture or a still image.

3. The radiography system according to claim 1, wherein the camera is provided in the radiation generation apparatus or is provided in a room in a case in which the usage environment is an indoor environment.

4. The radiography system according to claim 1, wherein the first identification information and the second identification information include a first cassette ID and a second cassette ID, each of which includes a character string uniquely given to each electronic cassette, respectively.

5. The radiography system according to claim 4, wherein, in a case in which an ID marker indicating the first cassette ID is attached to an outer surface of the electronic cassette, the identification information acquisition unit detects the ID marker from the camera image and acquires the first cassette ID, and the collation unit collates the first cassette ID with the second cassette ID.

6. The radiography system according to claim 1, wherein each of the first identification information and the second identification information includes information indicating an operating state of the electronic cassette.

7. The radiography system according to claim 1, wherein, in a case in which a light source that emits identification light which is light indicating the first identification information is provided in the electronic cassette, the identification information acquisition unit detects the identification light from the camera image and acquires the first identification information.

8. The radiography system according to claim 7, wherein the identification light is identified on the basis of at least one of a color, a lighting pattern, or a lighting time.

9. The radiography system according to claim 1, further comprising:

a direction detection unit that detects a direction in which the electronic cassette is present in the usage environment on the basis of the in-image cassette region; and a request signal transmission unit that transmits an identification information request signal for requesting the first identification information to the electronic cassette, wherein, in a case in which the electronic cassette is included in the camera image, the request signal transmission unit transmits the identification information request signal in the direction detected by the direction detection unit and receives the first identification information as a response from the electronic cassette, and the identification information acquisition unit acquires the first identification information received by the request signal transmission unit.

10. The radiography system according to claim 1, wherein the identification information acquisition unit outputs a warning in a case in which the electronic cassette is included in the camera image, but the first identification information is not capable of being acquired from the electronic cassette.

11. The radiography system according to claim 1, wherein, in a case in which a plurality of the electronic cassettes are included in the camera image, the search controller outputs only the cassette region index for the use cassette among all of the electronic cassettes in the camera image.

12. The radiography system according to claim 1, wherein, in a case in which a plurality of the electronic cassettes are included in the camera image, the in-image cassette detection unit detects the in-image cassette regions of all of the electronic cassettes in the camera image, the search controller generates the cassette region indices indicating the in-image cassette regions of all of the electronic cassettes, and in a case in which the use cassette is present in the camera image, the search controller outputs the cassette region indices of the use cassette and the electronic cassettes other than the use cassette in different aspects.

13. The radiography system according to claim 1, wherein, in a case in which the use cassette is absent in the camera image, the search controller outputs, as the search result, a message indicating that the use cassette is absent in the camera image.

14. The radiography system according to claim 1, wherein, in a case in which the use cassette is absent in the camera image, the display controller displays only the camera image on the display unit.

15. The radiography system according to claim 1, wherein, in a case in which a plurality of the electronic cassettes are included in the camera image and do not include the use cassette, the search controller outputs a selection operation portion for selecting any one of the plurality of electronic cassettes included in the camera image as the use cassette, receives an input of an operation for the selection operation portion through the selection operation portion displayed on the display unit, and sets the selected electronic cassette as the use cassette.

16. The radiography system according to claim 1, wherein, in a case in which a field of view of the camera image is changed and the use cassette that has been present in the camera image before the field of view is changed disappears from the camera image after the field of view is changed, the search controller outputs a direction index indicating a direction in which the use cassette that has been present in the camera image before the field of view is changed is present, and the display controller displays the camera image whose field of view has been changed and the direction index on the display unit.

17. The radiography system according to claim 1, further comprising:

an irradiation prohibition signal output unit that outputs an irradiation prohibition signal for prohibiting the start of the emission of the radiation in the radiation generation apparatus in a case in which the use cassette is absent in the camera image.

18. The radiography system according to claim 1, wherein, in long-length imaging in which radiography is performed, with two or more of electronic cassettes arranged in a line, and a plurality of radiographic images detected by the electronic cassettes are combined to generate a radiographic image indicating a long imaging range, in a case in which a plurality of electronic cassettes are included in the camera image and include two or more use cassettes, the search controller outputs the cassette region indices indicating the in-image cassette regions of the two or more use cassettes in the camera image.

19. The radiography system according to claim 18, wherein, in a case in which an arrangement order of the plurality of electronic cassettes used for the long-length imaging is set in the console, the search controller generates an arrangement order screen on which first arrangement order information in which the arrangement order of the plurality of electronic cassettes included in the camera image is represented by the first identification information and second arrangement order information in which an arrangement order of the plurality of electronic cassettes set in the console is represented by the second identification information are displayed in parallel.

20. A method for operating a radiography system comprising an electronic cassette that detects a radiographic image based on radiation which has been emitted from a radiation generation apparatus and transmitted through a subject and a console that communicates with the electronic cassette to acquire the radiographic image, the method comprising:

a camera image acquisition step of acquiring a camera image, which indicates a usage environment including a place in which the electronic cassette is used and a periphery of the place, from an optical camera that captures the usage environment;

an in-image cassette detection step of detecting the electronic cassette included in the camera image on the basis of the camera image and outputting an in-image cassette region of the detected electronic cassette;

an identification information acquisition step of acquiring identification information of the electronic cassette included in the camera image as first identification information on the basis of the camera image;

a collation step of collating the first identification information with second identification information which is identification information of a use cassette set as the electronic cassette used for radiography in the console;

a search control step of determining the electronic cassette having the first identification information matched with the second identification information as the use cassette on the basis of a collation result in the collation step, determining whether the use cassette is present in the camera image, generating a cassette region index indicating the in-image cassette region of the use cassette in a case in which the use cassette is determined to be present in the camera image, and outputting the cassette region index as a search result; and a display control step of performing control such that the cassette region index and the camera image are displayed on a display unit.

* * * * *